(12) United States Patent
Lou et al.

(10) Patent No.: US 10,093,930 B2
(45) Date of Patent: Oct. 9, 2018

(54) TARGETING WSB1 AND PVHL TO TREAT CANCER

(71) Applicant: Mayo Foundation for Medical Education and Research, Rochester, MN (US)

(72) Inventors: Zhenkun Lou, Rochester, MN (US); JungJin Kim, Rochester, MN (US); SeungBaek Lee, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/148,359

(22) Filed: May 6, 2016

(65) Prior Publication Data

US 2016/0326532 A1    Nov. 10, 2016

Related U.S. Application Data

(60) Provisional application No. 62/157,554, filed on May 6, 2015.

(51) Int. Cl.
| | | |
|---|---|---|
| *C12N 15/11* | (2006.01) | |
| *C12N 15/113* | (2010.01) | |
| *C12N 9/00* | (2006.01) | |
| *C07K 16/40* | (2006.01) | |
| *A61K 48/00* | (2006.01) | |

(52) U.S. Cl.
CPC .......... *C12N 15/1137* (2013.01); *C07K 16/40* (2013.01); *C12N 9/93* (2013.01); *C12N 15/1135* (2013.01); *C12Y 603/02019* (2013.01); *A61K 48/00* (2013.01); *C07K 2317/75* (2013.01); *C07K 2317/76* (2013.01); *C12N 2310/14* (2013.01); *C12N 2310/531* (2013.01)

(58) Field of Classification Search
None
See application file for complete search history.

(56) References Cited

U.S. PATENT DOCUMENTS

| 5,580,859 A | 12/1996 | Felgner et al. |
| 5,589,466 A | 12/1996 | Felgner et al. |
| 8,853,180 B2 | 10/2014 | Lou et al. |
| 2005/0130184 A1* | 6/2005 | Xu .................. C12N 15/111 435/6.16 |

FOREIGN PATENT DOCUMENTS

CN    103272221    9/2013

OTHER PUBLICATIONS

Abraham, "Cell cycle checkpoint signaling through the ATM and ATR kinases," *Genes Dev.*, 15(17):2177-2196, Sep. 1, 2001.
Archange et al., "The WSB1 gene is involved in pancreatic cancer progression," *PLoS One*, 3(6):e2475, Jun. 25, 2008.
Bartek et al., "DNA damage signalling guards against activated oncogenes and tumour progression," *Oncogene*, 26(56):7773-7779, Dec. 10, 2007.
Bartkova et al., "DNA damage response as a candidate anti-cancer barrier in early human tumorigenesis," *Nature*, 434(7035):864-870, Apr. 14, 2005.
Bartkova et al., "Oncogene-induced senescence is part of the tumorigenesis barrier imposed by DNA damage checkpoints," *Nature*, 444(7119):633-637, Nov. 30, 2006.
Benita et al., "An integrative genomics approach identifies Hypoxia Inducible Factor-1 (HIF-1)-target genes that form the core response to hypoxia," *Nucleic Acids Res.*, 37(14):4587-602, Epub Jun. 2, 2009.
Blum et al., "Ras inhibition in glioblastoma down-regulates hypoxia-inducible factor-1alpha, causing glycolysis shutdown and cell death," *Cancer Res.*, 65(3):999-1006, Feb. 1, 2005.
Bovellan et al., "Cellular control of cortical actin nucleation," *Curr Biol.*, 24(14):1628-1635, Epub Jul. 10, 2014.
Cairns et al., "Regulation of cancer cell metabolism," *Nat Rev Cancer*, 11(2):85-95, Feb. 2011.
Chen et al., "Bezielle selectively targets mitochondria of cancer cells to inhibit glycolysis and OXPHOS," *PLoS One*, 7(2):e30300, Epub Feb. 3, 2012.
Chen et al., "Increased WSB1 copy number correlates with its over-expression which associates with increased survival in neuroblastoma," *Genes Chromosomes Cancer.*, 45(9):856-862, Sep. 2006.
Chen et al., "Regulation of glut1 mRNA by hypoxia-inducible factor-1. Interaction between H-ras and hypoxia," *J Biol Chem.*, 276(12):9519-9525, Epub Dec. 18, 2000.
Chen et al., "TCTP increases stability of hypoxia-inducible factor 1α by interaction with and degradation of the tumour suppressor VHL," *Biol Cell.*, 105(5):208-218, Epub Mar. 15, 2013.
Chiu et al., "siRNA function in RNAi: a chemical modification analysis," *RNA*, 9(9):1034-1048, Sep. 2003.
Choi et al., "Ubiquitination and degradation of homeodomain-interacting protein kinase 2 by WD40 repeat/SOCS box protein WSB-1," *J Biol Chem.*, 283(8):4682-9. Epub Dec. 19, 2007.
Chun et al., "Oncogenic KRAS modulates mitochondrial metabolism in human colon cancer cells by inducing HIF-1alpha and HIF-2alpha target genes," *Mol Cancer.*, 9:293, Nov. 13, 2010.
Cole et al., "Monoclonal Antibodies and Cancer Therapy," Alan R. Liss, Inc., pp. 77-96, 1985.
Collado et al., "Cellular senescence in cancer and aging," *Cell*, 130(2):223-233, Jul. 27, 2007.
Cote et al., "Generation of human monoclonal antibodies reactive with cellular antigens," *Proc Natl Acad Sci U S A.*, 80(7):2026-2030, Apr. 1983.
Czauderna et al., "Structural variations and stabilising modifications of synthetic siRNAs in mammalian cells," *Nucleic Acids Res.*, 31(11):2705-2716, Jun. 1, 2003.

(Continued)

*Primary Examiner* — Ekaterina Poliakova-Georgantas
(74) *Attorney, Agent, or Firm* — Fish & Richardson P.C.

(57) ABSTRACT

Materials and methods for treating cancer (e.g., by reducing metastasis) are provided herein. For example, materials and methods for treating cancer by targeting WSB1 and/or pVHL are provided.

8 Claims, 43 Drawing Sheets

Specification includes a Sequence Listing.

(56) References Cited

OTHER PUBLICATIONS

Dang, "Links between metabolism and cancer," *Genes Dev.*, 26(9):877-890, May 1, 2012.

Dati et al., "c-erbB-2 and ras expression levels in breast cancer are correlated and show a co-operative association with unfavorable clinical outcome," *Int J Cancer.*, 47(6):833-838, Apr. 1, 1991.

Dentice et al., "The Hedgehog-inducible ubiquitin ligase subunit WSB-1 modulates thyroid hormone activation and PTHrP secretion in the developing growth plate," *Nat Cell Biol.*, 7(7):698-705. Epub Jun. 19, 2005.

Deshaies and Joazeiro, "RING domain E3 ubiquitin ligases," *Annu Rev Biochem.*, 78:399-434, 2009.

Di Micco et al., "Oncogene-induced senescence is a DNA damage response triggered by DNA hyper-replication," *Nature*, 444(7119):638-642, Nov. 30, 2006.

Eckert et al., "Involvement of Ras activation in human breast cancer cell signaling, invasion, and anoikis," *Cancer Res.*, 64(13):4585-4592, Jul. 1, 2004.

Escande et al., "Flavonoid apigenin is an inhibitor of the NAD+ ase CD38: implications for cellular NAD+ metabolism, protein acetylation, and treatment of metabolic syndrome," *Diabetes*, 62(4):1084-1093, Epub Nov. 19, 2012, print Apr. 2013.

Friedl et al., "Rho-directed forces in collective migration," *Nat Cell Biol.*, 16(3):208-210, Mar. 2014.

Gatenby et al., "Why do cancers have high aerobic glycolysis?" *Nat Rev Cancer.*, 4(11):891-899, Nov. 2004.

Gilkes et al., "Hypoxia and the extracellular matrix: drivers of tumour metastasis," *Nat Rev Cancer.*, 14(6):430-439, Epub May 15, 2014.

Gordan and Simon, "Hypoxia-inducible factors: central regulators of the tumor phenotype," *Curr Opin Genet Dev.*, 17(1):71-77, Epub Jan. 8, 2007.

Gorgouli et al., "Activation of the DNA damage checkpoint and genomic instability in human precancerous lesions," *Nature*, 434(7035):907-913, Apr. 14, 2005.

Gossage et al., "VHL, the story of a tumour suppressor gene," *Nat Rev Cancer.*, 15(1):55-64, Jan. 2015.

Guatelli et al., "Isothermal, in vitro amplification of nucleic acids by a multienzyme reaction modeled after retroviral replication," *Proc Natl Acad Sci U S A*, 87(5):1874-1878, Mar. 1990.

Guy et al., "Expression of the neu protooncogene in the mammary epithelium of transgenic mice induces metastatic disease," *Proc Natl Acad Sci U S A.*, 89(22):10578-10582, Nov. 15, 1992.

Guy et al., "Induction of mammary tumors by expression of polyomavirus middle T oncogene: a transgenic mouse model for metastatic disease," *Mol Cell Biol.*, 12(3):954-961, Mar. 1992.

Harper et al., "The DNA damage response: ten years after," *Mol Cell.*, 28(5):739-745, Dec. 14, 2007.

He et al., "DDB1 functions as a linker to recruit receptor WD40 proteins to CUL4-ROC1 ubiquitin ligases," *Genes Dev.*, 20(21):2949-2954, Nov. 1, 2006.

Hofmann et al., "HIPK2: A tumour suppressor that controls DNA damage-induced cell fate and cytokinesis," *Bioessays*, 35(1):55-64, Epub Nov. 21, 2012, print Jan. 2013.

Hyrup et al., "Peptide nucleic acids (PNA): synthesis, properties and potential applications," *Bioorg Med Chem.*, 4(1):5-23, Jan. 1996.

Jang et al., "Increased miR-708 expression in NSCLC and its association with poor survival in lung adenocarcinoma from never smokers," *Clin Cancer Res.*, 18(13):3658-3667, Epub May 9, 2012.

Jin et al., "A family of diverse Cul4-Ddb1-interacting proteins includes Cdt2, which is required for S phase destruction of the replication factor Cdt1," *Mol Cell.*, 23(5):709-721, Sep. 1, 2006.

Jin et al., "A systems approach identifies HIPK2 as a key regulator of kidney fibrosis," *Nat Med.*, 18(4):580-588, Mar. 11, 2012.

Jung et al., "E2-EPF UCP targets pVHL for degradation and associates with tumor growth and metastasis," *Nat Med.*, 12(7):809-816, Epub Jul. 2, 2006.

Kaelin et al., "Oxygen sensing by metazoans: the central role of the HIF hydroxylase pathway," *Mol Cell.*, 30(4):393-402, May 23, 2008.

Kaelin, "Molecular basis of the VHL hereditary cancer syndrome," *Nat Rev Cancer.*, 2(9):673-682, Sep. 2002.

Kaelin, "The von Hippel-Lindau tumour suppressor protein: O2 sensing and cancer," *Nat Rev Cancer.*, 8(11):865-873, Epub Oct. 16, 2008.

Kaelin, "Von Hippel-Lindau disease," *Annu Rev Pathol.*, 2:145-173, 2007.

Keith et al., "HIF1α and HIF2α: sibling rivalry in hypoxic tumour growth and progression," *Nat Rev Cancer.*, 12(1):9-22, Dec. 15, 2011.

Kim et al., "DBC1 is a negative regulator of SIRT1," *Nature*, 451(7178):583-586, Jan. 31, 2008.

Kim et al., "WSB1 promotes tumor metastasis by inducing pVHL degradation," *Genes Dev.*, 29(21):2244-2257, Nov. 1, 2015.

Kohler et al., "Continuous cultures of fused cells secreting antibody of predefined specificity," *Nature*, 256(5517):495-497, Aug. 7, 1975.

Kong et al., "Constitutive/hypoxic degradation of HIF-alpha proteins by the proteasome is independent of von Hippel Lindau protein ubiquitylation and the transactivation activity of the protein," *J Biol Chem.*, 282(21):15498-15505, Epub Apr. 2, 2007.

Kosbor et al., "The production of monoclonal antibodies from human lymphocytes," *Immunol Today.*, 4(3):72-79, Mar. 1983.

Kuraguchi et al., "Genetic mechanisms in Apc-mediated mammary tumorigenesis," *PLoS Genet.*, 5(2):e1000367, Epub Feb. 6, 2009.

Land et al., "Tumorigenic conversion of primary embryo fibroblasts requires at least two cooperating oncogenes," *Nature*, 304(5927):596-602, Aug. 18-24, 1983.

Larsson, "Oncogene- and tumor suppressor gene-mediated suppression of cellular senescence," *Semin Cancer Biol.*, 21(6):367-376, Epub Oct. 24, 2011.

Latif et al., "Identification of the von Hippel-Lindau disease tumor suppressor gene," *Science*, 260(5112):1317-1320, May 28, 1993.

Lee et al., "Ras proteins induce senescence by altering the intracellular levels of reactive oxygen species," *J Biol Chem.*, 274(12):7936-7940, Mar. 19, 1999.

Lee et al., "Romo1 is a negative-feedback regulator of Myc," *J Cell Sci.*, 124(Pt 11):1911-1924, Epub May 10, 2011.

Lewis, "PCR's Competitors are Alive and Well and Moving Rapidly Towards Commercialization," *Genetic Engineering News*, 12(9):1, 1992.

Li et al., "Hypoxia-inducible factor linked to differential kidney cancer risk seen with type 2A and type 2B VHL mutations," *Mol Cell Biol.*, 27(15):5381-5392, Epub May 25, 2007.

Lin et al., "Transcriptional amplification in tumor cells with elevated c-Myc," *Cell.*, 151(1):56-67, Sep. 28, 2012.

Liu et al., "Hypoxia and cell cycle regulation of the von Hippel-Lindau tumor suppressor," *Oncogene*, 30(1):21-31, Epub Aug. 30, 2010, print Jan. 6, 2011.

Los et al., "Expression pattern of the von Hippel-Lindau protein in human tissues," *Lab Invest.*, 75(2):231-238, Aug. 1996.

Lou et al., "BRCA1 participates in DNA decatenation," *Nat Struct Mol Biol.*, 12(7):589-593, Epub Jun. 19, 2005.

Lou et al., "MDC1 is coupled to activated CHK2 in mammalian DNA damage response pathways," *Nature*, 421(6926):957-961, Feb. 27, 2003.

Lou et al., "MDC1 maintains genomic stability by participating in the amplification of ATM-dependent DNA damage signals," *Mol Cell.*, 21(2):187-200, Jan. 20, 2006.

Lou et al., "MDC1 regulates DNA-PK autophosphorylation in response to DNA damage," *J Biol Chem.*, 279(45):46359-46362, Epub Sep. 17, 2004.

Lou et al., "Mediator of DNA damage checkpoint protein 1 regulates BRCA1 localization and phosphorylation in DNA damage checkpoint control," *J Biol Chem.*, 278(16):13599-13602, Epub Feb. 27, 2003.

Luo et al., "Sumoylation of MDC1 is important for proper DNA damage response " *EMBO J.*, 31(13):3008-3019, Epub May 25, 2012.

(56) References Cited

OTHER PUBLICATIONS

Luo et al., "Topoisomerase II alpha controls the decatenation checkpoint," Nat Cell Biol., 11(2):204-210, Epub Dec. 21, 2008, print Feb. 2009.
Majmundar et al., "Hypoxia-inducible factors and the response to hypoxic stress," Mol Cell., 40(2):294-309, Oct. 22, 2010.
Mallette et al., "The DNA damage signaling pathway is a critical mediator of oncogene-induced senescence," Genes Dev., 21(1):43-48, Jan. 1, 2007.
Minter-Dykhouse et al., "Distinct versus overlapping functions of MDC1 and 53BP1 in DNA damage response and tumorigenesis," J Cell Biol., 181(5):727-735, Epub May 26, 2008.
Montagner et al., "SHARP1 suppresses breast cancer metastasis by promoting degradation of hypoxia-inducible factors," Nature, 487(7407):380-384, Jul. 19, 2012.
Nie et al., "c-Myc is a universal amplifier of expressed genes in lymphocytes and embryonic stem cells," Cell, 151(1):68-79, Sep. 28, 2012.
Patra et al., "Hexokinase 2 is required for tumor initiation and maintenance and its systemic deletion is therapeutic in mouse models of cancer," Cancer Cell., 24(2):213-228, Epub Aug. 1, 2013.
PCR Primer: A Laboratory Manual, ed. by Dieffenbach and Dveksler, Cold Spring Harbor Laboratory Press, 1995.
Pickup et al., "The roles of TGFβ in the tumour microenvironment," Nat Rev Cancer., 13(11):788-799, Epub Oct. 17, 2013.
Podsypanina et al., "Oncogene cooperation in tumor maintenance and tumor recurrence in mouse mammary tumors induced by Myc and mutant Kras," Proc Natl Acad Sci U S A., 105(13):5242-5247, Epub Mar. 20, 2008.
Pozzebon et al., "BC-box protein domain-related mechanism for VHL protein degradation," Proc Natl Acad Sci U S A., 110(45):18168-18173, Epub Oct. 21, 2013.
Puca et al., "Regulation of p53 activity by HIPK2: molecular mechanisms and therapeutical implications in human cancer cells," Oncogene, 29(31):4378-4387, Epub May 31, 2010.
Rhodes et al., "Integrative analysis of the cancer transcriptome," Nat Genet., 37:S31-S37, Jun. 1, 2005.
Rinaldo et al., "HIPK2 controls cytokinesis and prevents tetraploidization by phosphorylating histone H2B at the midbody," Mol Cell., 47(1):87-98, Epub May 31, 2012.
Robey et al., "Hypoxia-inducible factor-1alpha and the glycolytic phenotype in tumors," Neoplasia, 7(4):324-330, Apr. 2005.
Sakamoto et al., "Targeting the Warburg effect that arises in tumor cells expressing membrane type-1 matrix metalloproteinase," J Biol Chem., 286(16):14691-14704, Epub Mar. 3, 2011.
Sarkisian et al., "Dose-dependent oncogene-induced senescence in vivo and its evasion during mammary tumorigenesis," Nat Cell Biol., 9(5):493-505, Epub Apr. 22, 2007.
Sebastian et al., "The histone deacetylase SIRT6 is a tumor suppressor that controls cancer metabolism," Cell, 151(6):1185-1199, Dec. 7, 2012.
Semenza, "Defining the role of hypoxia-inducible factor 1 in cancer biology and therapeutics," Oncogene, 29(5):625-634, Epub Nov. 30, 2009, print Feb. 4, 2010.
Semenza, "Hypoxia-inducible factor 1: oxygen homeostasis and disease pathophysiology," Trends Mol Med., 7(8):345-350, Aug. 2001.
Semenza, "Hypoxia-inducible factors: mediators of cancer progression and targets for cancer therapy," Trends Pharmacol Sci., 33(4):207-214, Epub Mar. 6, 2012.
Shackelford et al., "mTOR and HIF-1alpha-mediated tumor metabolism in an LKB1 mouse model of Peutz-Jeghers syndrome," Proc Natl Acad Sci U S A., 106(27):11137-11142, Epub Jun. 18, 2009.
Shichrur et al., "Potential role of WSB1 isoforms in growth and survival of neuroblastoma cells," Pediatric Research, 75(4):482-486, Jan. 17, 2014.
Silva et al., "Gathering insights on disease etiology from gene expression profiles of healthy tissues," Bioinformatics, 27(23):3300-3305, Epub Oct. 11, 2011.
Sinn et al., "Coexpression of MMTV/v-Ha-ras and MMTV/c-myc genes in transgenic mice: synergistic action of oncogenes in vivo," Cell, 49(4):465-475, May 22, 1987.
Soga, "Cancer metabolism: key players in metabolic reprogramming," Cancer Sci., 104(3):275-281, Epub Jan. 31, 2013.
Summerton and Weller, "Morpholino antisense oligomers: design, preparation, and properties," Antisense Nucleic Acid Drug Dev., 7(3):187-195, Jun. 1997.
Swarbrick et al., "Id1 cooperates with oncogenic Ras to induce metastatic mammary carcinoma by subversion of the cellular senescence response," Proc Natl Acad Sci U S A., 105(14):5402-5407, Epub Mar. 31, 2008.
Takai et al., "Tel2 regulates the stability of PI3K-related protein kinases," Cell, 131(7):1248-1259, Dec. 28, 2007.
Tong et al., "HIF1 regulates WSB-1 expression to promote hypoxia-induced chemoresistance in hepatocellular carcinoma cells," FEBS Lett., 587(16):2530-2535, Epub Jun. 19, 2013.
Uchida et al., "Prolonged hypoxia differentially regulates hypoxia-inducible factor (HIF)-1alpha and HIF-2alpha expression in lung epithelial cells: implication of natural antisense HIF-1alpha," J Biol Chem., 279(15):14871-14878, Epub Jan. 26, 2004.
Vasiliauskas et al., "SWiP-1: novel SOCS box containing WD-protein regulated by signalling centres and by Shh during development," Mech Dev., 82(1-2):79-94, Apr. 1999.
von Lintig et al., "Ras activation in normal white blood cells and childhood acute lymphoblastic leukemia," Clin Cancer Res., 6(5):1804-1810, May 2000.
Wang et al., "Reviewing once more the c-myc and Ras collaboration: converging at the cyclin D1-CDK4 complex and challenging basic concepts of cancer biology," Cell Cycle, 10(1):57-67, Epub Jan. 1, 2011.
Ward et al., "Metabolic reprogramming: a cancer hallmark even warburg did not anticipate," Cancer Cell, 21(3):297-308, Mar. 20, 2012.
Weiss, "Hot prospect for new gene amplifier," Science, 254(5036):1292-1293, Nov. 29, 1991.
Welford et al., "HIF1alpha delays premature senescence through the activation of MIF," Genes Dev., 20(24):3366-3371, Epub Dec. 1, 2006.
Willems et al., "A hitchhiker's guide to the cullin ubiquitin ligases: SCF and its kin " Biochim Biophys Acta., 1695(1-3):133-170, Nov. 29, 2004.
Wu et al., "MDC1 regulates intra-S-phase checkpoint by targeting NBS1 to DNA double-strand breaks," Proc Natl Acad Sci U S A., 105(32):11200-11205, Epub Aug. 4, 2008.
Yuan et al., "A c-Myc-SIRT1 feedback loop regulates cell growth and transformation " J Cell Biol., 185(2):203-211, Epub Apr. 13, 2009.
Yuan et al., "USP10 regulates p53 localization and stability by deubiquitinating p53," Cell, 140(3):384-396, Epub Jan. 21, 2010.

* cited by examiner

FIG. 1A

| Category | Functions Annotation | p-Value |
|---|---|---|
| Cancer | Development of malignant tumor | 3.08E-05 |
| Cancer | Cell transformation | 4.41E-04 |
| Cancer | Metastasis | 4.60E-04 |

FIG. 1D

| Column ID | p-value (WSB1 Status) | Fold-Change (WSB1 high vs. WSB1 low) |
|---|---|---|
| LRP10 | 5.59E-12 | 2.32836 |
| HGF | 2.25E-10 | 2.12789 |
| PDGFC | 2.65E-09 | 2.10185 |
| P4HA1 | 7.78E-10 | 2.05306 |
| EGF | 2.84E-06 | 2.02577 |
| PGK1 | 1.63E-08 | 1.97964 |
| ITF | 2.57E-09 | 1.94676 |
| ANGPT2 | 0.0012662 | 1.91768 |
| MMP9 | 3.54E-05 | 1.83981 |
| WSB1 | 5.71E-15 | 1.81071 |
| VEGFA | 1.14E-05 | 1.74901 |
| LEPREL1 | 3.59E-05 | 1.73020 |
| ALDH1A1 | 6.02E-06 | 1.69195 |
| HK2 | 3.52E-06 | 1.68313 |
| DECR1 | 4.02E-07 | 1.60299 |
| COL5A1 | 0.0002861 | 1.59272 |
| LDHB | 2.13E-05 | 1.58351 |
| MET | 0.00029453 | 1.56095 |
| MMP2 | 3.50E-08 | 1.55623 |
| TGFA | 0.0001149 | 1.55201 |
| EPOR | 5.06E-05 | 1.51020 |
| CA4 | 0.011951 | 1.78189 |
| NDRG1 | 2.12E-05 | 1.56453 |

FIG. 3A

Diseases and Disorders

| Name | p-value | # Molecules |
|---|---|---|
| Cancer | 6.90E-10 - 6.33E-03 | 703 |
| Infectious Disease | 7.62E-08 - 4.42E-03 | 293 |
| Developmental Disorder | 3.79E-07 - 5.70E-03 | 265 |
| Organismal Injury and Abnormalities | 2.94E-06 - 5.65E-03 | 132 |
| Reproductive System Disease | 3.02E-06 - 6.22E-03 | 245 |

Molecular and Cellular Functions

| Name | p-value | # Molecules |
|---|---|---|
| Gene Expression | 4.27E-12 - 6.32E-03 | 401 |
| Cellular Assembly and Organization | 5.05E-11 - 6.04E-03 | 330 |
| Cellular Function and Maintenance | 5.05E-11 - 6.39E-03 | 452 |
| Cellular Growth and Proliferation | 9.79E-11 - 6.65E-03 | 661 |
| Cell Death and Survival | 1.60E-10 - 6.04E-03 | 545 |

Physiological System Development and Function

| Name | p-value | # Molecules |
|---|---|---|
| Organismal Survival | 2.26E-08 - 3.99E-03 | 334 |
| Organismal Development | 1.21E-08 - 6.63E-03 | 396 |
| Organismal Functions | 1.22E-08 - 4.19E-03 | 54 |
| Tissue Morphology | 1.22E-08 - 6.34E-03 | 392 |
| Cardiovascular System Development and Function | 1.61E-07 - 6.33E-03 | 248 |

Top Canonical Pathways

| Name | p-value | Ratio |
|---|---|---|
| RAR Activation | 2.85E-05 | 36/188 (0.19) |
| RhoA Signaling | 9.48E-05 | 25/114 (0.219) |
| Molecular Mechanisms of Cancer | 9.12E-04 | 53/377 (0.141) |
| Acute Myeloid Leukemia Signaling | 1.22E-03 | 17/62 (0.274) |
| BMP signaling pathway | 1.82E-03 | 16/80 (0.2) |

FIG. 3B

| Top Tox Findings | | |
|---|---|---|
| Assays: Clinical Chemistry and Hematology | | |
| Name | p-value | # Molecules |
| Increased Levels of Red Blood Cells | 5.88E-03 - 5.88E-03 | 18 |
| Increased Levels of Hematocrit | 5.88E-02 - 5.88E-02 | 15 |
| Increased Levels of Albumin | 9.92E-02 - 9.92E-02 | 1 |
| Increased Levels of Alkaline Phosphatase | 2.69E-01 - 1.00E00 | 7 |
| Cardiotoxicity | | |
| Name | p-value | # Molecules |
| Cardiac Dysfunction | 5.73E-04 - 8.48E-01 | 18 |
| Cardiac Hypertrophy | 8.71E-04 - 3.00E-01 | 59 |
| Congenital Heart Anomaly | 2.69E-03 - 1.00E00 | 22 |
| Cardiac Fibrosis | 4.16E-03 - 5.45E-01 | 30 |
| Cardiac Arrythmia | 9.83E-03 - 8.04E-01 | 23 |
| Hepatotoxicity | | |
| Name | p-value | # Molecules |
| Liver Proliferation | 1.08E-03 - 3.73E-01 | 31 |
| Liver Necrosis/Cell Death | 1.34E-02 - 6.09E-01 | 30 |
| Liver Cirrhosis | 1.49E-02 - 2.69E-01 | 23 |
| Liver Cholestasis | 3.22E-02 - 5.19E-01 | 19 |
| Glutathione Depletion in Liver | 4.16E-02 - 8.48E-01 | 6 |
| Nephrotoxicity | | |
| Name | p-value | # Molecules |
| Renal Necrosis/Cell Death | 4.16E-03 - 5.28E-01 | 45 |
| Glomerular Injury | 1.49E-02 - 4.11E-01 | 18 |
| Kidney Failure | 3.45E-02 - 1.00E00 | 24 |
| Renal Damage | 5.15E-02 - 5.73E-01 | 31 |
| Renal Proliferation | 5.58E-02 - 4.86E-01 | 28 |

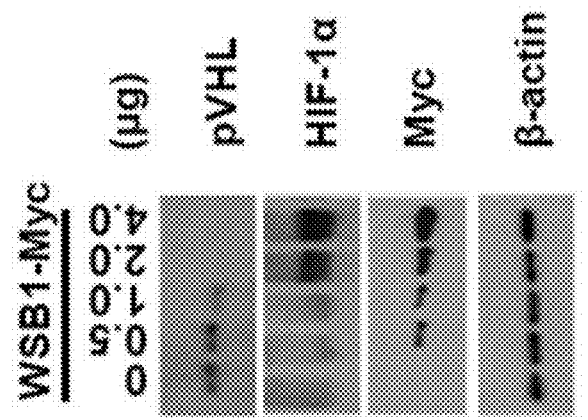
FIG. 8C
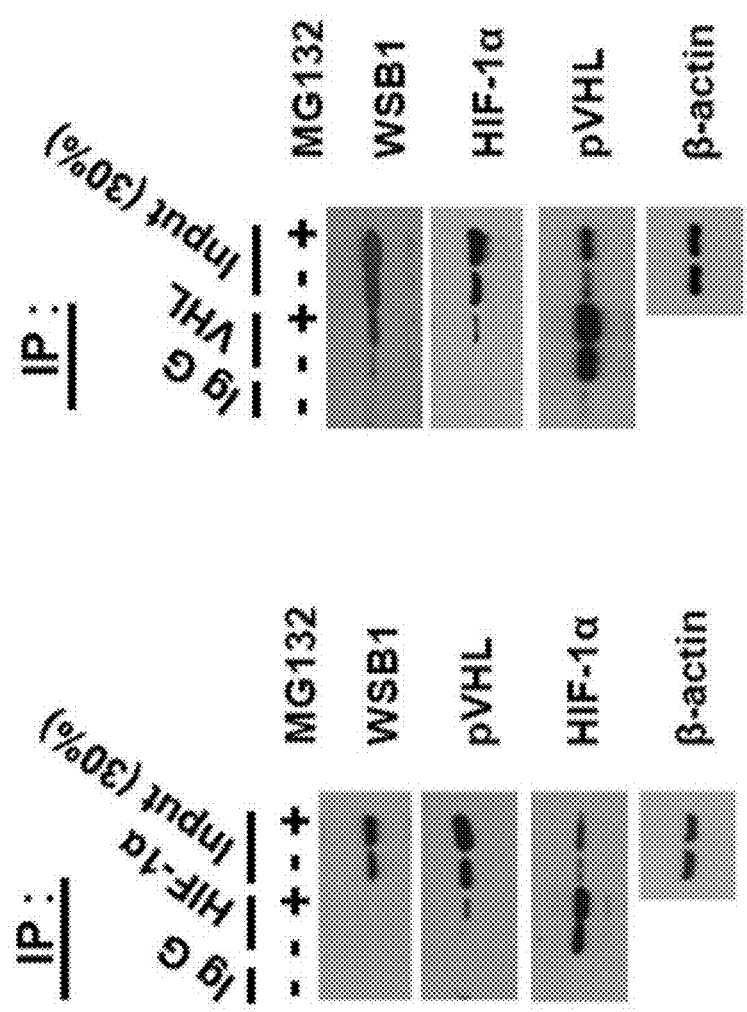
FIG. 8B
FIG. 8A

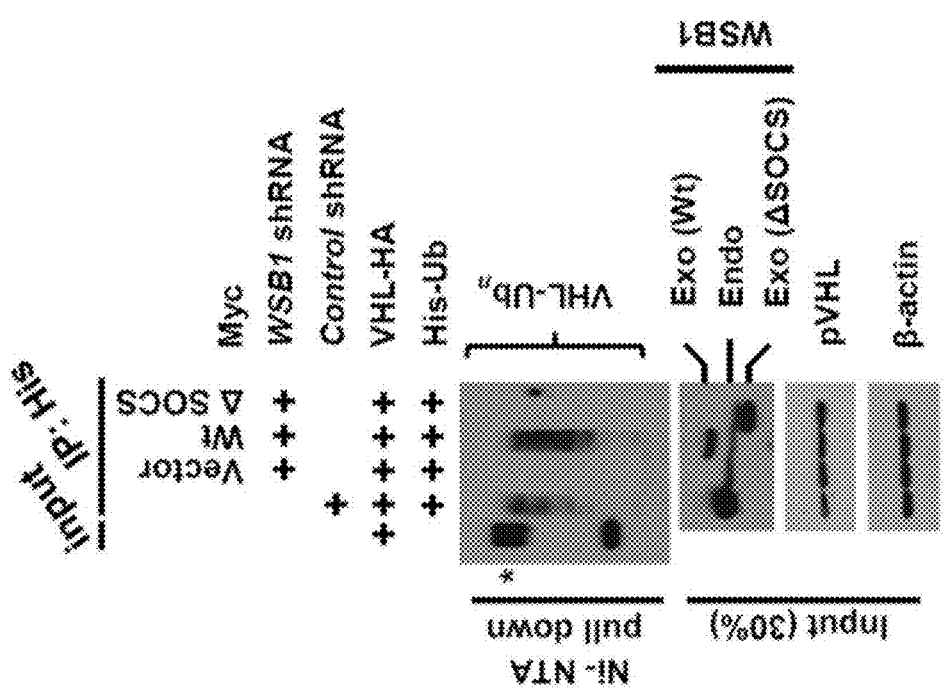

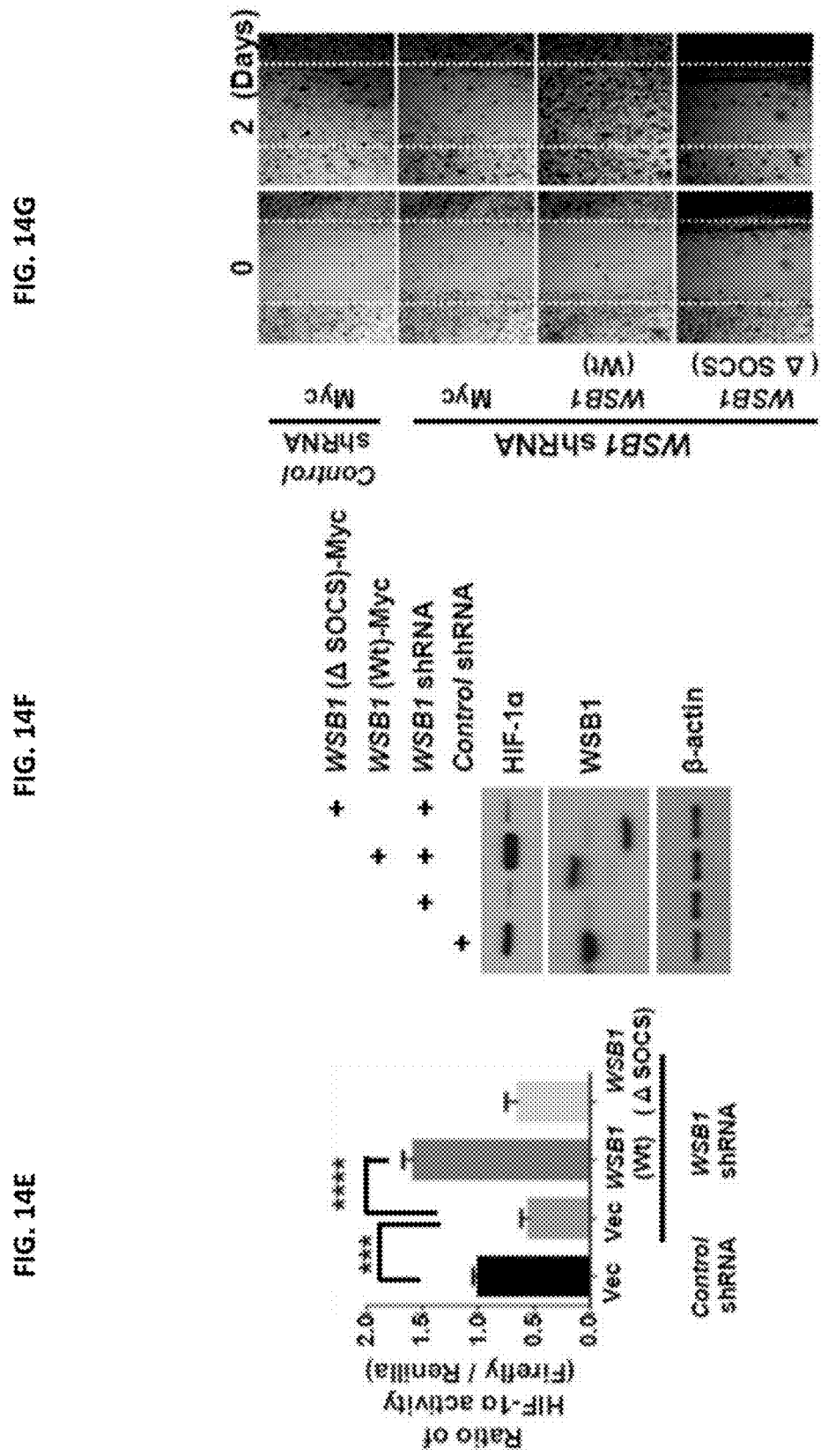

TARGETING WSB1 AND PVHL TO TREAT CANCER

CROSS-REFERENCE TO RELATED APPLICATIONS

This application claims benefit of priority from U.S. Provisional Application Ser. No. 62/157,554, filed on May 6, 2015.

STATEMENT AS TO FEDERALLY SPONSORED RESEARCH

This invention was made with government support under CA189666, awarded by the National Institutes of Health. The government has certain rights in the invention.

TECHNICAL FIELD

This document relates to materials and methods for treating cancer and/or inhibiting cancer metastasis, such as materials and methods for treating cancer by targeting WSB1 and/or pVHL.

BACKGROUND

The loss of pVHL leads to von Hippel-Lindau disease, which is characterized by development of tumors that can include renal clear-cell carcinomas (RCCs) and other highly vascularized tumors (Kaelin, *Ann Rev Pathol* 2:145-173, 2007; Kaelin, *Nature Rev Cancer* 2:673-682, 2002; and Latif et al., *Science* 260:1317-1320, 1993). pVHL is the substrate-recognition component of a cullin RING ubiquitin ligase complex also that includes elongin B, elongin C, Rbx1 and Cul2 (Deshaies and Joazeiro, *Ann Rev Biochem* 78:399-434, 2009; and Kaelin, *Nature Rev Cancer* 8:865-873, 2008). pVHL's main function as an E3 ligase is to target HIF-1α for degradation during normoxia (Kaelin 2002, supra). The loss of pVHL results in constitutive activation of HIF-1α, which acts as an important transcription factor for target genes such as VEGF, GULT1, CAIX, and HK2 (Gossage et al., *Nature Rev Cancer* 15:55-64, 2015). As a consequence, HIF-1α induces metabolic adaptation and promotes tumor growth, invasion, migration, metastasis, and angiogenesis through up regulation of its target genes (Gordan and Simon, *Curr Opin Genet Devel* 17:71-77, 2007; Semenza, *Trends Mol Med* 7:345-350, 2001; and Semenza, *Oncogene* 29:625-634, 2010).

pVHL is ubiquitously expressed in normal tissues and cell types (Los et al., *Laboratory Investigation; A Journal of Technical Methods and Pathology* 75:231-238, 1996). Loss of the VHL gene and germline mutations are important mechanisms of pVHL down regulation in various cancers (Gossage et al., supra), but the regulation of pVHL at the posttranscriptional level remains underexplored. pVHL may be regulated through the ubiquitin—proteasome pathway (Chen et al., *Biology of the Cell/Under the Auspices of the European Cell Biology Organization* 105:208-218, 2013; Jung et al., *Nature Med* 12:809-816, 2006; and Pozzebon et al., *Proc Natl Acad Sci USA* 110:18168-18173 2013), although the identity of pVHL's E3 ligase is not clear.

WD repeat and SOCS box-containing protein 1 (WSB1) has been classified as a substrate recognition subunit of the ECS (ElonginB/CCul2/5-SOCS) ubiquitin ligase complexes (Vasiliauskas et al., *Mech Devel* 82:79-94, 1999). WSB1 harbors seven WD40 repeats and a SOCS box (Choi et al., *J Biol Chem* 283:4682-4689, 2008). The expression of WSB1 positively correlates with tumor incidence in cancers such as pancreatic cancer, hepatocellular carcinoma, and salivary gland tumor (Archange et al., *PloS One* 3:e2475, 2008; Rhodes and Chinnaiyan, *Nature Genet* 37(Suppl): 531-37, 2005; Silva et al., *Bioinformatics* 27:3300-3305, 2011; and Tong et al., *FEBS Lett* 587:2530-2535, 2013). WSB1 also is a target of HIF-1 (Tong et al., supra).

The cellular function of WSB1 has not been well studied. WSB1 can mediate homeodomain-interacting protein kinase 2 (HIPK2) ubiquitination, resulting its proteasome degradation (Choi et al., supra). Following DNA damage, WSB1-mediated ubiquitination of HIPK2 is blocked, resulting in HIPK2 stabilization. HIPK2 in turn phosphorylates p53 at Ser46, which is important for activating proapoptotic gene expression (Puca et al., *Oncogene* 29:4378-4387, 2010). WSB1 overexpression has been shown to promote pancreatic cancer cell proliferation (Archange et al., supra). However, this effect is unlikely due to inactivation of HIPK-p53 pathway, as the pancreatic cancer cell line used in the study contains mutant p53. Thus, WSB1 may promote cancer cell proliferation through other p53-independent mechanisms.

SUMMARY

This document is based, at least in part, on the discovery that WSB1 is a negative regulator of pVHL through WSB1's E3 ligase activity. Mechanistically, WSB1 promotes pVHL ubiquitination and proteasomal degradation, thereby stabilizing HIF under both of normoxia and hypoxia conditions. As a consequence, WSB1 upregulates the expression of HIF-1α's target genes and promotes cancer invasion and metastasis through its effect on pVHL. Consistent with this, WSB1 protein levels are negatively correlated with pVHL levels and metastasis-free survival in clinical samples. The work described herein reveals a new mechanism of pVHL's regulation, by which cancer acquires invasiveness and metastatic tendency.

In one aspect, this document features a method for treating a cancer patient by administering to the cancer patient an agent that reduces the activity of WSB1. The agent can be an inhibitory nucleic acid (e.g., a shRNA) targeted to a WSB1 nucleic acid that is endogenous to the cancer patient, or can be an antagonistic antibody to WSB1. The method can include administering to the cancer patient a composition containing the agent and a pharmaceutically acceptable carrier.

In another aspect, this document features a method for inhibiting metastasis of a tumor in a cancer patient by administering to the cancer patient an agent that reduces the activity of WSB1. The agent can be an inhibitory nucleic acid (e.g., a shRNA) targeted to a WSB1 nucleic acid that is endogenous to the cancer patient, or can be an antagonistic antibody to WSB1. The method can include administering to the cancer patient a composition containing the agent and a pharmaceutically acceptable carrier.

In another aspect, this document features a method for treating a cancer patient by administering to the cancer patient an agent that increases the activity of pVHL. The agent can be a nucleic acid encoding a pVHL polypeptide (e.g., a nucleic acid operably linked to a promoter that drives expression of the nucleic acid), a pVHL polypeptide, or an agonistic antibody to pVHL. The method can include administering to the cancer patient a composition containing the agent and a pharmaceutically acceptable carrier.

This document also features a method for inhibiting metastasis of a tumor in a cancer patient by administering to the cancer patient an agent that increases the activity of pVHL. The agent can be a nucleic acid encoding a pVHL polypeptide (e.g., a nucleic acid operably linked to a promoter that drives expression of the nucleic acid), a pVHL polypeptide, or an agonistic antibody to pVHL. The method can include administering to the cancer patient a composition containing the agent and a pharmaceutically acceptable carrier.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A-1E demonstrate that WSB1 is positively related with metastasis and expression of HIF target genes. FIG. 1A is a table containing an analysis of differentially expressed genes by WSB1 expression levels in lung adenocarcinoma patients using INGENUITY pathway analysis. FIG. 1B is a series of graphs plotting levels of WSB1 expression in primary and metastatic melanoma (left panel), prostate cancer (center panel), and urinary bladder cancer (right panel) (GEO data sets GSE840, GSE6916, and GSE3167), demonstrating that WSB1 is highly expressed in human metastatic cancers. FIG. 1C is a series of Kaplan-Meier graph for human breast (left and center panels) and colon (right panel) cancer patients, stratified according to high or low expression levels of WSB1 (using PROGgene). FIG. 1D is a table listing potential HIF-1α target genes that may be associated with WSB1 expression levels in lung adenocarcinoma patients. FIG. 1E is a series of graphs plotting the co-relation between WSB1 and HIF target gene expression in metastatic melanoma (top row), prostate (middle row), and breast (bottom row) cancer patients (GEO data set).

FIGS. 3A and 3B are a series of tables listing gene expression profiles determined using total RNA from 56 pairs of FF primary never smoker lung adenocarcinomas, analyzed by WSB1 status using INGENUITY pathway analysis.

FIG. 6A shows a series of representative immunoblots from experiments in which HEK 293T cells were transfected with the indicated Myc, WSB1-Myc, and shRNA constructs, and levels of HIF-1α, Myc, WSB1, and β-actin were examined. FIG. 6B is a series of representative images of HIF-1α protein expression in HeLa cells that were transfected with WSB1 shRNA (#1) (GFP positive) and then stained with DAPI (blue for DNA) and anti-HIF-1α (red). The position of a cell transfected by WSB1 shRNA is indicated by the white arrowheads. The scale bar represents 10 μm. FIGS. 6C and 6D contain graphs plotting the results of quantitative polymerase chain reaction (qPCR) analyses of selected HIF-1α targets in HEK 293T cells stably transfected with WSB1 cDNA (FIG. 6C) or WSB1 shRNA (FIG. 6D). Expression levels are relative to β-actin; data are normalized to control cells. The results represent the means (±S.E.) of three independent experiments performed in triplicate. *$P<0.05$, $P<0.01$, *$P<0.001$ versus control cells by one-way ANOVA.

FIG. 7A contains representative images of HIF-1α protein expression in HeLa cells that were transfected with WSB1 shRNA (#2) (GFP positive) and then stained with DAPI (blue for DNA) and anti-HIF-1α (red). The position of a cell transfected by WSB1 shRNA is indicated by the white arrowheads. The scale bar represents 10 μm. FIG. 7B is a graph plotting relative mRNA levels for the indicated genes in cells infected with WSB1 shRNA (#2) and then collected for qPCR analysis.

FIGS. 8A-8G demonstrate that WSB1 regulates pVHL ubiquitination and degradation. FIG. 8A contains representative immunoblots from co-immunoprecipitation (Co-IP) of endogenous HIF-1α and WSB1 from extracts of HEK 293 T cells. FIG. 8B contains representative immunoblots from Co-IP of endogenous pVHL and WSB1 from extracts of HEK 293T cells. FIG. 8C contains representative immunoblots showing regulation of pVHL and HIF-1α protein levels by WSB1 in a dose dependent manner. Cells were transfected with the indicated amounts of WBS1 constructs, and pVHL and HIF-1α levels were examined. FIG. 8D contains representative immunoblots showing that down regulation of pVHL levels by WSB1 was reversed by MG 132. Cells transfected with WSB1-Myc were left untreated or treated with MG 132, and pVHL levels were examined. FIG. 8E contains representative immunoblots showing pVHL levels in cells transfected with the indicated WSB1 shRNAs. FIG. 8F contains representative immunoblots (left panel) and a graph (right panel), showing pVHL levels in cells stably expressing control shRNA, WSB1 shRNA, or WSB1 shRNA together with shRNA-resistant WSB1. Cells were treated with cycloheximide (0.1 mg/ml) and harvested at the indicated times. The graph quantifies the VHL protein expression levels shown in the left panel. $P<0.01$, *$P<0.001$ versus control shRNA by one way ANOVA. FIG. 8G contains representative immunoblots for cells that were transfected with the indicated constructs and were then treated with MG 132. Ubiquitinated proteins were pulled down under denaturing conditions by Ni-NTA Agarose and analyzed by immunoblotting. pVHL-Ub$_n$, polyubiquitinated pVHL.

FIG. 9A contains representative immunoblots from Co-IP of exogenous HIF-1α, pVHL, and WSB1 from extracts of HEK 293T cells. FIG. 9B contains representative immunoblots from five lung, six pancreatic, and four breast cancer cell lines, as well as normal MCF10A cells, that were analyzed by immunoblotting for the indicated proteins.

FIGS. 10A-10E demonstrate that WSB1 interacts with and degrades pVHL through its SOCS domain. FIG. 10A is a diagram of WT WSB1 and corresponding deletion mutants (ΔWD 1-3, ΔWD 1-5, ΔSOCS, and Δ6-SOCS) as used in Co-IP experiments with pVHL. Plus and minus symbols indicate the binding affinity of each WSB1 protein for pVHL. Arrows indicate the effect of the WSB1 proteins (decreasing pVHL stability). FIG. 10B contains representative immunoblots for cells transfected with the indicated plasmids. For the blots in the left panel, cells were pretreated with MG 132, and the WSB1-pVHL interaction was examined by IP. In the right panel, pVHL levels were examined without MG 132 pretreatment. FIG. 10C contains representative immunoblots showing that deleting the SOCS domain from WSB1 inhibits WSB1's E3 ligase activity toward pVHL. Cells were transfected with the indicated constructs and then treated with MG 132. Ubiquitinated proteins were pulled down under denaturing conditions by Ni-NTA agarose and analyzed by immunoblotting. *non-specific band. FIG. 10D is a representative immunoblot for an in vitro binding assay of recombinant WSB1 with pVHL. FIG. 10E contains representative immunoblots for WSB1 (WT or ΔSOCS) that was purified from cells and used for in vitro ubiquitination reactions with recombinant pVHL.

FIG. 11A contains representative immunoblots from experiments in which endogenous WSB1 was co-immunoprecipitated with pVHL from 293T cell extracts under hypoxia for the indicated time. The 0 time point represents lysates from normoxic cultures that were prepared at the time of transfer to hypoxia. FIG. 11B contains representative immunoblots (left panel) and RT-PCR results (right panel) showing HIF-1α, HIF-2α, and WSB1 protein levels, as well as levels of HIF-1α, GULT1, WSB1 and VHL mRNA, after the indicated time of hypoxia. FIG. 11C is a picture of a representative gel showing the ubiquitination of pVHL under hypoxia conditions in HEK 293 cells transfected with control or WSB1 shRNA, as indicated. FIG. 11D contains representative immunoblots showing HIF-1α expression in cells transfected with control or WSB1 shRNA and subjected to hypoxia conditions.

FIG. 12A contains representative immunoblots for cells treated with $CoCl_2$ and then collected for immunoprecipitation (IP) and immunoblot analysis. FIG. 12B contains representative immunoblots showing levels of HIF-1α, HIF-2α, pVHL, and WSB1 after $CoCl_2$ treatment.

FIG. 13A contains representative immunoblots showing pVHL and HIF-1α levels in cells transfected with the indicated constructs. FIG. 13B shows results from a trans-well invasion assay of RCC4 (left panel, top) or RCC4/VHL (left panel, bottom) cells stably transfected with the indicated shRNAs or plasmids. The plot (right panel) shows the quantification of the area covered by the invasion cells, relative to the control. Results represent the means (±S.E.) of three independent experiments performed in triplicate. *P<0.05, ***P<0.001 versus control cells by one-way ANOVA. FIG. 13C shows the quantification of wound-healing assays of RCC4 or RCC4/VHL cell lines stably transfected with the indicated plasmids or shRNA. The left panel contains a graph plotting the means and s.d. of three independent experiments performed in triplicate. *, P<0.05, ***, P<0.001 versus control cells by one-way ANOVA. The right panel contains representative images of the assay. FIG. 13D shows the results from experiments in which RCC4 or RCC4/VHL cells were infected with the indicated constructs and HIF-1α activity was assayed by a HIF-1α luciferase reporter assay. The graph in the left panel shows the means (±S.E.) of three independent experiments performed in triplicate. *P<0.05, §§§§ P<0.0001 versus control cells by one-way ANOVA. The right panel contains representative immunoblots using the indicated antibodies.

FIGS. 14A-14G demonstrate that WSB1 promotes cancer cell invasion, migration, and metastasis by enhancing HIFs. FIG. 14A contains representative immunoblots for cells transduced with or without the indicated viral vectors. FIG. 14B is a graph plotting the results of a trans-well invasion assay for 786-O or 786-O/VHL cells stably expressing the indicated shRNAs or plasmids. The graph shows quantification of the area covered by the invasion cells, relative to the control. Results represent the means (±S.E.) of three independent experiments performed in triplicate. **P<0.01 versus vector virus injected cells; *P<0.05 versus control shRNA infected cells by one-way ANOVA. FIG. 14C is a graph plotting the quantification of wound-healing assays using 786-O or 786-O/VHL cell lines stably transfected with the indicated plasmids or shRNA. The mean and s.d. of one representative experiment, out of three independent experiments performed in triplicate, are shown (*P<0.001 versus vector virus injected cells by one-way ANOVA). FIG. 14D contains representative images from the experiments quantified in the graph of FIG. 14C. For FIGS. 14E and 14F, lentiviral-driven shRNA was used to deplete endogenous WSB1 from MDA-MB-231 cells, which were then rescued with an RNAi-resistant WSB1 (Wt or ΔSOCS). FIG. 14E is a graph plotting HIF-1α activity in the cells. Results represent the means (±S.E.) of three independent experiments performed in triplicate. *P<0.001 versus control shRNA virus infected cells; ****P<0.0001 versus WSB1 shRNA infected cells by one-way ANOVA. FIG. 14F contains representative immunoblots for cells transfected with the indicated constructs and then immunoblotted for the indicated proteins. FIG. 14G contains representative images from wound healing experiments in which lentiviral-driven shRNA was used to deplete endogenous WSB1 from RCC4/VHL cells, which were then rescued with an RNAi-resistant WSB1 (Wt or ΔSOCS).

FIGS. 16A-16C contain results from lung or liver colonization assays of mice that were intravenously injected with B16F10 cells stably infected with the indicated viral construct or shRNA. In particular, FIG. 16A contains representative images of from lung and liver, FIG. 16B contains a pair of graphs plotting the number of metastatic foci per lung (left) or liver (right) section, and FIG. 16C contains representative immunoblots. *P<0.05, P<0.01, *P<0.001 versus control cells by one-way ANOVA. FIG. 16D is a series of graphs plotting the quantity of pVHL-positive cells in slides from human patients with non-small cell lung cancer (NSCLC) adenocarcinoma, NSCLC squamous cell carcinoma, metastatic colorectal cancer, and metastatic breast cancer, based on high or low WSB1 expression. P values were calculated by Student's t-test. FIG. 16E is a schematic model.

FIG. 17A shows representative immunostaining intensities: 0 (negative), 1+ (weak), 2+ (moderate), and +3 (strong). FIG. 17B contains representative IHC images of WSB1 and pVHL in adenocarcinoma and squamous cell carcinoma, compare with normal lung tissues. Serial tumor sections from the same patient were processed.

DETAILED DESCRIPTION

Figure 1B:
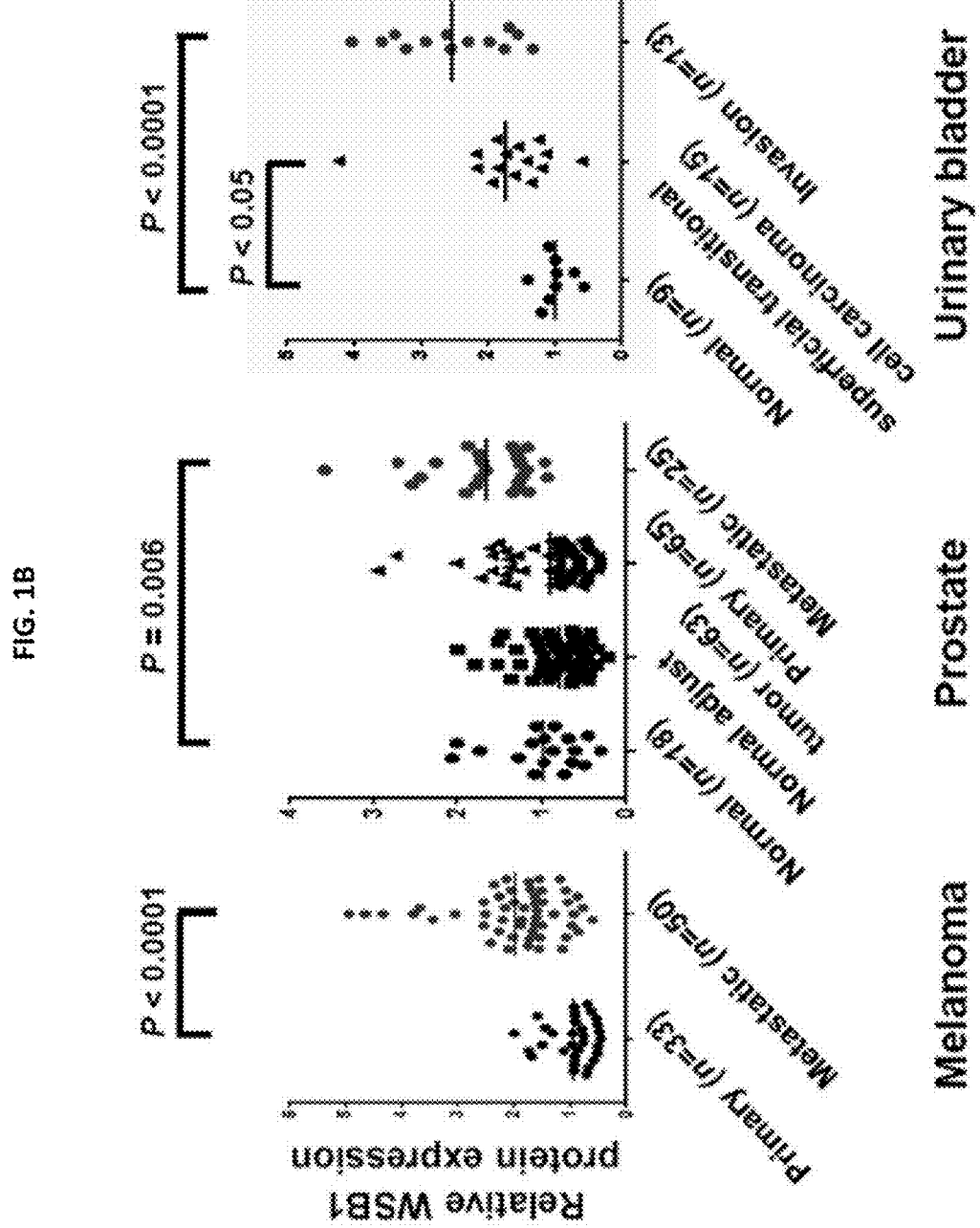
Figure 1C:
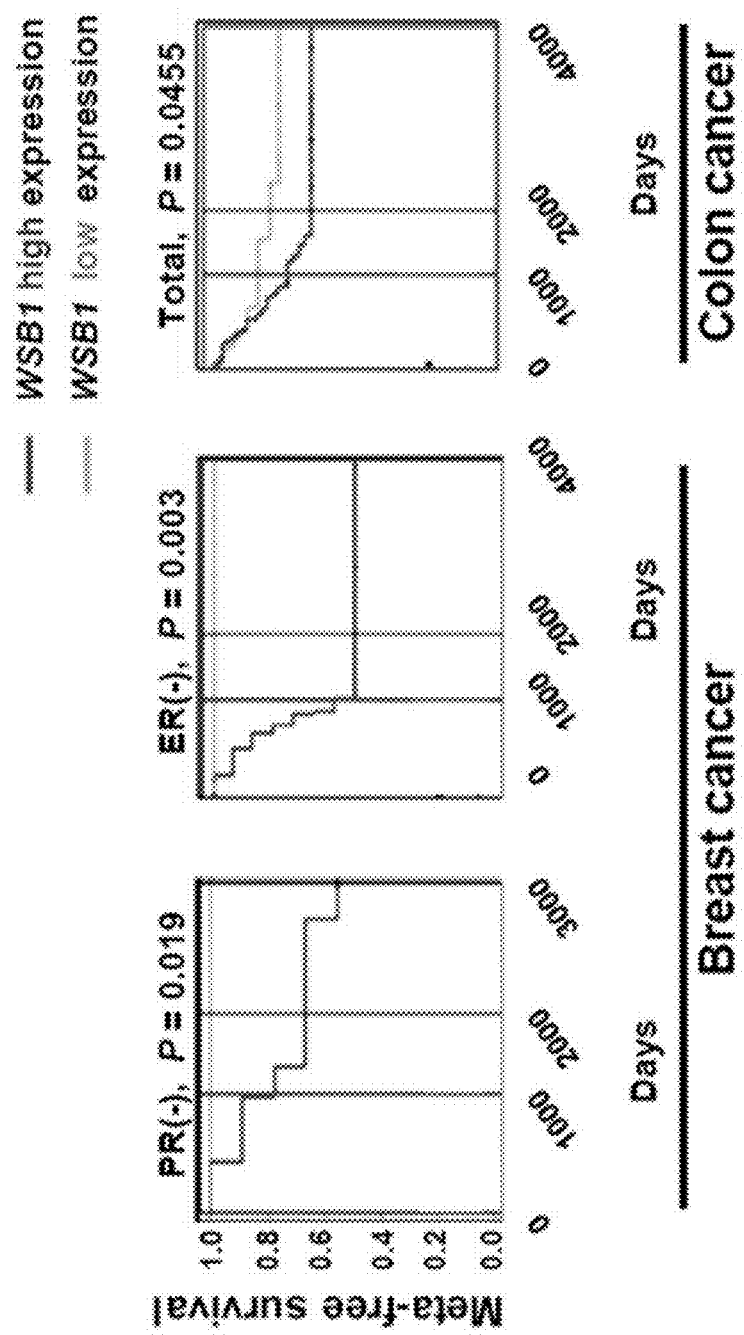

This document is based, at least in part, on the discoveries that WSB1 acts as an E3 ligase for pVHL, promotes HIF stabilization under both of normoxia and hypoxia conditions, is upregulated in human cancers and associated with poor prognosis, and promotes cancer cell invasion metastasis through the pVHL-HIF pathway. These discoveries are described in further detail in the Examples below. Given these discoveries, this document provides materials and methods that can be used to treat cancer and reduce metastasis by inhibiting the activity of WSB1, increasing the activity of pVHL, or both.

WSB1 is a member of the WD-protein subfamily, containing several WD-repeats spanning most of the protein and a SOCS box in the C-terminal region. The human WSB1 protein has the amino acid sequence:

```
                                              (SEQ ID NO: 1)
MASFPPRVNEKEIVRLRTIGELLAPAAPFDKKCGRENWTVAFAPDGSYFA

WSQGHRTVKLVPWSQCLQNFLLHGTKNVTNSSSLRLPRQNSDGGQKNKPR

EHIIDCGDIVWSLAFGSSVPEKQSRCVNIEWHRFRFGQDQLLLATGLNNG

RIKIWDVYTGKLLLNLVDHTEVVRDLTFAPDGSLILVSASRDKTLRVWDL

KDDGNMMKVLRGHQNWVYSCAFSPDSSMLCSVGASKAVFLWNMDKYTMIR

KLEGHHHDVVACDFSPDGALLATASYDTRVYIWDPHNGDILMEFGHLFP

PPTPIFAGGANDRWVRSVSFSHDGLHVASLADDKMVRFWRIDEDYPVQVA

PLSNGLCCAFSTDGSVLAAGTHDGSVYFWATPRQVPSLQHLCRMSIRRVM

PTQEVQELPIPSKLLEFLSYRI (NCBI Reference NP_056441),
``` and is encoded by the nucleotide sequence:

```
                                              (SEQ ID NO: 2)
agatatctccggcgccgcccgccattttgactccagtgtctcgtttgcag tcggcgctttaggggaactgtcttcctccgcaggcgcgaggctgggtaca gggtctattgtctgtggttgactccgtactttggtctgaggccttcggga gctttccgaggcagttagcagaagccgcagcggccgcccccgcccgtct cctctgtccctgggcccggggggaccaacttggcgtcacgcccctcagc ggtcgccactctcttctctgttgtttgggtccgcatcgtattcccggaatc agacggtgccccatagatggccagctttcccccgagggtcaacgagaaag agatcgtgagattacgtactataggtgaacttttagctcctgcagctcct tttgacaagaaatgtggtcgtgaaaattggactgttgcttttgctccaga tggttcatactttgcttggtcacaaggacatcgcacagtaaagcttgttc cgtggtcccagtgccttcagaactttctcttgcatggcaccaagaatgtt
``` accaattcaagcagtttaagattgccaagacaaaatagtgatggtggtca gaaaaataagcctcgtgaacatattatagactgtggagatatagtctgga gtcttgcttttgggtcatcagttccagaaaaacagagtcgctgtgtaaat atagaatggcatcgcttcagatttggacaagatcagctacttcttgctac agggttgaacaatgggcgtatcaaaatatgggatgtatatacaggaaaac tcctccttaacttggtagatcatactgaagtggtcagagatttaacttt gctccagatggaagcttgatcctggtgtcagcttcaagagacaaaactct cagagtatgggacctgaaagatgatggaaacatgatgaaagtattgaggg ggcatcagaattgggtgtacagctgtgcattctctcctgactcttctatg ctgtgttcagtcggagccagtaaagcagttttcctttggaatatggataa atacaccatgatacggaaactagaaggacatcaccatgatgtggtagctt gtgacttttctcctgatggagcattactggctactgcatcttatgatact cgagtatatatctgggatccacataatggagacattctgatggaatttgg gcacctgttttcccccacctactccaatatttgctggaggagcaaatgacc ggtgggtacgatctgtatcttttagccatgatggactgcatgttgcaagc cttgctgatgataaaatggtgaggttctggagaattgatgaggattatcc agtgcaagttgcacctttgagcaatggtctttgctgtgccttctctactg atggcagtgttttagctgctgggacacatgacggaagtgtgtattttgg gccactccacggcaggtccctagcctgcaacatttatgtcgcatgtcaat ccgaagagtgatgcccacccaagaagttcaggagctgccgattccttcca agcttttggagtttctctcgtatcgtatttagaagattctgccttccta gtagtagggactgacagaatacacttaacacaaacctcaagctttactga cttcaattatctgttttttaaagacgtagaagatttatttaatttgatatg ttcttgtactgcattttgatcagttgagcttttaaaatatattatataga caatagaagtatttctgaacatatcaaatataaatttttttaaagatcta actgtgaaaacatacatacctgtacatatttagatataagctgctatatg ttgaatggaccctttgcttttctgattttagttctgacatgtatatat tgcttcagtagagccacaatatgtatctttgctgtaaagtgcaaggaaat tttaaattctgggacactgagttagatggtaaatactgacttacgaaagt tgaattgggtgaggcgggcaaatcacctgaggtcagcagtttgagactag cctggcaaacatgatgaaaccctgtctctactaaaaatacaaaaaaaaaa aaaattagccaggcgtggtggtgcacacctgtagtcctagctacttggga ggctgaggcaggagaattgcttgaacccaggaggtggaggttgcagtaag ccaagatcacaccactgcactccaacctggacaacagagcgagactccat ctcaaaaaaaaaaaaaaattgtgttgcctcatacgaaatgtatttggttt tgttggagagtgtcagactgatctggaagtgaaacacagtttatgtacag ggaaaaggattttattatcttaggaatgtcatccaagacgtagagcttg aatgtgacgttatttaaaaacaacaacaaagaaggcagagccaggatata actagaaaaggatgtctttttttttttttttactccccctctaaacact gctgctgccttaatttagaaagcagcttactagtttaccatgtggtata -continued

```
aagtattataaattgttgtgaatttgaagaatccgtctactgtattattg ctaaatattttgtttatactaagggacaattattttaagaccatggattt aaaaaaaaaaaaaaaactctgtttctgcaggggatgatattggtgagtt gccaaagaagcaatacagcatatctgatttgccttctgttgtttatctta cctgcagatattaagaatgtatgcattatgtaaaatgctcaattatatat ttttgttgagttttttaattaaagacttgttaaaaaaaaaaaaaaa
```

(NCBI Reference NM_015626).

pVHL has ubiquitin ligase E3 activity, and is a component of a protein complex that includes elongin B, elongin C, and cullin-2. The complex is involved in the ubiquitination and degradation of hypoxia-inducible factor (HIF), which is a transcription factor that plays a central role in the regulation of gene expression by oxygen. The human pVHL protein has the amino acid sequence:

(SEQ ID NO: 3)
MPRRAENWDEAEVGAEEAGVEEYGPEEDGGEESGAEESGPEESGPEELGA

EEEMEAGRPRPVLRSVNSREPSQVIFCNRSPRVVLPVWLNFDGEPQPYPT

LPPGTGRRIHSYRGHLWLFRDAGTHDGLLVNQTELFVPSLNVDGQPIFAN

ITLPVYTLKERCLQVVRSLVKPENYRRLDIVRSLYEDLEDHPNVQKDLER

LTQERIAHQRMGD (NCBI Reference NP_000542.1), and is encoded by the nucleotide sequence:

(SEQ ID NO: 4)
```
cctcgcctccgttacaacggcctacggtgctggaggatccttctgcgcac gcgcacagcctccggccggctatttccgcgagcgcgttccatcctctacc gagcgcgcgcgaagactacggaggtcgactcgggagcgcgcacgcagctc cgccccgcgtccgaccgcggatcccgcggcgtccggcccgggtggtctg gatcgcggagggaatgccccggagggcggagaactgggacgaggccgagg taggcgcggaggaggcaggcgtcgaagagtacggccctgaagaagacggc ggggaggagtcgggcgccgaggagtccggcccggaagagtccggcccgga ggaactgggcgccgaggaggagatggaggccgggcggccgcgccccgtgc tgcgctcggtgaactcgcgcgagccctcccaggtcatcttctgcaatcgc agtccgcgcgtcgtgctgcccgtatggctcaacttcgacggcgagccgca gccctacccaacgctgccgcctggcacgggccgccgcatccacagctacc gaggtcacctttggctcttcagagatgcagggacacacgatgggcttctg gttaaccaaactgaattatttgtgccatctctcaatgttgacggacagcc tatttttgccaatatcacactgccagtgtatactctgaaagagcgatgcc tccaggttgtccggagcctagtcaagcctgagaattacaggagactggac atcgtcaggtcgctctacgaagatctggaagaccacccaaatgtgcagaa agacctggagcggctgacacaggagcgcattgcacatcaacggatgggag attgaagatttctgttgaaacttacactgtttcatctcagcttttgatgg tactgatgagtcttgatctagatacaggactggttccttccttagtttca aagtgtctcattctcagagtaaaataggcaccattgcttaaaagaaagtt aactgacttcactaggcattgtgatgtttaggggcaaacatcacaaaatg taatttaatgcctgcccattagagaagtatttatcaggagaaggtggtgg cattttgcttcctagtaagtcaggacagcttgtatgtaaggaggtttgt ataagtaattcagtgggaattgcagcatatcgtttaattttaagaaggca ttggcatctgcttttaatggatgtataatacatccattctacatccgtag cggttggtgacttgtctgcctcctgctttgggaagactgaggcatccgtg aggcagggacaagtctttctcctctttgagaccccagtgcctgcacatca tgagccttcagtcagggtttgtcagaggaacaaaccaggggacactttgt tagaaagtgcttagaggttctgcctctattttttgttgggggggtgggagag gggaccttaaaatgtgtacagtgaacaaatgtcttaaagggaatcatttt tgtaggaagcattttttataattttctaagtcgtgcactttctcggtcca ctcttgttgaagtgctgttttattactgtttctaaactaggattgacatt ctacagttgtgataatagcattttttgtaacttgccatccgcacagaaaat acgagaaaatctgcatgtttgattatagtattaatggacaaataagtttt tgctaaatgtgagtatttctgttccttttttgtaaatatgtgacattcctg attgatttgggtttttttgttgttgttgttttgttttgttttgtttttt gagatggagtctcactcttgtcacccaggctggagtgcagtggcgccatc tcggctcactgcaacctctgcctcctgggttcacgtaatcctcctgagta gctgggattacaggcgcctgccaccacgctggccaattttttgtactttta gtagagacagtgtttcgccatgttggccaggctggtttcaaactcctgac ctcaggtgatccgcccacctcagcctcccaaaatggtgggattacaggtg tgtgggccaccgtgcctggctgattcagcattttttatcaggcaggacca ggtggcacttccacctccagcctctggtcctaccaatggattcatggagt agcctggactgtttcatagttttctaaatgtacaaattcttataggctag acttagattcattaactcaaattcaatgcttctatcagactcagtttttt gtaactaatagatttttttttccacttttgttctactccttccctaatag cttttttaaaaaaatctccccagtagagaaacatttggaaaagacagaaaa ctaaaaaggaagaaaaaagatccctattagatacacttcttaaatacaat cacattaacattttgagctatttccttccagccttttttagggcagatttt ggttggttttacatagttgagattgtactgttcatacagttttatacccc ttttcatttaactttataacttaaatattgctctatgttagtataagct tttcacaaacattagtatagtctcccttttataattaatgtttgtgggta tttcttggcatgcatcttttaattccttatcctagccttttgggcacaattc ctgtgctcaaaatgagagtgacggctggcatggtggctcccgcctgtaa tcccagtactttggaaagccaaggtaagaggattgcttgagcccagaact tcaagatgagcctgggctcatagtgagaaccccatctatacaaaaaattttt taaaaattagcatggcggcacacatctgtaatcctagctacttggcaggc tgaggtgagaagatcattggagtttaggaattggaggctgcagtgagcca tgagtatgccactgcactccagcctggggacagagcaagaccctgcctc aaaaaaaaaaaaaaaaaaaatcaggccgggcatggtggctcacgcctg taatcccagcactttgggaggtcgaggtgggcagatcacctgaggtcagg
```

-continued
```
agttcgagaccagcctggccaacatggtaaaacccatttctactaaaaa atacaagaattagctgggtgtggtggcgcatgcctgtaatcctagctact caggaggctgaggcaggagaatcacttgaacccaggaggcgaagattgca gtgagctgatatcgcaccattgtactccagcctgtgtgacagagcaatac tatgtctcaaaaaaaaaaaaaattcaaatcagagtgaagtgaatgagac actccagttttccttctactccgaatttcaactgattttagctcctcatt caacattcaacaaatagtctttttttttttttttttatttttttttgag atggagtctcactctgttgcccaggctggagtgcagtggtgcgatctctg ctcactacaagctctgcctcccgagttcaagtgattctcctggctcaccc tcctgagtagctgggattacaggcgcctgccaccatgcctggctaatttt gtgttttagtggagacggggtttcaccatgttgtccaggatggtcttga tctcctgaccttgtgatccacccacctcagcctcccaaagtgctgggatt acaggtgtgagccaccgcgtccagccagattattattttttttaagctgt attgtgtcaaaatgatagttcatgctcctatgttaaaacctgcaggccga gcacagtggctcatgcctgtaatcccagcattttgggagaccaaggcgga tggatcacctgaggtcaggagctgaagaccagcctggctaacatggtgaa acctcatctccacttaaaatacaaaaattgccggccgcggcggctcatgc ctgtaatcccagcactttgggaggcctaggcgggtggatcacgaggtcag gaaatcgagaccatcctggctaacacgggtgaaacccgtctctattaaa aaatagaaaaattaggcgggcgtggtggtgagcgcctgtagtcccagct actcgagagcctgaggcaggagaatggcatgaacctggaaggcggagctt gcagtgagctgagatggtgccactgcactctaacctgggcgacagagtga gacaccgtctcaaaaaaaaaaacaaaaaacaaaaattatccaggtgtggc ggtgggcgcctgtgaggcaggcgaatctcttgaacccgggaggcggaggt tgcagtgagccaagatcacaccattgcactccagcctgggcaacaagagt gaaattccatctcaaaaagaaaccaaaaaaacaaaaaaaaaacatgccgt ttgagtactgtgttttttggtgttgtccaaggaaaattaaaaacctgtagc atgaataatgtttgtttttcatttcgaatcttgtgaatgtattaaatata tcgctcttaagagacggtgaagttcctatttcaagtttttttttttttt ttttttttaaagctgtttttttaatacattaaatggtgctgagtaaaggaa atag (NCBI Reference NM_000551).
```

In some embodiments, this document provides agents that can reduce the activity of WSB1. An agent can be targeted to WSB1 to inhibit its activity by, for example, reducing expression of WSB1 protein, or by reducing the activity of WSB1 protein that is expressed. Examples of such agents may include small molecules and inhibitory nucleic acids (e.g., siRNA, miRNA, shRNA molecules, and antisense oligonucleotides). For example, small molecules targeting the WD40 and/or SOCS domain of WSB1 may be particularly useful. Antagonistic antibodies that bind to WSB1 also may be useful as agents for reducing WSB1 activity. Methods for obtaining and testing the activities of such agents include those known in the art.

In some embodiments, this document provides agents that can increase the activity of pVHL. An agent can be targeted to pVHL to increase its activity by, for example, increasing the expression of pVHL protein, or by increasing the activity or stability of pVHL protein that is expressed. Examples of such agents may include small molecules, nucleic acids encoding pVHL, and pVHL polypeptides themselves. Agonistic antibodies that bind to pVHL also may be useful as agents for increasing pVHL activity. Again, methods for obtaining and testing the activities of such agents include those known in the art.

For example, methods of screening for small molecule inhibitors or activators (antagonists or agonists) of polypeptides such as WSB1 or pVHL1 are known in the art. In some embodiments, for example, cells can be cultured with one or more candidate small molecules, and the effect on WSB1 or pVHL expression, stability, or activity can be assessed using techniques such as northern blotting, Western blotting, or other immunological methods.

Methods for designing and making inhibitory nucleic acids also are known in the art. Such agents can reduces the level of mRNA that encodes a WSB1 polypeptide. For example, a WSB1 antagonist can be an agent that reduces transcription of nucleic acid encoding a WSB1 polypeptide, or promotes degradation of mRNA encoding a WSB1 polypeptide (e.g., by RNA interference (RNAi)), or inhibits posttranscriptional processing (e.g., splicing or nuclear export) of mRNA encoding a WSB1 polypeptide. Such an agent can inhibit protein synthesis from WSB1 mRNA (e.g., by RNAi), or promote degradation of WSB1 protein, thereby reducing the level of WSB1 polypeptide in a subject. Small interfering RNA (siRNA) molecules can be synthesized in vitro or made from a DNA vector in vivo. In some cases, a siRNA molecule can contain a backbone modification to increase its resistance to serum nucleases and increase its half-life in the circulation. Such modification can be made as described elsewhere (Chiu et al., *RNA* 2003, 9:1034-1048; and Czauderna et al., *Nucleic Acids Res* 2003, 31:2705-2716). In some cases, a small hairpin RNA (shRNA, which can be converted to a siRNA) can be used as a WSB1 antagonist.

Methods for making antibodies having specific binding affinity for a WSB1 or pVHL polypeptide can include recombinant production of the polypeptide, purification of the polypeptide from a biological sample (e.g., a heterologous expression system), or chemical synthesis of the polypeptide. For example, a polypeptide having the amino acid sequence set forth in SEQ ID NO:1 or SEQ ID NO:3, or a fragment thereof that is at least six amino acids in length, can be used to immunize an animal. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Monoclonal antibodies can be prepared using a polypeptide provided herein and standard hybridoma technology. In particular, monoclonal antibodies can be obtained by any technique that provides for the production of antibody molecules by continuous cell lines in culture such as described by Kohler et al., *Nature*, 256:495 (1975), the human B-cell hybridoma technique (Kosbor et al., *Immunology Today*, 4:72 (1983); Cole et al., *Proc. Natl. Acad. Sci. USA*, 80:2026 (1983)), and the EBV-hybridoma technique (Cole et al., "Monoclonal Antibodies and Cancer Therapy," Alan R. Liss, Inc., pp. 77-96 (1983)). Such antibodies can be of any immunoglobulin class including IgG, IgM, IgE, IgA, IgD, and any subclass thereof. The hybridoma producing the monoclonal antibodies can be cultivated in vitro and in vivo.

This document also provides methods and materials related to identifying agonists or antagonists of WSB1-mediated ubiquitination of pVHL. For example, this document provides methods and materials for using WSB1 polypeptides and pVHL polypeptides (e.g., ubiquitinated pVHL polypeptides) to identify agents that increase or decrease the effects of the WSB1 polypeptides on the pVHL polypeptides. In some cases, the stability of ubiquitinated pVHL polypeptides treated with WSB1 polypeptides in the presence and absence of a test agent can be assessed to determine whether or not the test agent increases or decreases the stability of the ubiquitinated pVHL polypeptides. An agent that increases the stability of the ubiquitinated pVHL polypeptides in a manner dependent on the WSB1 polypeptide can be an antagonist of WSB1-mediated action on pVHL polypeptides, and an agent that decreases the stability of the ubiquitinated pVHL polypeptides in a manner dependent on the WSB1 polypeptide can be an agonist of WSB1-mediated action on pVHL polypeptides. The stability of ubiquitinated pVHL polypeptides can be assessed using polypeptide assays capable of detecting intact full-length polypeptide or degraded polypeptides, for example. Agonists and antagonists also can be identified by screening test agents (e.g., from synthetic compound libraries and/or natural product libraries). Test agents can be obtained from any commercial source and can be chemically synthesized using methods that are known to those of skill in the art. Test agents can be screened and characterized using in vitro cell-based assays, cell free assays, and/or in vivo animal models.

Methods of making nucleic acids, including inhibitory nucleic acids, are known in the art. As used herein, the term "nucleic acid" refers to both RNA and DNA, including mRNA, cDNA, genomic DNA, synthetic (e.g., chemically synthesized) DNA, and nucleic acid analogs. A nucleic acid can be double-stranded or single-stranded, and where single-stranded, can be the sense strand or the antisense strand. In addition, nucleic acid can be circular or linear. Nucleic acid analogs can be modified at the base moiety, sugar moiety, or phosphate backbone to improve, for example, stability, hybridization, or solubility of a nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone and the four bases are retained. See, for example, Summerton and Weller, *Antisense Nucleic Acid Drug Dev* 7:187-195, 1997; and Hyrup et al. *Bioorgan Med Chem* 4:5-23, 1996. In addition, the deoxyphosphate backbone can be replaced with, for example, a phosphorothioate or phosphorodithioate backbone, a phosphoroamidite, or an alkyl phosphotriester backbone.

An isolated nucleic acid as provided herein can comprise or consist of a sequence that encodes the amino acid sequence set forth in SEQ ID NO:3, for example, or a portion thereof. In some embodiments, such a nucleic acid can contain the human nucleic acid sequence set forth in SEQ ID NO:4.

Typically, an isolated nucleic acid is at least 10 nucleotides in length (e.g., 10 to 100, 15 to 150, 20 to 200, 25 to 250, 30 to 300, 40 to 400, 50 to 500, 75 to 750, 100 to 1000, or more than 1000 nucleotides in length). Nucleic acid molecules that are less than full-length can be useful, for example, as primers or probes for diagnostic purposes. Isolated nucleic acid molecules can be produced by standard techniques, including, without limitation, common molecular cloning and chemical nucleic acid synthesis techniques. For example, polymerase chain reaction (PCR) techniques can be used. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 15 to 50 nucleotides in length, but can range from 10 nucleotides to hundreds of nucleotides in length. For example, a primer can be 12, 15, 16, 17, 18, 19, 20, 21, 22, 23, 24, 25, 26, 27, 28, 29, 30, 35, 40, or 45 nucleotides in length. A primer can be purified from a restriction digest by conventional methods, or can be chemically synthesized. Primers typically are single-stranded for maximum efficiency in amplification, but a primer can be double-stranded. Double-stranded primers are first denatured (e.g., treated with heat) to separate the strands before use in amplification. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids as described elsewhere (Lewis, *Genetic Engineering News* 12(9):1, 1992; Guatelli et al., *Proc Natl Acad Sci USA* 87:1874-1878, 1990; and Weiss, *Science* 254:1292, 1991).

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

As used herein, a "vector" is a replicon, such as a plasmid, phage, or cosmid, into which another DNA segment can be inserted so as to bring about the replication of the inserted segment. A vector can be an expression vector. An "expression vector" is a vector that includes one or more expression control sequences, and an "expression control sequence" is a DNA sequence that controls and regulates the transcription and/or translation of another DNA sequence.

In an expression vector provided herein, the nucleic acid can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it can be necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the polypeptide encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, poxviruses, adenoviruses, and adeno-associated viruses. Numerous vectors and expression systems are commercially available from such corporations as Novagen (Madison, Wis.), Clontech Laboratories (Mountain View, Calif.), Stratagene (La Jolla, Calif.), and Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or FLAG™ tag (Kodak, New Haven, Conn.) sequences typically are expressed as a fusion with the encoded polypeptide. Such tags can be inserted anywhere within the polypeptide including at either the carboxyl or amino terminus.

This document also provides host cells containing a nucleic acid molecule and/or nucleic acid vector as described herein. The term "host cells" refers to prokaryotic cells and eukaryotic cells into which a nucleic acid molecule or vector can be introduced. Any method can be used to introduce nucleic acid into a cell. For example, calcium phosphate precipitation, electroporation, heat shock, lipofection, microinjection, and viral-mediated nucleic acid transfer can be used introduce nucleic acid into cells. In addition, naked DNA can be delivered directly to cells in vivo as described elsewhere (U.S. Pat. Nos. 5,580,859 and 5,589,466).

Interfering RNA molecules can be effective in suppressing accumulation of mRNAs and the polypeptides that they encode. A "small interfering RNA" or "short interfering RNA" (siRNA) or "short hairpin RNA" (shRNA) is a double-stranded RNA molecule that is complementary to a target nucleic acid sequence. A double-stranded RNA molecule can be formed by complementary pairing between a first RNA portion and a second RNA portion. The length of each portion generally is less than 30 nucleotides in length (e.g., 25 to 30, 20 to 25, 15 to 20, or 10 to 15 nucleotides). In some embodiments, for example, the length of each portion can be 19 to 25 nucleotides. In some siRNA molecules, the complementary first and second portions of the RNA molecule are the "stem" of a hairpin structure. The two portions can be joined by a linking sequence, which can form a "loop" in the hairpin structure. The linking sequence can vary in length. In some embodiments, the linking sequence can be 5 to 8, 6 to 9, 7 to 10, 8 to 11, 9 to 12, or 10 to 13 nucleotides in length. The first and second portions are complementary but may not be completely symmetrical, as the hairpin structure may contain 3' or 5' overhang nucleotides (e.g., a 1, 2, 3, 4, or 5 nucleotide overhang).

Methods for identifying target sequences and generating interfering RNAs targeted to those sequences include techniques known in the art, for example. siRNA-mediated suppression of nucleic acid expression is specific, as even a single base pair mismatch between siRNA and the targeted nucleic acid can abolish the action of RNA interference. It is noted that certain embodiments of inhibitory nucleic acids against WSB1 are described in the Examples below.

One or more agents that modulate the levels or activity of WSB1 and/or pVHL can be incorporated into a composition for administration to a mammal (e.g., a research animal or a human patient diagnosed as having cancer). For example, an agent or molecule that leads to reduced WSB1 levels or increased pVHL levels as described herein can be admixed, encapsulated, conjugated or otherwise associated with other molecules, molecular structures, or mixtures of compounds such as, for example, liposomes, receptor or cell targeted molecules, or oral, topical or other formulations for assisting in uptake, distribution and/or absorption.

In some cases, a composition can contain one or more agents targeted to WSB1 or pVHL in combination with a pharmaceutically acceptable carrier. Pharmaceutically acceptable carriers include, for example, pharmaceutically acceptable solvents, suspending agents, or any other pharmacologically inert vehicles for delivering compounds to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Exemplary pharmaceutically acceptable carriers include, without limitation: water, saline solution, binding agents (e.g., polyvinylpyrrolidone or hydroxypropyl methylcellulose), fillers (e.g., lactose or dextrose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). In some embodiments, for example, an agent that modulates the level or activity of WSB1 and/or pVHL can be combined with a physiological salt solution such as 0.9% sodium chloride, or an isotonic aqueous solution of sodium phosphate buffered to a pH of 7.4.

The methods provided herein can include administering to a mammal (e.g., a human or a non-human mammal) an agent that modulates the level or activity of WSB1 and/or pVHL (e.g., an agent that decreases the level or activity of WSB1, or that increases the level or activity of pVHL), under conditions such that the administration is therapeutically effective against the development or progression of cancer. As used herein, "therapeutically effective" refers to a reduction in one or more symptoms of cancer, or a reduction in or prevention of cancer progression (e.g., metastasis). Compositions containing one or more agents as described herein can be given once or more daily, weekly, monthly, or even less often, or can be administered continuously for a period of time (e.g., hours, days, or weeks). In some cases, preparations can be designed to stabilize such agents and maintain effective activity in a mammal for several days.

Pharmaceutical compositions containing one or more agents that modulate WSB1 and/or pVHL as described herein can be administered by a number of methods, depending upon whether local or systemic treatment is desired and upon the area to be treated. Administration of the agents and compositions provided herein can be, for example, oral or parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). For treating tissues in the central nervous system, an agent or composition can be administered by injection or infusion into the cerebrospinal fluid, typically with one or more agents capable of promoting penetration of the polypeptides across the blood-brain barrier.

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders. Compositions and formulations for parenteral, intrathecal or intraventricular administration can include sterile aqueous solutions, which also can contain buffers, diluents and other suitable additives (e.g., penetration enhancers, carrier compounds and other pharmaceutically acceptable carriers).

Pharmaceutical compositions include, without limitation, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations have been widely used for oral delivery of therapeutics due to their ease of formulation and efficacy of solubilization, absorption, and bioavailability.

Liposomes are vesicles that have a membrane formed from a lipophilic material and an aqueous interior that can contain the composition to be delivered. Liposomes can be particularly useful due to their specificity and the duration of action they offer from the standpoint of drug delivery. Liposome compositions can be formed, for example, from phosphatidylcholine, dimyristoyl phosphatidylcholine, dipalmitoyl phosphatidylcholine, dimyristoyl phosphatidylglycerol, or dioleoyl phosphatidylethanolamine. Numerous lipophilic agents are commercially available, including LIPOFECTIN® (Invitrogen/Life Technologies, Carlsbad, Calif.) and EFFECTENE™ (Qiagen, Valencia, Calif.).

The agents and compositions useful in the methods provided herein can further encompass any pharmaceutically acceptable salts, esters, or salts of such esters, or any other compound which, upon administration to an animal including a human, is capable of providing (directly or indirectly) the biologically active metabolite or residue thereof. Accordingly, for example, this document provides pharmaceutically acceptable salts of agents that modulate the levels or activity of WSB1 and/or pVHL, prodrugs and pharmaceutically acceptable salts of such prodrugs, and other bioequivalents. The term "prodrug" indicates a therapeutic agent that is prepared in an inactive form and is converted to an active form (i.e., drug) within the body or cells thereof by the action of endogenous enzymes or other chemicals and/or conditions. The term "pharmaceutically acceptable salts" refers to physiologically and pharmaceutically acceptable salts of the agents provided herein (i.e., salts that retain the desired biological activity of the agent without imparting undesired toxicological effects). Examples of pharmaceutically acceptable salts include, but are not limited to, salts formed with cations (e.g., sodium, potassium, calcium, or polyamines such as spermine); acid addition salts formed with inorganic acids (e.g., hydrochloric acid, hydrobromic acid, sulfuric acid, phosphoric acid, or nitric acid); and salts formed with organic acids (e.g., acetic acid, citric acid, oxalic acid, palmitic acid, or fumaric acid).

Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions provided herein, such as dyes, flavoring agents, preservatives, antioxidants, opacifiers, thickening agents and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, and aromatic substances. When added, however, such materials should not unduly interfere with the biological activities of the WSB1- and/or pVHL-modulating agents within the compositions provided herein. The formulations can be sterilized if desired.

The pharmaceutical formulations, which can be presented conveniently in unit dosage form, can be prepared according to conventional techniques well known in the pharmaceutical industry. Such techniques include the step of bringing into association the active ingredients with the desired pharmaceutical carrier(s) or excipient(s). Typically, the formulations can be prepared by uniformly and bringing the active ingredients into intimate association with liquid carriers or finely divided solid carriers or both, and then, if necessary, shaping the product. Formulations can be sterilized if desired, provided that the method of sterilization does not interfere with the effectiveness of the polypeptide contained in the formulation.

The compositions described herein can be formulated into any of many possible dosage forms such as, but not limited to, tablets, capsules, liquid syrups, soft gels, suppositories, and enemas. The compositions also can be formulated as suspensions in aqueous, non-aqueous or mixed media. Aqueous suspensions further can contain substances that increase the viscosity of the suspension including, for example, sodium carboxymethylcellulose, sorbitol, and/or dextran. Suspensions also can contain stabilizers.

The agents and compositions described herein also can be combined with packaging material and sold as kits for treating cancer. Components and methods for producing articles of manufacture are well known. The articles of manufacture may combine one or more of the agents and/or molecules provided herein. In addition, the article of manufacture further may include, for example, buffers or other control reagents for reducing or monitoring the symptoms of the cancer to be treated. Instructions describing how the agents and compositions are effective for reducing such symptoms can be included in such kits.

The invention will be further described in the following examples, which do not limit the scope of the invention described in the claims.

EXAMPLES

Example 1—Materials and Methods

Cells, Cell Lines and Reagents:

All cell lines were sourced from commercial vendors. Human embryonic kidney (HEK) 293T, HEK 293, HeLa cervix carcinoma cells, RCC4, RCC4/VHL, 786-O, and 786-O/VHL human renal carcinoma cells were cultured in Dulbecco's modified Eagle's media (DMEM, Gibco-Invitrogen). Five human lung cancer lines (three adenocarcinoma—H522, H1650 and A549 and two large cell carcinoma—H460 and H1299), six human pancreatic cancer cell lines (BxPC3, Hup-T3, Mia-Paca, Panc1, Pan 04.03, and ASPC1), four human breast cancer cell lines (HT-29, HCC1937, HCC1806, and MDA231), and mouse melanoma B16F10 cells were maintained in Eagle's Minimal Essential Media (EMEM) or RPMI 1640 (Gibco-Invitrogen, Grand Island, N.Y.). All media contained 10% heat-inactivated FBS (Gibco-Invitrogen), sodium bicarbonate (2 mg/ml; Sigma-Aldrich, St Louis, Mo.), penicillin (100 units/ml), and streptomycin (100 µg/ml; Gibco-Invitrogen). N-carbobenzoxy-1-leucinylleucinyl-1-norleucinal (MG 132), cycloheximide (CHX), and $CoCl_2$ were purchased from Sigma-Aldrich.

In Vitro Assays:

After transfection with Myc or Myc-WSB1 (WT, ΔSOCS), cells were collected for immunoprecipitation and/or immunoblot analysis. After immunoprecipitation with Myc antibody for WSB1, samples were incubated with reaction buffer (50 mM Tris-HCl, pH 7.5, 2.5 mM $MgCl_2$, 0.05% Nonidet P-40, and 0.5 mM dithiothreitol), Flag- or Myc-ubiquitin (5 mM), ATP (2 mM), and substrates (e.g., recombinant VHL) at 32° C. for 90 minutes.

In Vivo Ubiquitination Assays:

For in vivo ubiquitination, cells were transfected with ubiquitin-His plasmid together with Myc, Myc-WSB1, or Myc-ΔSOCS, followed by treatment with MG 132 (10 µM). 48 hours post-transfection, cells were lysed with urea lysis buffer (8 M urea, 0.1 M $Na_2HPO_4$, 0.1 M Tris/HCl (pH 8.0), 0.05% Tween 20, and 0.01 M imidazole). After centrifugation, the supernatants were collected and incubated with 20 mL Ni-NTA agarose beads (Qiagen) for four hours at 4° C. The precipitates were washed three times with urea wash buffer (8 M urea, 0.1 M $Na_2HPO_4$, 0.1 M Tris/HCl (pH 8.0), 0.05% Tween 20, and 0.02 M imidazole) and native wash buffer (0.1 M $Na_2HPO_4$, 0.1 M Tris/HCl (pH 8.0), 0.05% Tween 20, and 0.02 M imidazole), and were boiled with SDS loading buffer and then subjected to SDS-PAGE followed by immunoblot analysis.

In Vitro Binding Assay:

GST fusion proteins were prepared following standard protocols. For in vitro binding assays, WSB1-(WT, ΔSOCS) GST fusion proteins bound to GSH Sepharose were incubated with cell lysates. After washing, the bound proteins were separated by SDS-PAGE and immunoblotted with antibodies as desired.

Statistical Analysis:

Each assay was performed in triplicate and independently repeated at least three times. Results are presented as mean±standard error of mean (SEM). Statistical analyses were performed using GraphPad Prism software (version 4.02; GraphPad Software, San Diego, Calif.). One-way analysis of variance (ANOVA) followed by T-test was used to compare the results. A difference was considered significant if $P<0.05$. Statistical significance was defined as $P<0.05$ (*), $P<0.01$(), and $P<0.001$(*).

Gene Expression Profiling from FF Primary Never Smoker Lung Adenocarcinoma Patients:

Gene expression profiling was described elsewhere (Jang et al., Clin Cancer Res 18:3658-3667, 2012). Briefly, after RNA extraction and gene expression profiling by microarray from 56 primary lung tumors, the data for mRNA was processed and normalized through BeadStudio software, version 3.0. (Illumina Inc.) using the quantile normalization method, and then log 2 transformed and analyzed using the Partek Genomics Suite (Partek Inc.). To identify differentially expressed genes, the one-way ANOVA model was applied for all analyses. mRNAs with a fold change>±1.5 at raw P value<0.01 and false discovery rate (FDR)<5% were considered significant. FF tumors were further subclassified into WSB1 "high (H)" and "low (L)" groups based on the means of expression after normalization, and mRNA expression was compared between WSB1-H and WSB1-L tumors. 2,534 mRNAs were found to be differentially expressed based on fold change>1.5 and FDR<5% using this analysis. These 2,534 genes were analyzed using Ingenuity Pathway Analysis (IPA) 8.5 software (Ingenuity Systems, CA) to identify their biological functions in lung adenocarcinoma potentially modified by WSB1 expression level.

Plasmids:

Myc-tagged WSB1 (empty and WT, ΔWD1-2, ΔWD1-3, ΔN, ΔSOCS, and ΔC) were provided by Dr. Cheol Yong Choi (Sungkyunkwan University, Korea). HA-tagged HIF-1α and HA-tagged VHL were obtained from Addgene.

Transient Transfection and Stable Transduction:

shRNAs were infected using LIPOFECTAMINE® 2000 reagent (Invitrogen). Human WSB1, mouse WSB1, HIF-1α, and HIPK2 were obtained from Sigma-Aldrich and Open Biosystems.

WSB1 shRNA (Human):

(SEQ ID NO: 5)
5'-TGCTGTTGACAGTGAGCGCGGAGTTTCTCTCGTATCGTATTAGTGA
AGCCACAGATGTAATACGATACGAGAGAAACTCCATGCCTACTGCCTCG
GA-3'

(SEQ ID NO: 6)
5'-TGCTGTTGACAGTGAGCGCGCTGTAAAGTGCAAGGAAATTTAGTG
AAGCCACAGATGTAAATTTCCTTGCACTTTACAGCATGCCTACTGCCTC
GGA-3'

WSB1 shRNA (Mouse):

(SEQ ID NO: 7)
5'-ACATGAGCTGCTGCTATATAT-3'

(SEQ ID NO: 8)
5'-GCTTACTCCTTGTATCAGCTT-3'

HIF-1a shRNA (mouse)

(SEQ ID NO: 9)
5'-GTGATGAAAGAATTACCGAAT-3'

(SEQ ID NO: 10)
5'-TGCTCTTTGTGGTTGGATCTA-3'

HIPK2 shRNA (mouse)

(SEQ ID NO: 11)
5'-GCTGTTGACAGTGAGCGACGAGTCAGTATCCAGCCCAATTAGTGAA
GCCACAGATGTAATTGGGCTGGATACTGACTCGGTGCCTACTGCCTCGG
A-3'

(SEQ ID NO: 12)
5'-GCTGTTGACAGTGAGCGAGGAGAGTGCCGATGACTATAATAGTGAA
GCCACAGATGTATTATAGTCATCGGCACTCTCCGTGCCTACTGCCTCGG
A-3'

For transient overexpression studies, DNA plasmids were transfected using the LIPOFECTAMINE® 2000 reagent (Invitrogen). Stable overexpression and silencing were obtained by transducing MDAMB-231, HEK 293T, HEK 293, RCC4, RCC4/VHL, 786-O, 786-O/VHL, and H1299 cells with retroviral or lentiviral vectors. The efficiency of knockdown or overexpression was assessed by Western blotting.

Migration and Invasion Assays:

For migration assays (wound healing assays), cells were seeded in 6-well plates at a density of 15%/well and grown until confluence (around 3 days). Complete medium was replaced with serum-free medium and cells were incubated for 24 hours. Confluent cells (monolayer) were scraped with a P200 tip in each well (3 lines/well), and the medium was replaced with complete medium. After 24 to 48 hours, the cells were fixed with 3.7% paraformaldehyde (PFA). Photographs were obtained at 0, 1, and 2 days. Cell migration was quantified by counting inside the scratch (at time 0 as standard) in each different fields of the wound.

For matrigel invasion assays, RCC4 or RCC4/VHL and 786-O or 786-O/VHL cells were infected with shRNAs in 10 cm dishes. After 8 hours, the medium was changed to serum-free medium and cells were grown to ~80% confluence. Cells were seeded in 24-well invasion chambers (Corning, 354480). Each sample was plated in triplicate (500,000 cells/insert). All protocols were followed as recommended standard protocols. To measure cell invasion, filter were stained with 0.2% Crystal Violet and invasion cells were counted.

Coimmunoprecipitation Assays, Immunoblotting and Antibodies:

To study endogenous WSB1/pVHL binding, cells were treated with or without 10 μM MG 132 (Sigma) for 2 hours. Cells were lysed by sonication in NETN buffer (20 mM Tris-HCl, pH 8.0, 100 mM NaCl, 1 mM EDTA, 0.5% Nonidet P-40) containing 50 mM b-glycerophosphate, 10 mM NaF, and 1 mg/ml each of pepstatin A and aprotinin, freshly supplemented with protease inhibitor cocktail (Roche). Prior to immunoprecipitation, protein A-bound Agarose beads were incubated overnight with pVHL antibody (Cell Signaling, #2738), WSB1 antibody (Abcam, ab68953; Sigma, HPA003293; Proteintech, 1166-1-AP), or HIF-1α antibody (Abcam, ab51608) in PBS with 5% BSA at 4° C. ab68953 was used for most experiments (HPA003293 for IHC). Extracts were added before immunoprecipitation with protein-A agarose at 4° C. for 4 hours. After three washings in binding buffer, co-purified proteins were analyzed by Western blotting.

For ubiquitination assays, HEK 293T cells were infected with the indicated shRNAs with HA-ubiquitin. Before harvesting, cells were treated for 4 hours with proteasome inhibitor (10 μM MG 132; Sigma). Ubiquitination assays were then performed as described previously (Yuan et al., *Cell* 140:384-396, 2010).

To remove the heavy chain, heavy or light-chain-specific anti-mouse and anti-rabbit IgG secondary antibodies were obtained from Jackson Immunoresearch. Rabbit polyclonal antibodies recognizing HIF-2α were purchased from Novus (NB100-122).

Immunofluorescence:

For immunofluorescence staining, HeLa cells were plated on glass cover slips and transfected with the indicated constructs. Cells were then fixed in 3.7% paraformaldehyde for 10 minutes at room temperature, and stained using standard protocols. Immunofluorescence images were taken using fluorescent microscopy (Nikon Microscope, Melville, N.Y.).

Real Time PCR or Reverse Transcription (RT)-PCR of cDNA:

Preparation of RNA and cDNA, as well as qRT-PCR, were performed as described elsewhere (Lee et al., *J Cell Sci* 124:1911-1924, 2011). The following primers were used:

```
HIF-1α Forward:
                                    (SEQ ID NO: 13)
5'-CATGGAAGGTATTGCACTGC-3'

Reverse:
                                    (SEQ ID NO: 14)
5'-CACACATACAATGCACTGTGG-3'

VEGFA Forward:
                                    (SEQ ID NO: 15)
5'-CCTTGCCTTGCTGCTCTACCTC-3'

Reverse:
                                    (SEQ ID NO: 16)
5'-TTCTGCCCTCCTCCTTCTGC-3'

CA90 Forward:
                                    (SEQ ID NO: 17)
5'-CAATATGAGGGGTCTCTGACTACAC-3'

Reverse:
                                    (SEQ ID NO: 18)
5'-GGAATTCAGCTGGACTGGCTCAGC-3'

ALDOC Forward:
                                    (SEQ ID NO: 19)
5'-GCGCTGTGTGCTGAAAATCAG-3'

Reverse:
                                    (SEQ ID NO: 20)
5'-CCACAATAGGCACAATGCCATT-3'

SAP30 Forward:
                                    (SEQ ID NO: 21)
5'-AGTTGGTTGCCACTTTAGGTC-3'

Reverse:
                                    (SEQ ID NO: 22)
5'-CCACGTCTCCTAGTGAACACC-3'

GULT1 Forward:
                                    (SEQ ID NO: 23)
5'-TCATCGTGGCTGAACTCTTCAG-3'

Reverse:
                                    (SEQ ID NO: 24)
5'-TCACACTTGGGAATCAGCCCC-3'
```

β-actin sequence were as described elsewhere (Lee et al., supra).

Cancer Data Collection and Processing:

Cancer datasets were obtained from Gene Expression Omnibus (online at ncbi.nlm.nih.gov/geo) and PROGgene (online at watson.compbio.iupui.edu/chirayu/proggene/database/?url=proggene), containing patients' clinical information and gene expression data (Table 1). Among the various datasets, two major events were specifically defined: WSB1 levels in metastatic patient samples, and the relationships between WSB1 and HIF target genes. To identify relationships between WSB1 and HIF target genes, a classifier described elsewhere was used (Montagner et al., *Nature* 487:380-384, 2012). Briefly, a classification rule was defined based on summarizing the standardized expression levels of WSB1 and HIF-1α's target genes. Analysis of log 2 expression values for both WSB1 and HIF target genes was carried out using the Prism program.

The relationship between WSB1 expression levels and metastasis free survival was defined in human breast cancer and human colon cancer patient datasets using the PROGgene website (online at watson.compbio.iupui.edu/chirayu/proggene/database/?url=proggene).

In Vivo Assays for Animal Experiments:

Mice were housed in Specific Pathogen Free (SPF) animal facilities. For metastasis assays, B16 F10 cells were resuspended in 100 μl of PBS and injected in the tail vein of C57/B16 male mice, aged-matched between 5 and 7 weeks. Seven mice were injected for each sample ($3 \times 10^5$ cells for each mouse). After four weeks, animals were sacrificed and lungs and livers were removed.

Immunohistochemistry:

Tissue arrays included a lung tumor tissue microarray containing 400 pairs of human lung cancer, 21 human invasive colon cancers, and 60 human invasive breast cancers, with matched or unmatched normal adjacent tissue. Immunohistochemical staining was performed as described elsewhere (Yuan et al., supra). Primary antibody dilutions were 1:200 for anti-WSB1 (Sigma-Aldrich), and 1:100 for anti-pVHL (SantaCruz).

Figure 2:
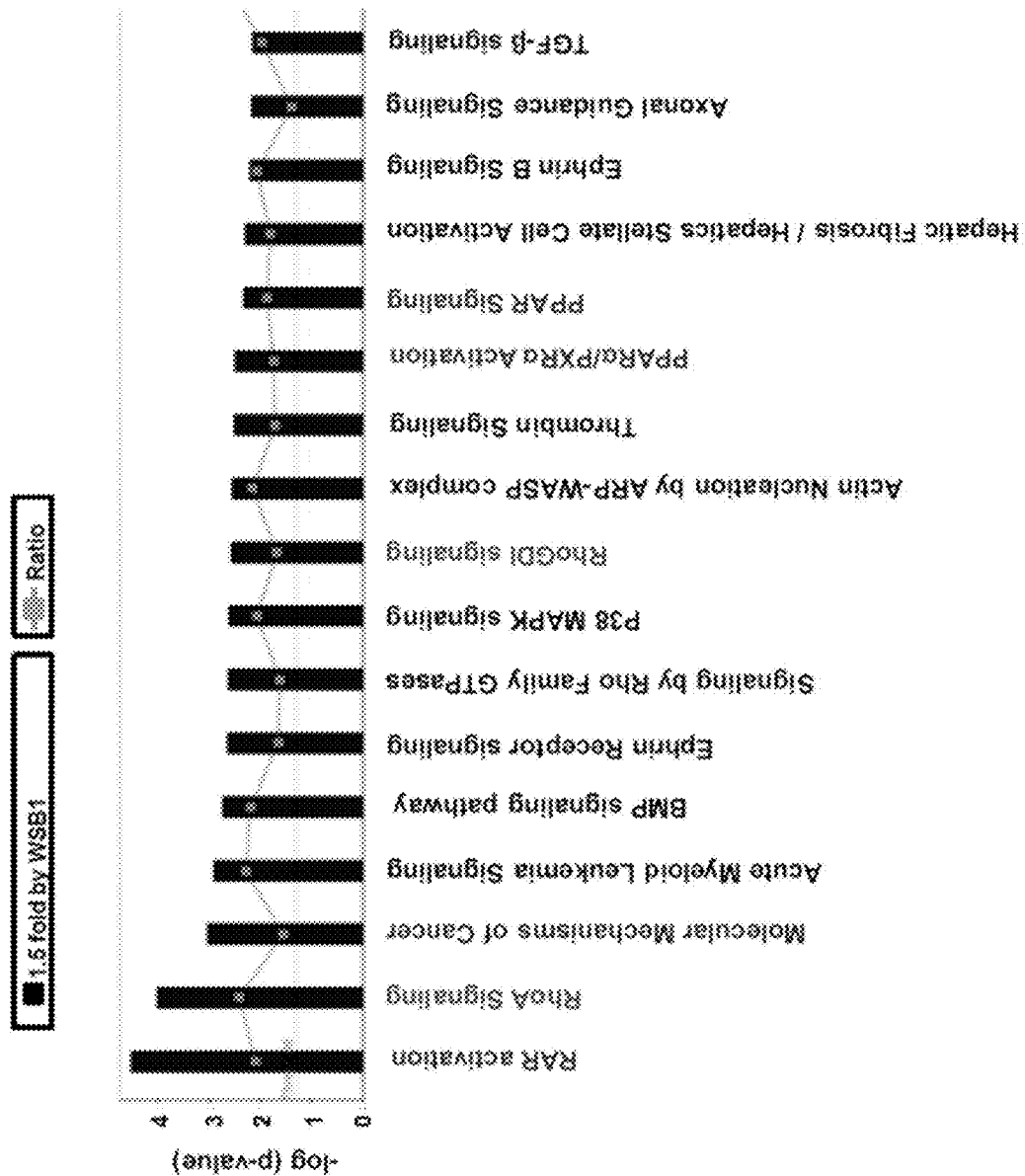
FIG. 2 is a graph plotting the correlation of differentially expressed genes that are associated with canonical pathways in INGENUITY pathway analysis. Total RNA were extracted from 56 pairs of fresh-frozen (FF) primary never smoker lung adenocarcinomas, and analyzed by WSB1 status using INGENUITY pathway analysis.
Figure 4A:
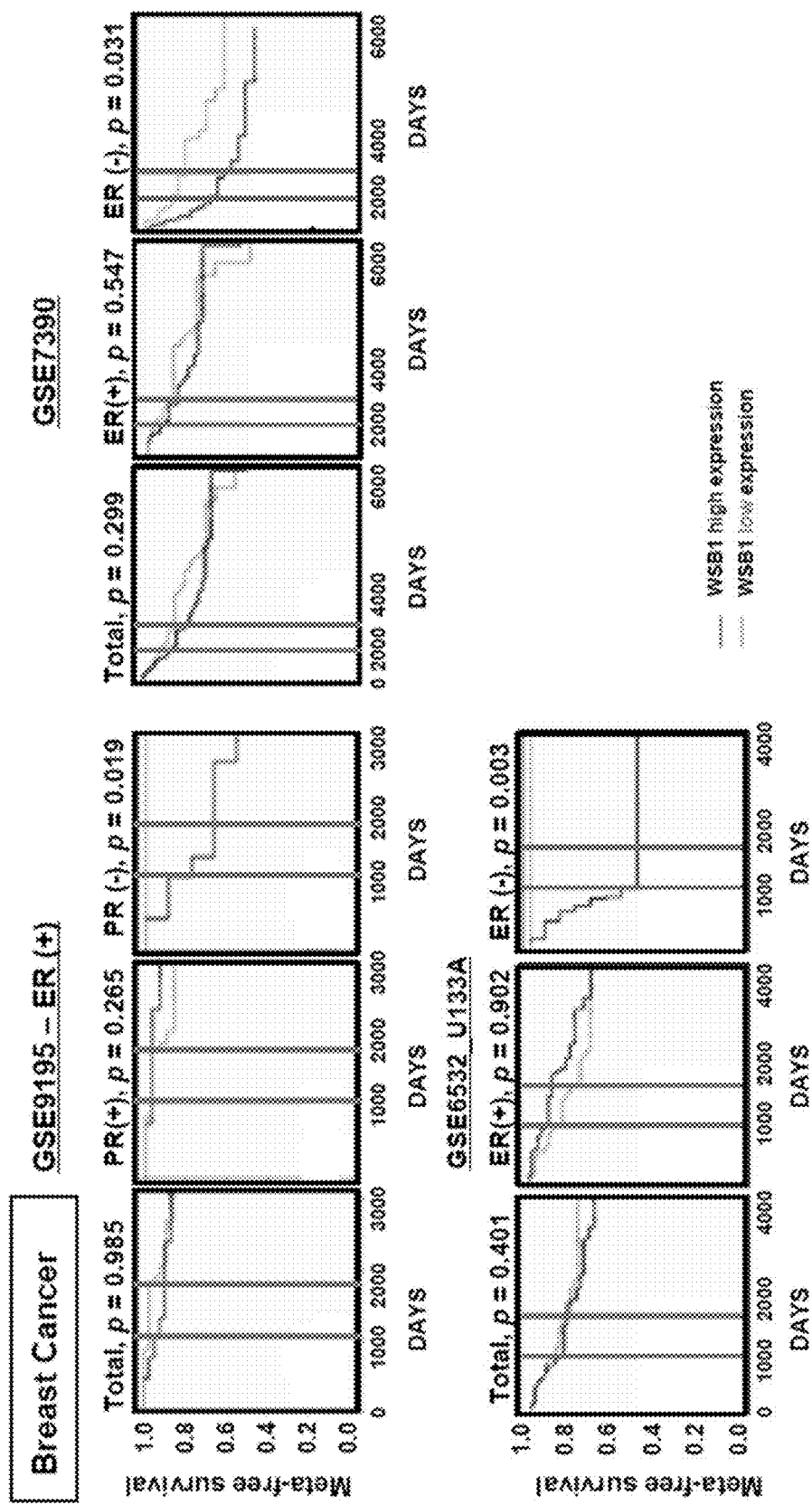
FIGS. 4A, 4B, and 4C are Kaplan-Meier graphs plotting survival of patients having metastatic human breast cancer (FIG. 4A), breast cancer metastasis to brain (FIG. 4B), and metastatic colon cancer (FIG. 4C), stratified according to high or low expression levels of WSB1 (PROGgene).
Figure 4B:
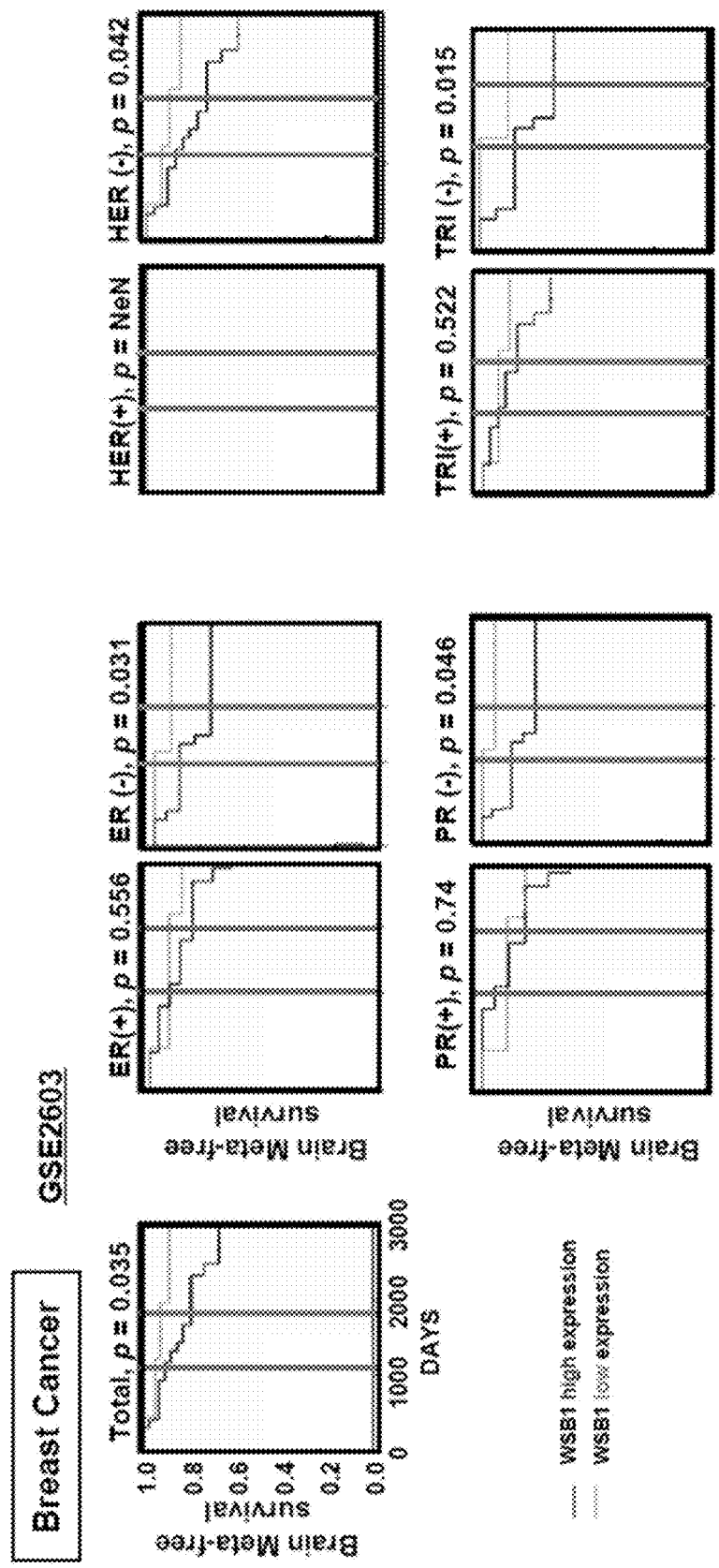
Figure 4C:
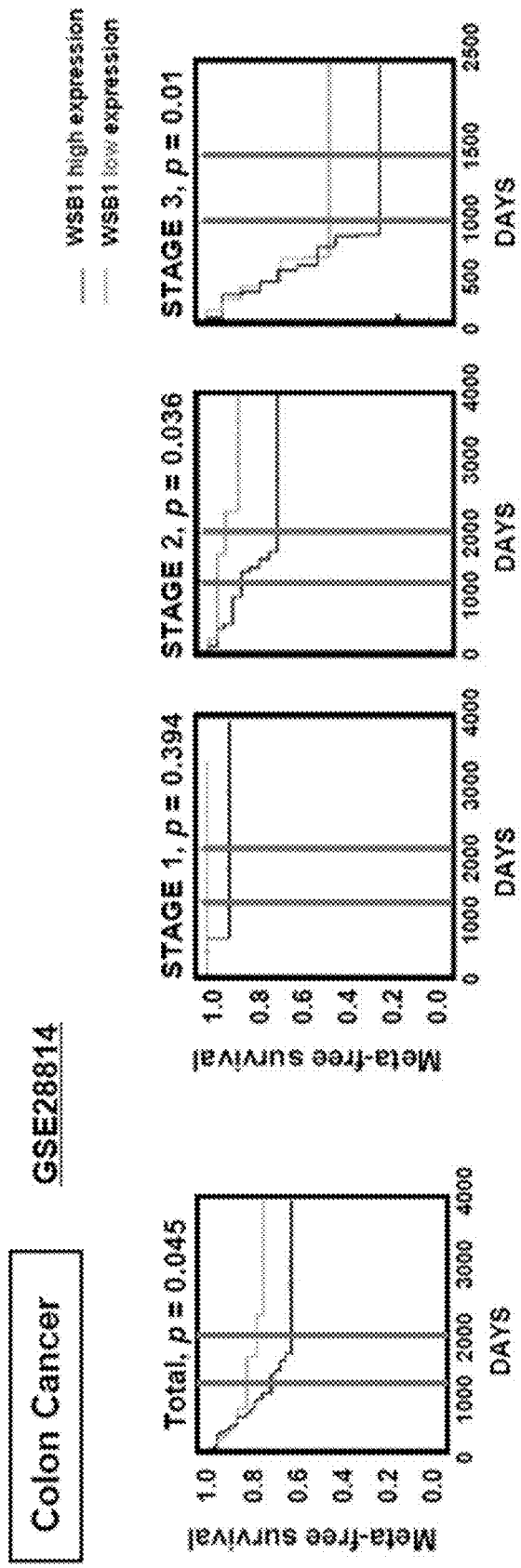

Example 2—WSB1 Regulates HIF and is Positively Associated with Metastasis in Various Tumors To determine whether WSB1 has a functional role in tumor aggressiveness, gene expression profiles from 56 pairs of primary lung adenocarcinoma patient samples were analyzed based on WSB1 status, using INGENUITY pathway analysis (FIGS. 2 and 3). Metastasisor migration-related signals such as RhoA (Friedl et al., Nature Cell Biol 16:208-210, 2014), TGF-β signaling (Pickup et al., Nature Rev Cancer 13:788-799, 2013), and actin nucleation by ARP-WASP complex (Bovellan et al., Current Biol 24:1628-1635, 2014) are top ranked canonical pathways associated with WSB1 expression (FIG. 2). According to the analysis, WSB1 expression is closely associated with pathways that are involved in metastasis and invasion (FIG. 1A). To further investigate the relationship between WSB1 and metastasis, a cohort of 83 melanomas, 171 prostate cancers, and 37 urinary bladder tumors from three clinically annotated gene-expression data sets was analyzed (see, Table 1) for WSB1 expression. In all samples, WSB1 levels were significantly higher in metastatic tissues than in normal or primary tissues (FIG. 1B). Further, for late stage colon cancer and a subset of breast cancer patients, individuals with high WSB1 expression showed lower metastasis-free survival (FIGS. 1C and 4A-4C). Interestingly, for breast cancer, WSB1 expression was associated with poor survival, mostly in ER-, PR-, HER- or triple negative-subtypes.

Figure 1E:
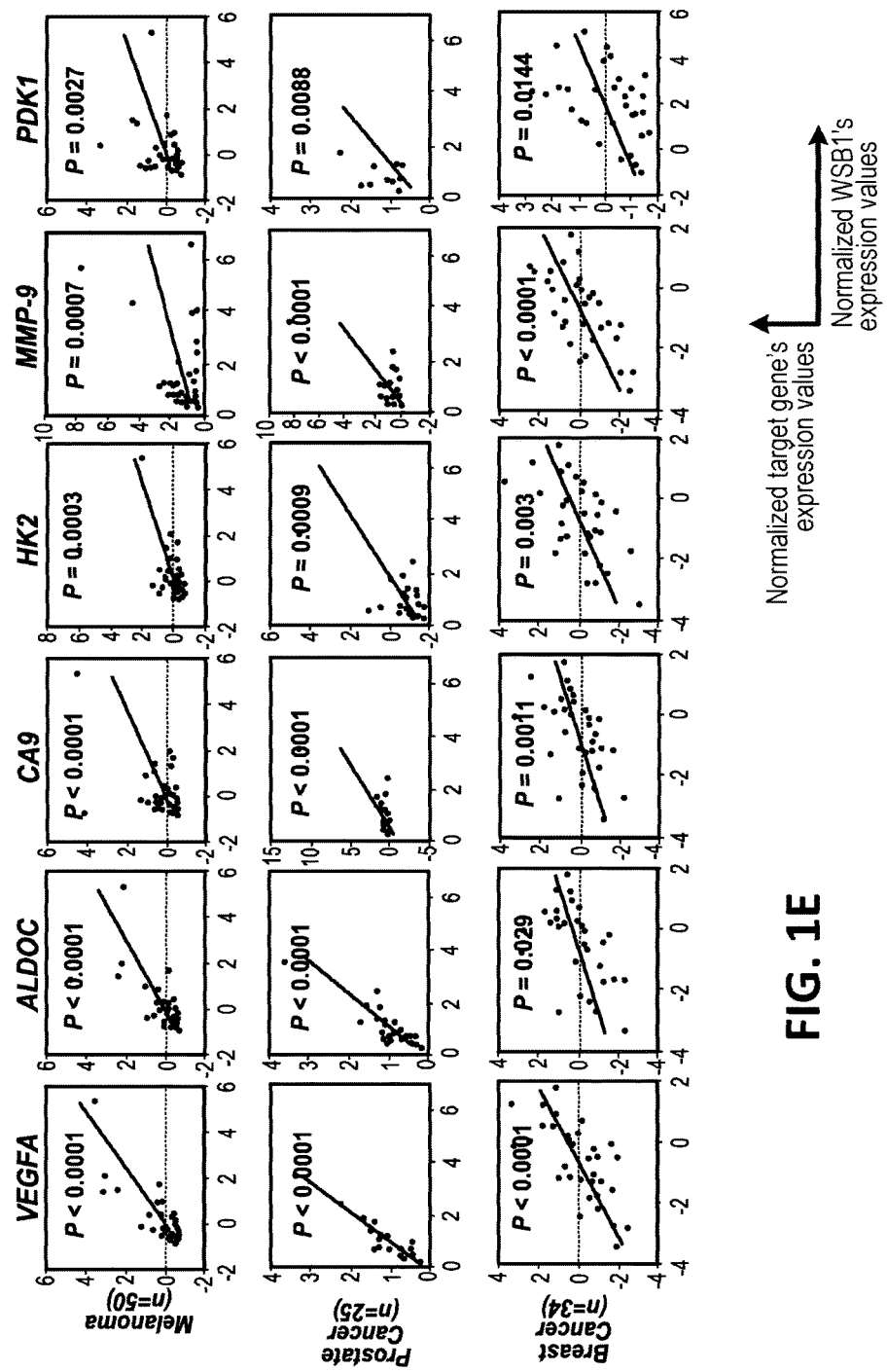
Figure 5:
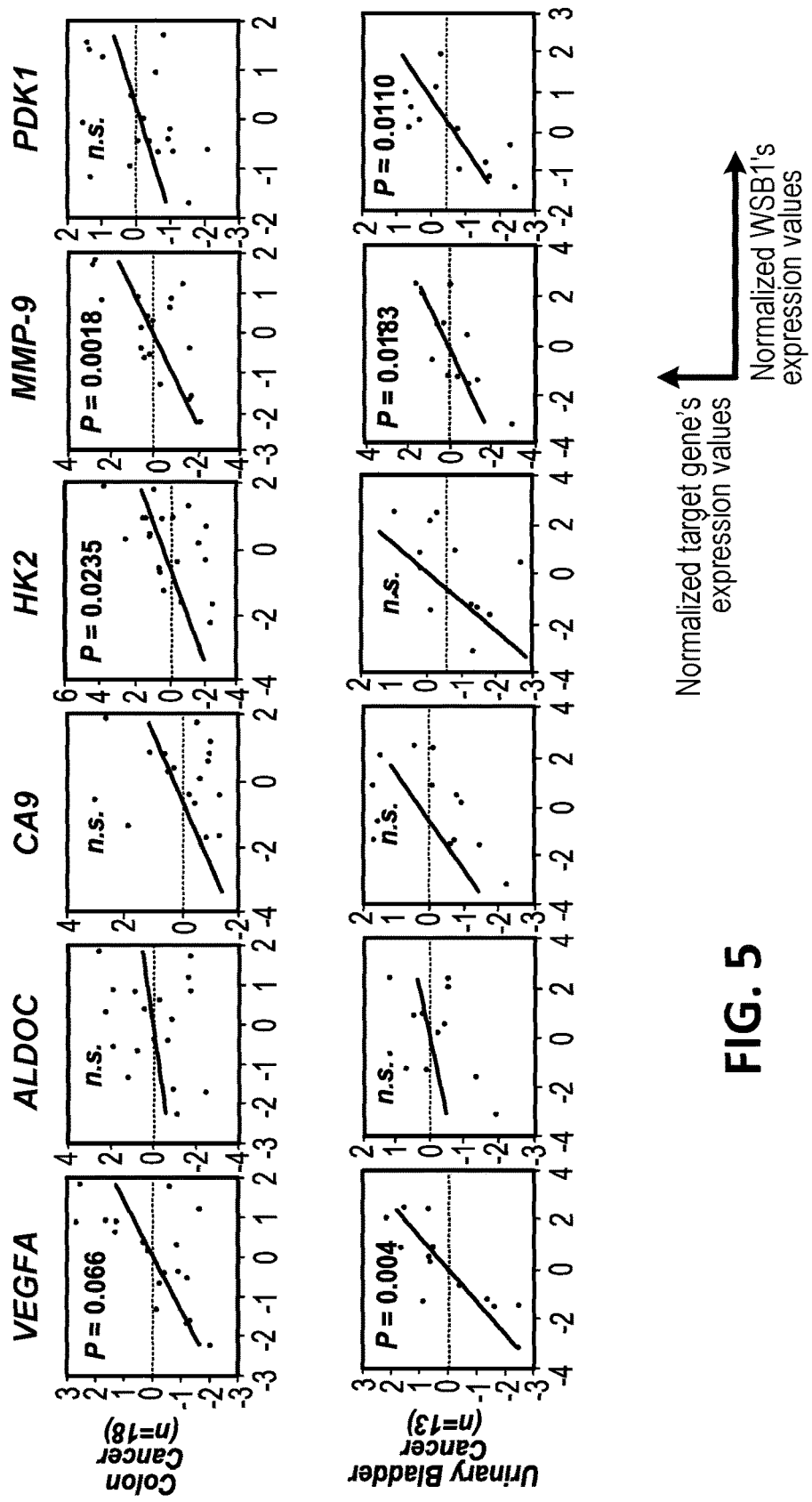
FIG. 5 is a series of graphs plotting the correlation between WSB1 and HIF target gene expression in metastatic colon (top row) and urinary bladder (bottom row) cancer patients (GEO data set listed in Table 1).

Experiments were then conduced to explore whether or how WSB1 regulates metastasis. It was found that endogenous WSB1 expression was positively correlated with the expression of many prometastasis-related genes, and negatively related with most anti-metastasis genes in lung adenocarcinoma patient samples (Table 2). Moreover, HIF target genes were closely matched with WSB1 expression level in several cancer patient samples (FIGS. 1D, 1E, and 5).

Figure 6A:
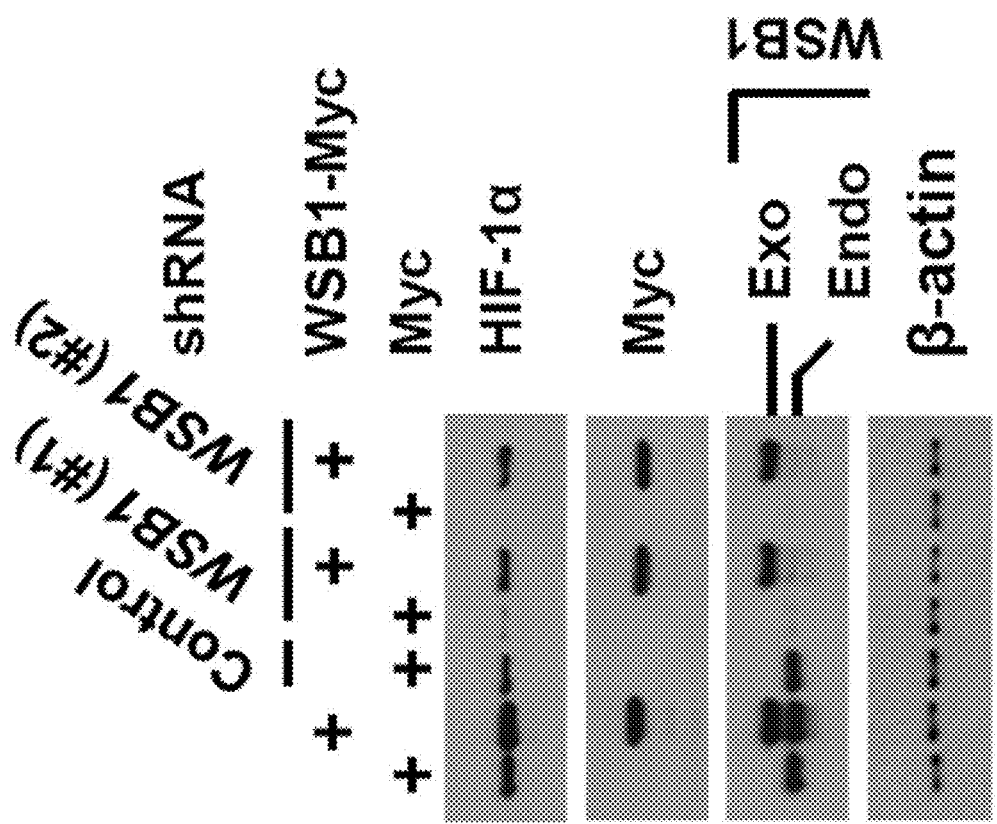
FIGS. 6A-6D demonstrate that WSB1 upregulates HIF-1α activity.
Figure 6B:
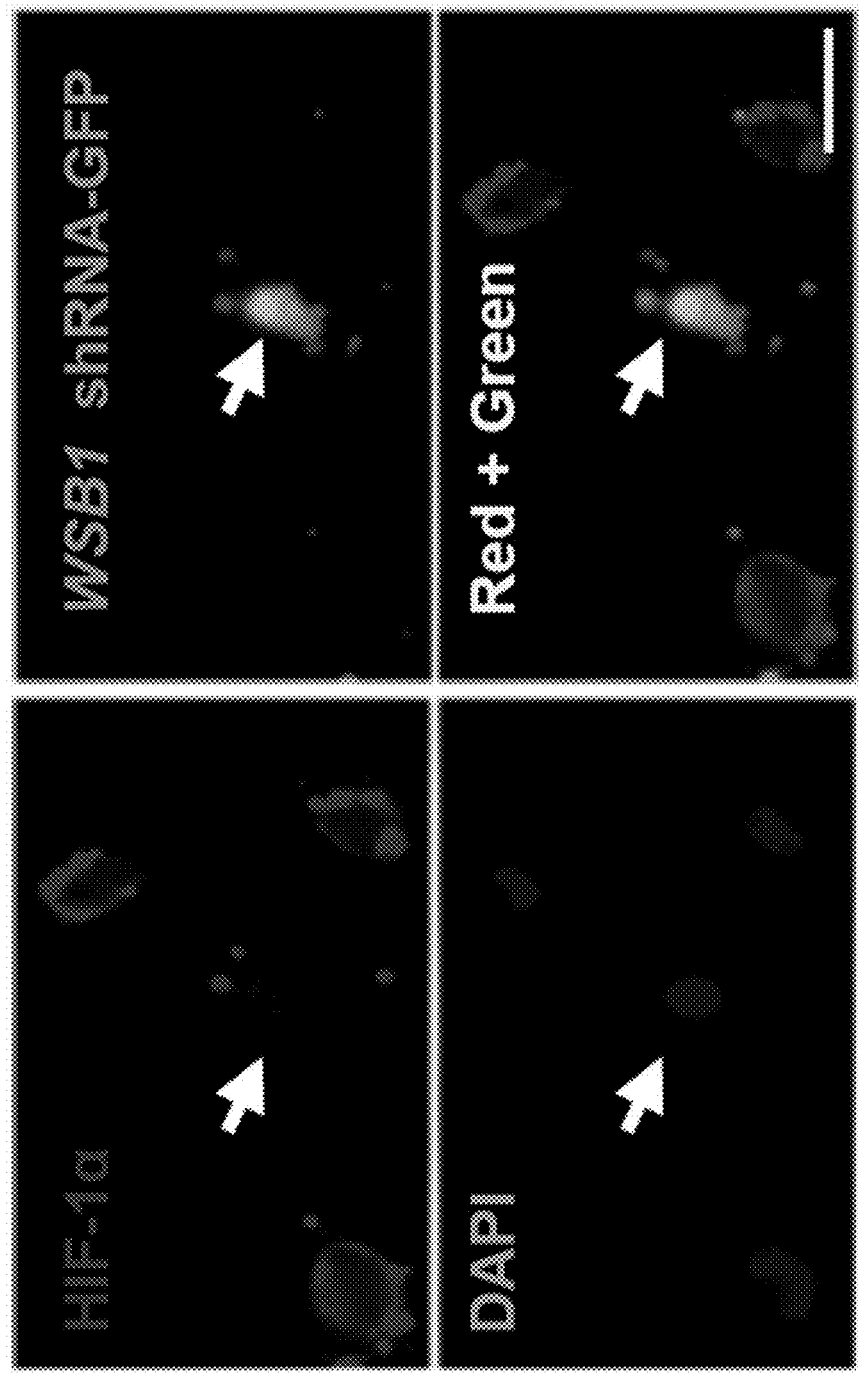
Figure 6C:
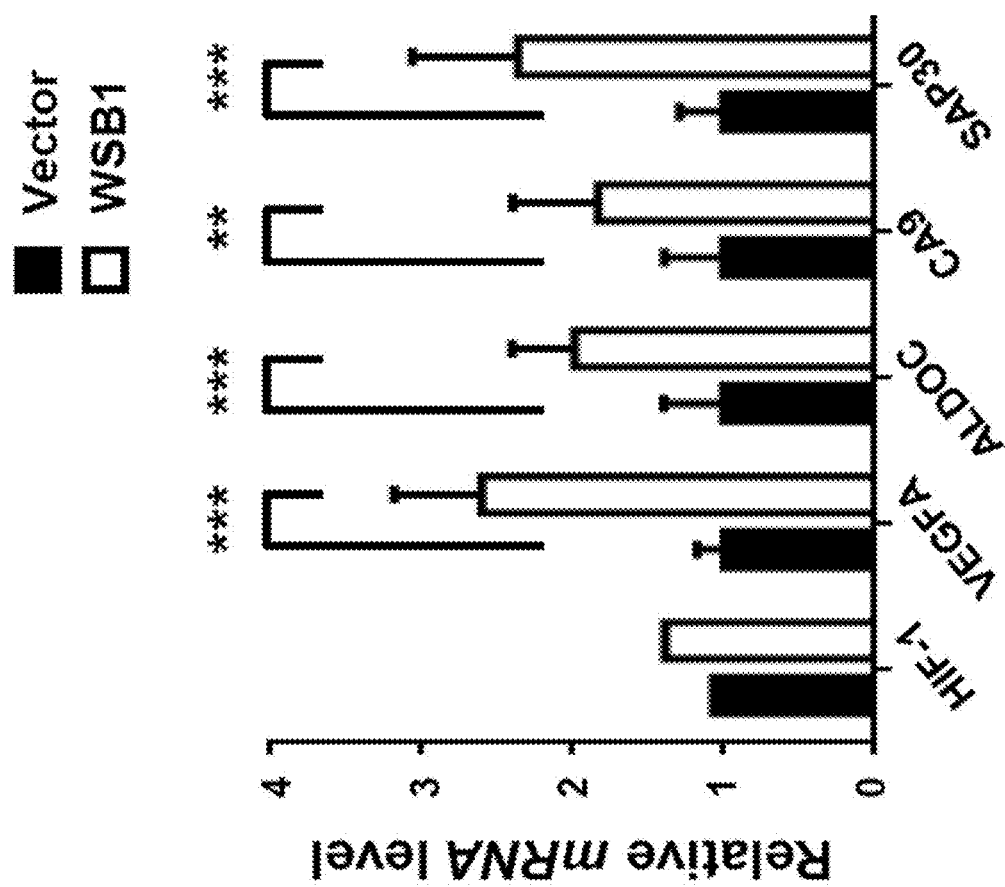
Figure 6D:
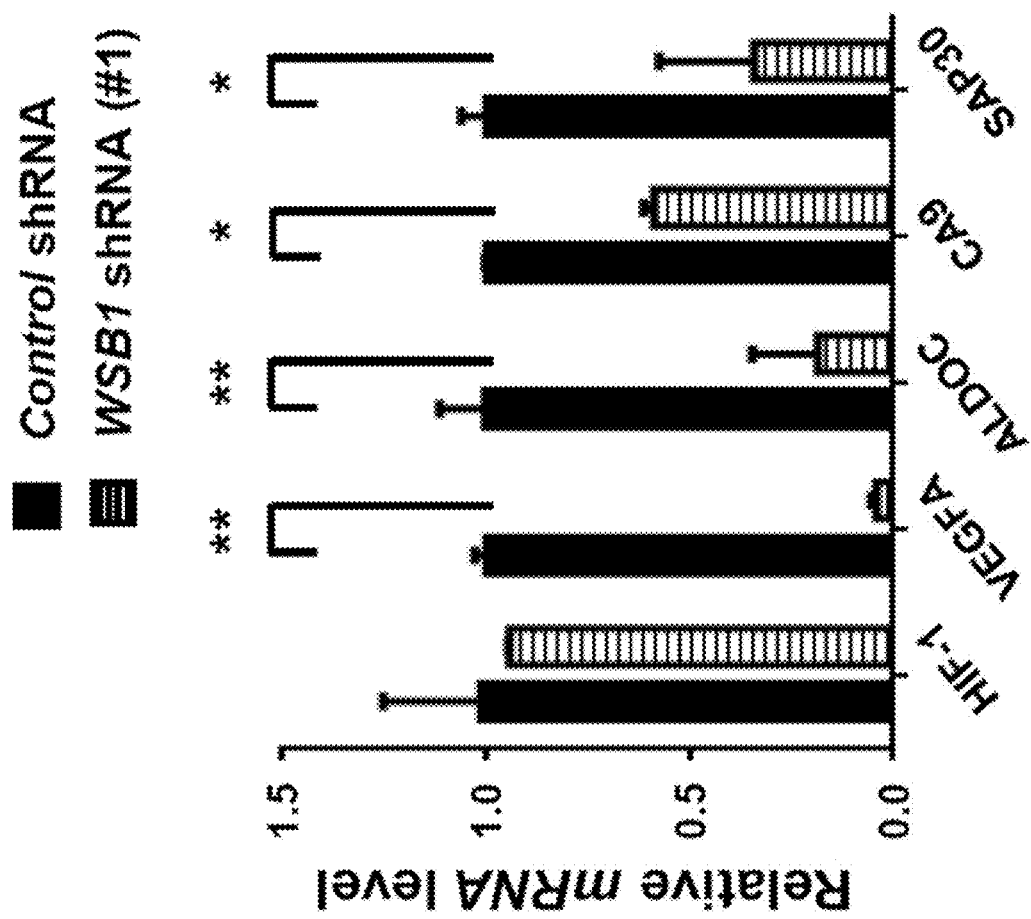
Figure 7B:
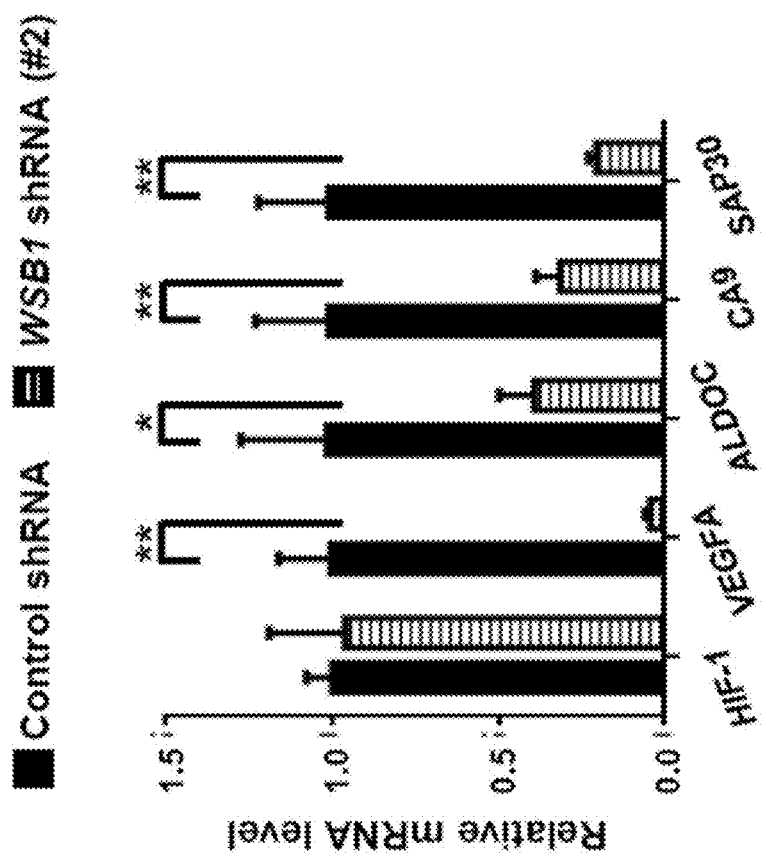
FIGS. 7A and 7B demonstrate that HIF-1α levels and target gene expression were decreased in cells depleted of WSB1.
Figure 7A:
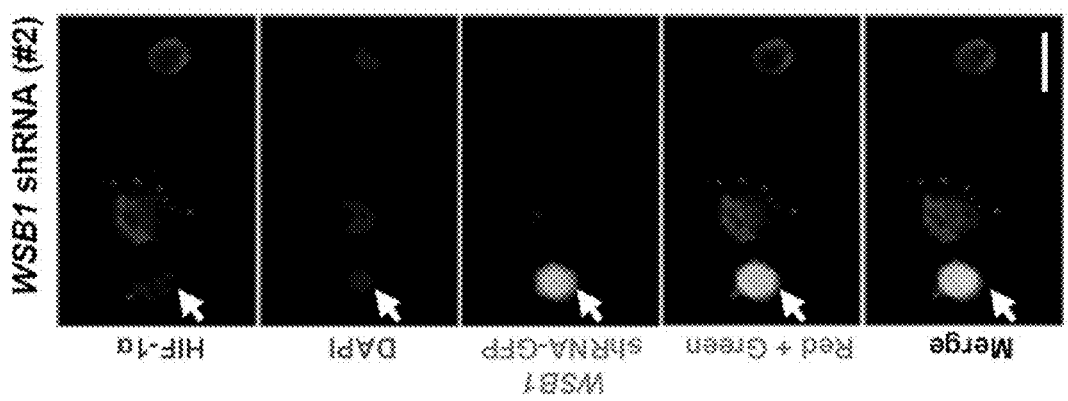

WSB1 may be transcriptionally activated by HIF-1α (Benita et al., Nucl Acids Res 37:4587-4602, 2009; Tong et al., supra), and this correlation might reflect a positive correlation among HIF-1α target genes. Interestingly, it was found that HIF-1α levels were greatly increased in cells overexpressing WSB1, and decreased in cells depleted of WSB1. WSB1 expression in cells depleted of WSB1 restored HIF-1α levels (FIGS. 6A, 6B, and 7A), suggesting that WSB1 positively regulates HIF-1α levels. Thus, there may be a feedback loop between WSB1 and HIF-1α. mRNA levels for HIF-1α target genes (VEGFA, ALDOC, CA9, and SAP30; Cairns et al., Cancer 11:85-95, 2011; Gilkes et al., Nature Rev Cancer 14:430-439, 2014; and Montagner et al., supra) and HIF-1α were evaluated in cells overexpressing WSB1 or depleted of WSB1. WSB1 was found to positively regulate mRNA levels of HIF-1α target genes (FIGS. 6C, 6D, and 7B). In contrast, HIF-1α mRNA levels were not affected by WSB1. These results suggested that WSB1 positively regulates HIF-1α levels post-transcriptionally.

Example 3—WSB1 Regulates pVHL Levels Through Ubiquitinating pVHL

Figures 8D, 8E:
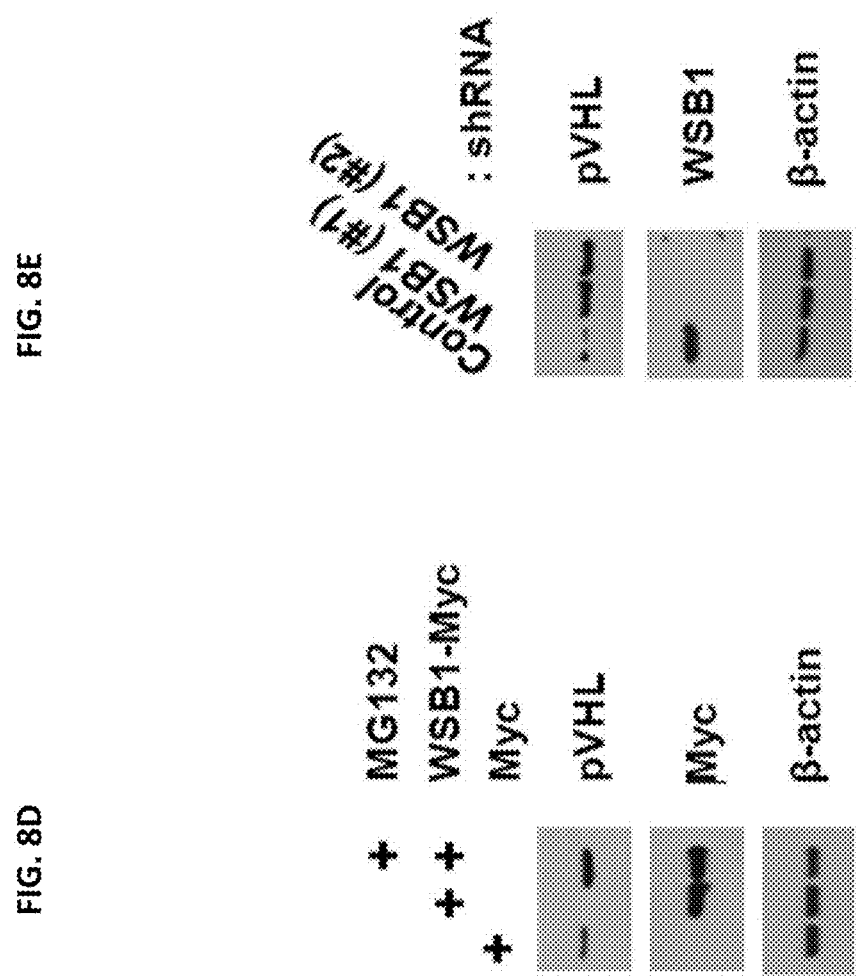
Figure 8F:
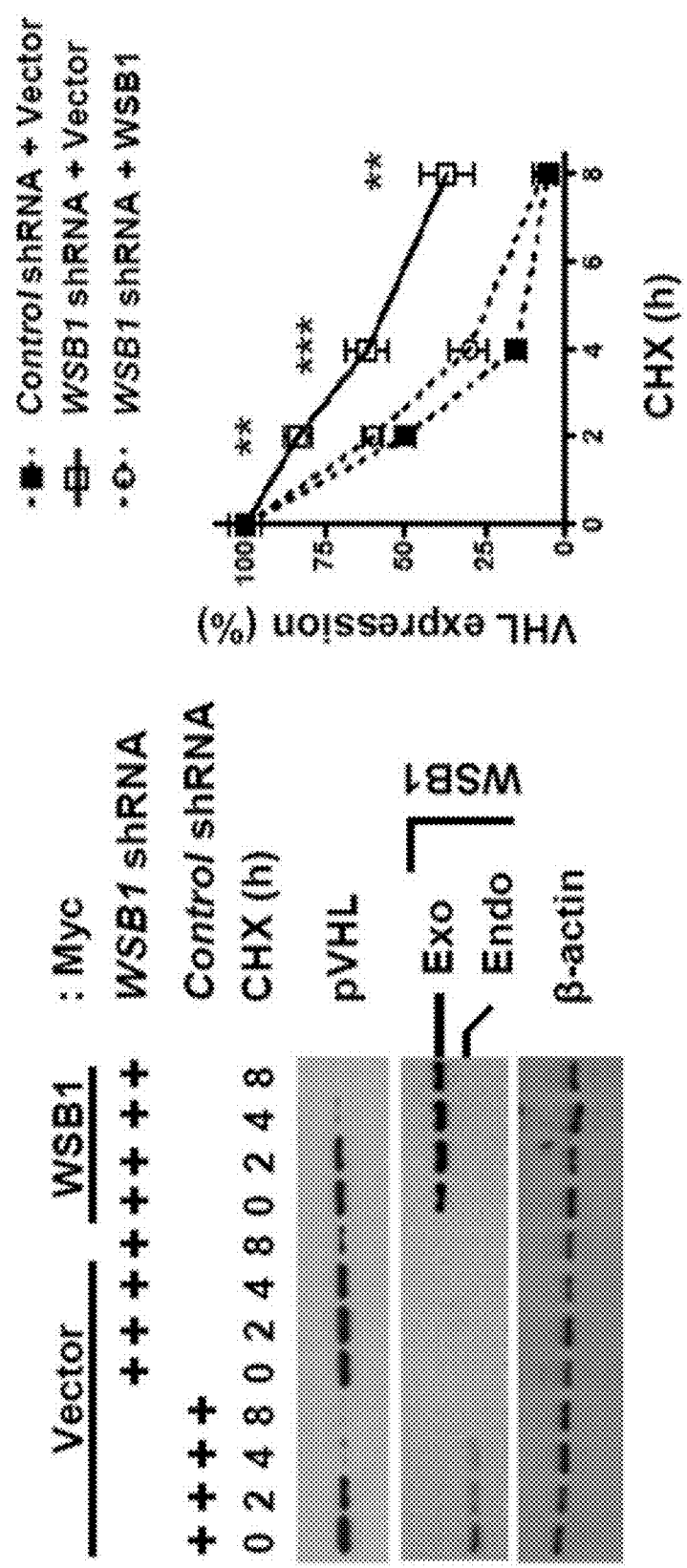
Figure 8G:
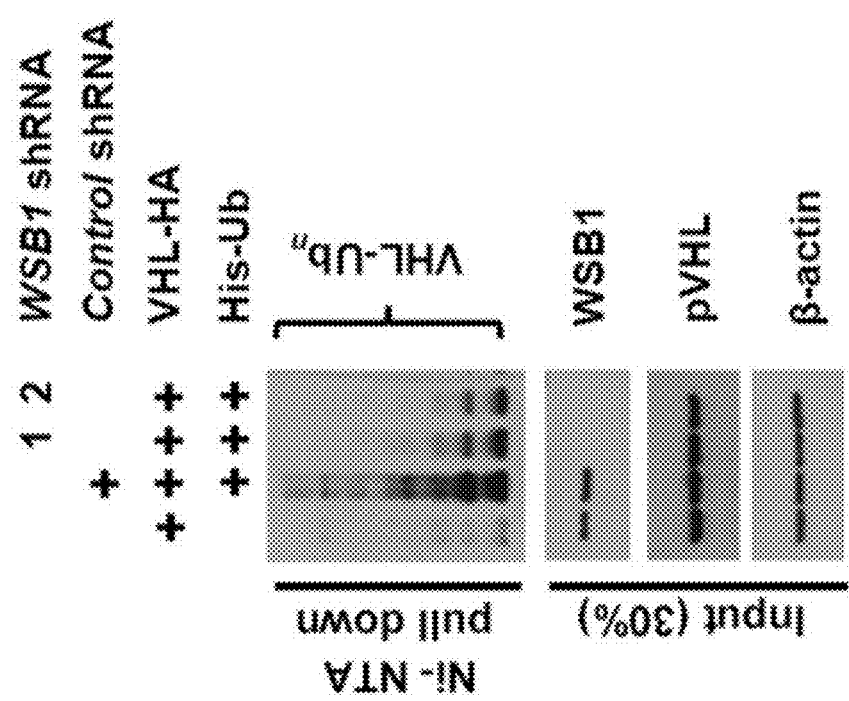
Figure 9A:
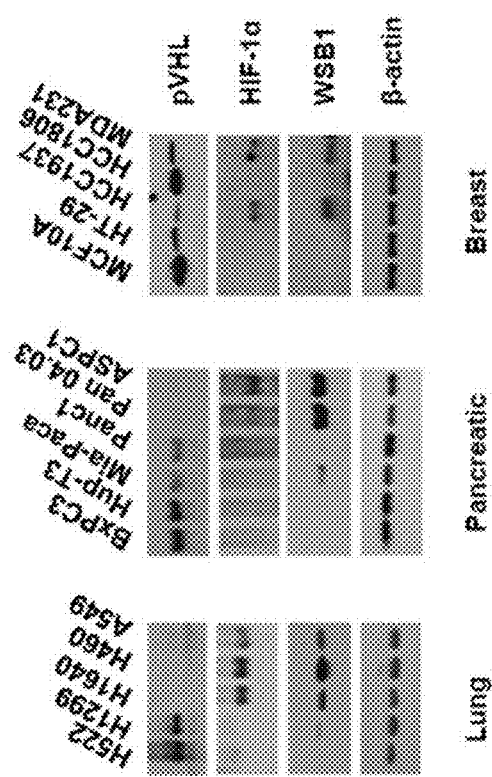
FIGS. 9A and 9B demonstrate that WSB1 regulates pVHL ubiquitination and degradation.
Figure 9B:
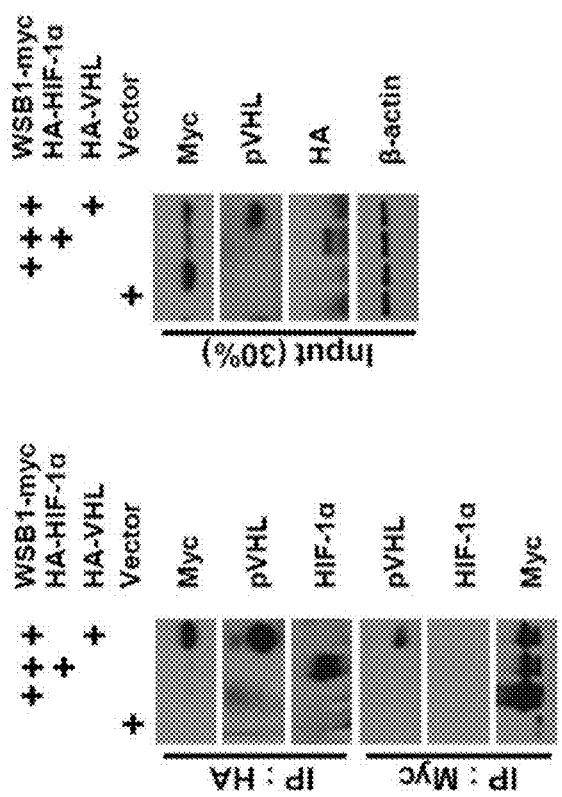

Studies were conducted to examine how WSB1 regulates HIF-1α levels. WSB1 was not observed to interact with HIF-1α (FIGS. 8A and 9A). Rather, an interaction between WSB1 and pVHL was observed (FIGS. 8B and 9A), suggesting that WSB1 might regulate HIF-1α through pVHL. WSB1 is known as an E3 ligase (Dentice et al., Nature Cell Biol 7:698-705, 2005). Thus, studies were carried out to examine whether pVHL level is regulated by WSB1. When WSB1 was overexpressed, the level of pVHL protein decreased, and HIF-1α levels increased in a dosage-dependent manner (FIG. 8C). The decrease in pVHL induced by WSB1 overexpression was reversed by the proteasome inhibitor MG 132 (FIG. 8D). Conversely, knocking down WSB1 resulted in a marked increase in pVHL levels (FIG. 8E). WSB1 also was found to regulate pVHL stability, as depletion of WSB1 increased pVHL stability, while reconstitution of cells with WSB1 restored pVHL stability to that of control cells (FIG. 8F). In pancreatic cancer cell lines, NSCLC cell lines, and breast cancer cell lines, negative correlations also were observed between WSB1 and pVHL levels, while positive correlations were observed between WSB1 and HIF-1α (FIG. 9B). These results suggested that WSB1 negatively regulates pVHL stability, possibly through regulation of pVHL ubiquitination. Indeed, knocking down WSB1 was found to decrease pVHL ubiquitination (FIG. 8G).

Figure 10A:
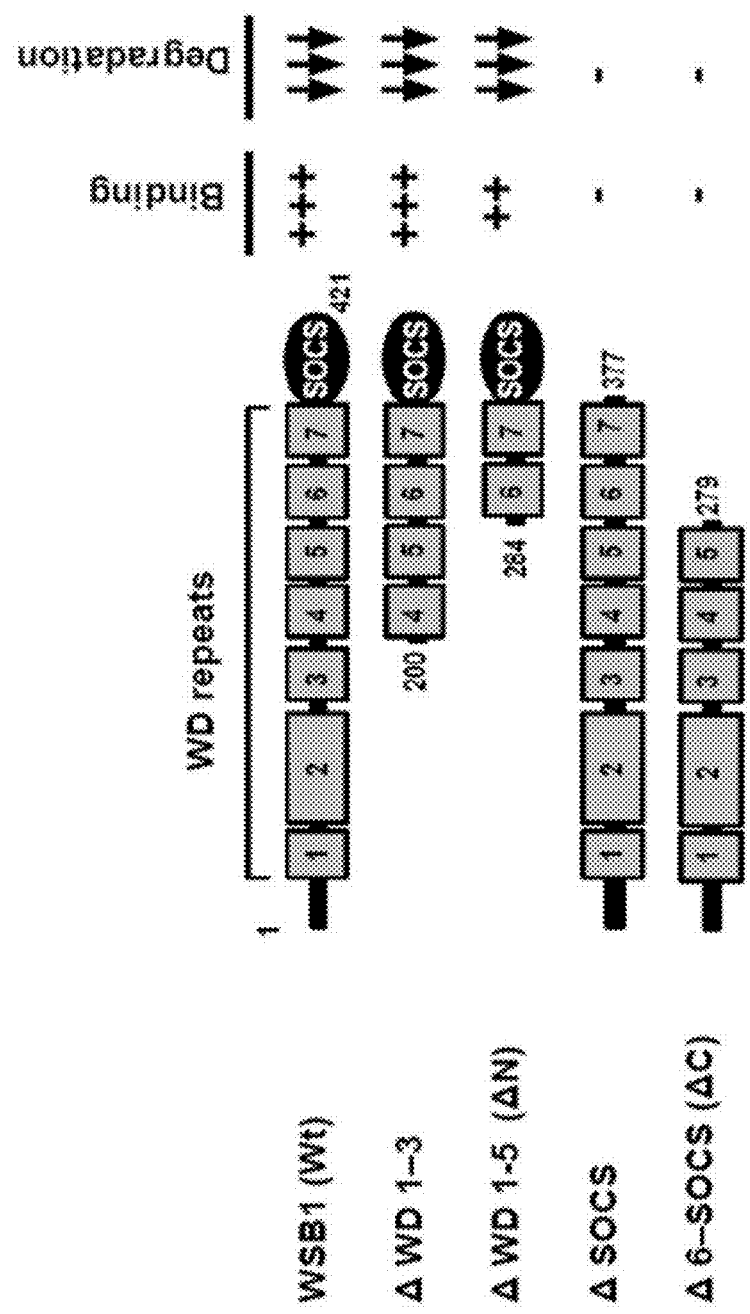
Figure 10B:
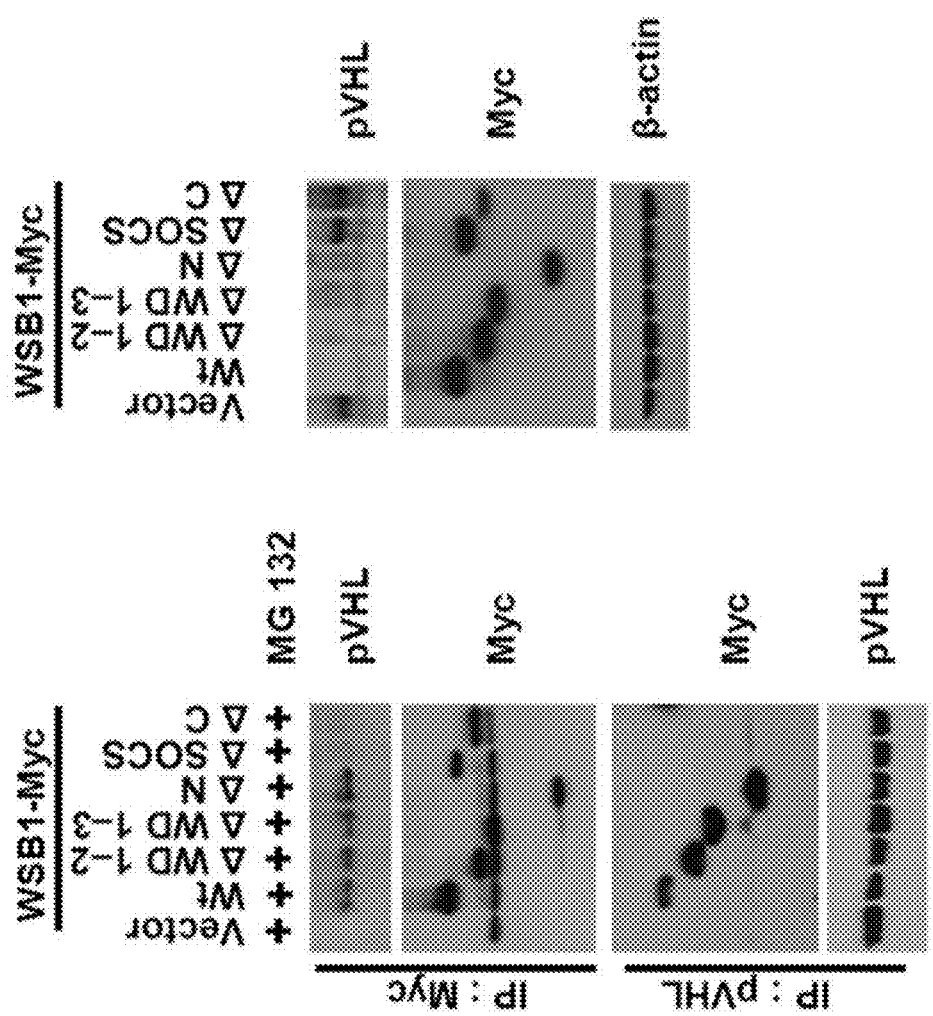
Figure 10E:
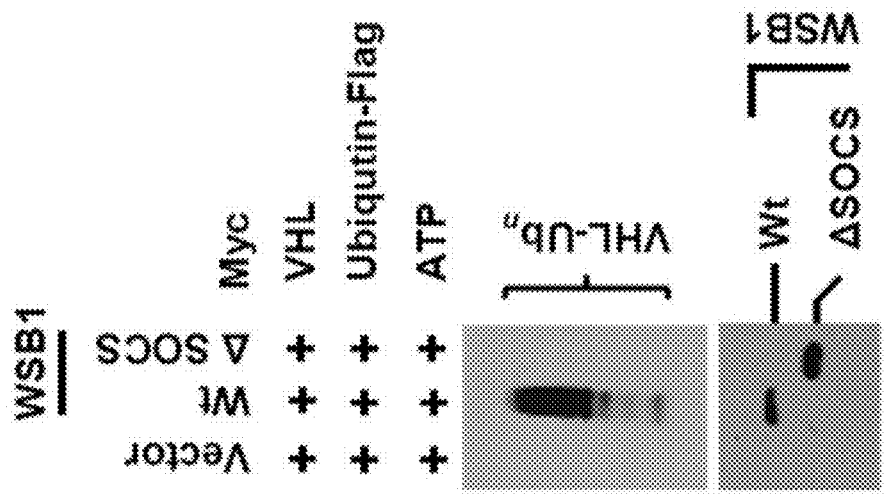
Figure 10D:
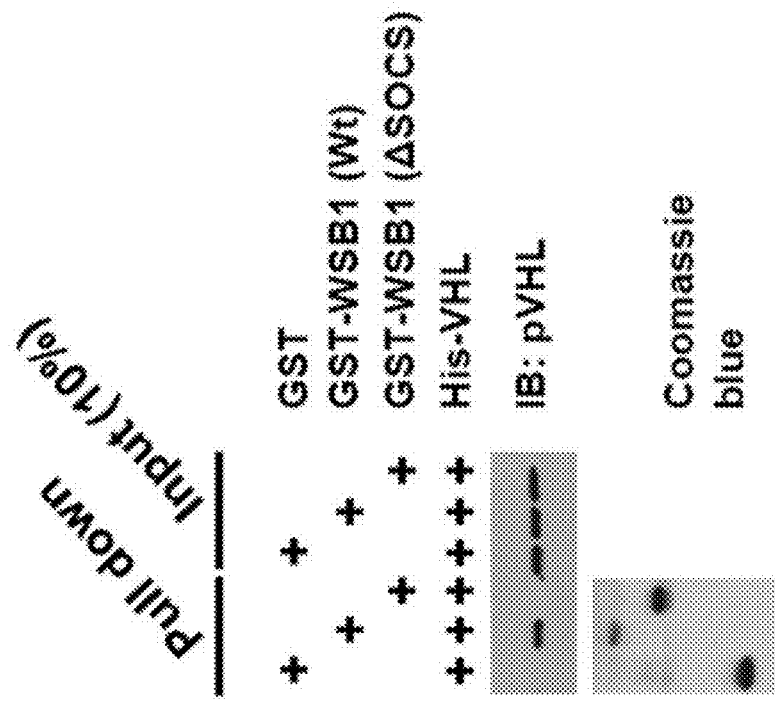

Example 4—the SOCS Domain of WSB1 is Required for pVHL Interaction and Ubiquitination WSB1 contains WD repeats and a SOCS domain (Dentice et al., supra). To determine the regions of WSB1 that are required for its interaction with pVHL, Myc-tagged WSB1 deletion mutants were expressed in cells, and co-immunoprecipitation was performed. These studies showed that the interaction of WSB1 with pVHL requires the SOCS domain. In addition, the down regulation of pVHL by WSB1 was found to be dependent on the SOCS domain (FIGS. 10A and 10B). WSB1 fragments containing the SOCS domain led to decreased pVHL levels, while fragments lacking the SOCS domain could not do so (FIG. 10B). Further, reconstituting cells depleted of WSB1 with WT WSB1 restored pVHL polyubiquitination, while reconstituting these cells with WSB1 (Δ SOCS) did not (FIG. 10C). WSB1 also interacted directly with pVHL in vitro (FIG. 10D), and promoted pVHL polyubiquitination in vitro (FIG. 10E). Thus, WBS1 appears to be is an E3 ligase that regulates pVHL ubiquitination in cells.

Example 5—WSB1 Promotes pVHL Proteasomal Degradation in Hypoxia

Figure 11B:
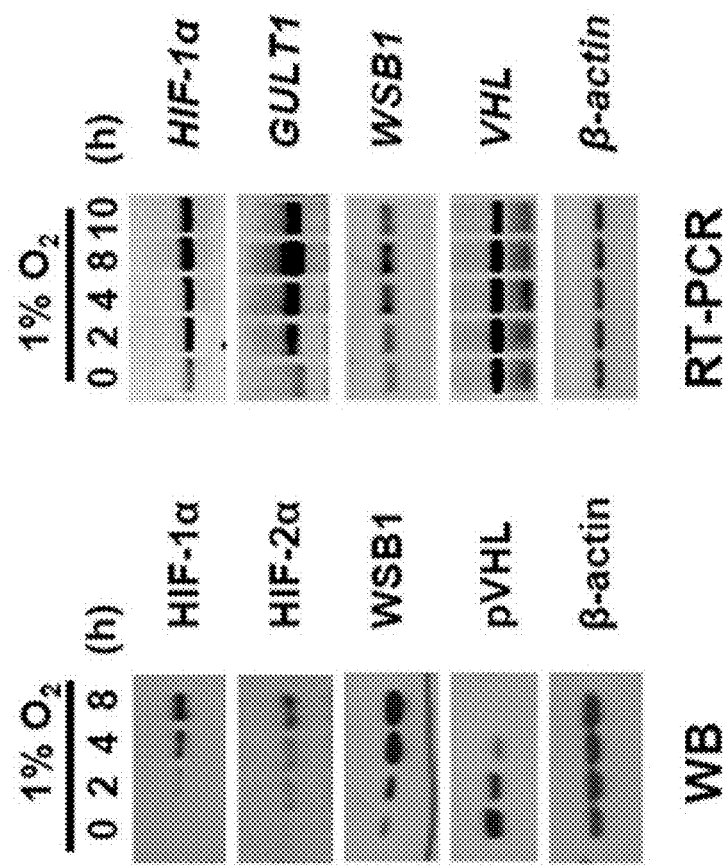
FIGS. 11A-11D demonstrate that WSB1 regulates pVHL under hypoxia conditions.
Figure 11A:
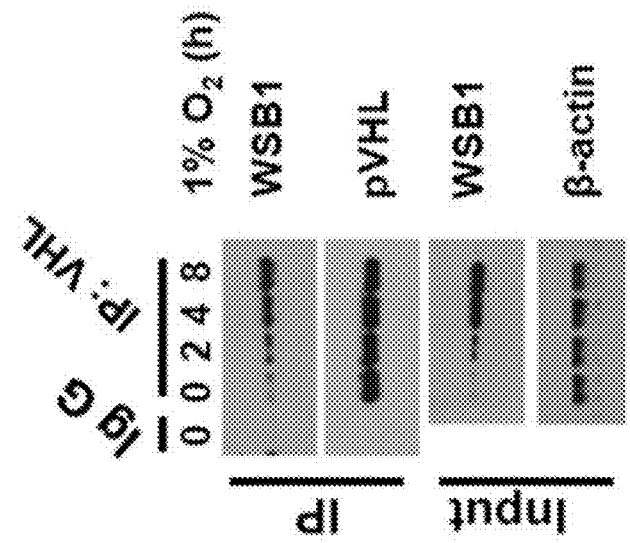
Figure 12B:
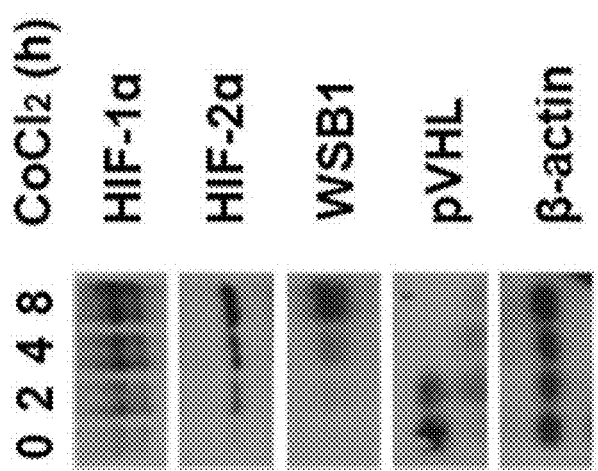
FIGS. 12A and 12B demonstrate that WSB1 interacts with pVHL in hypoxia mimic conditions.
Figure 12A:
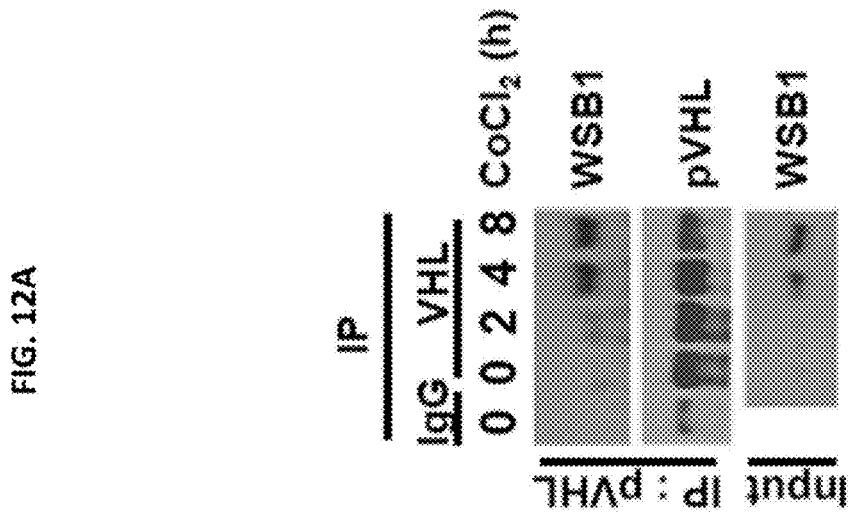

Given that WSB1 regulates pVHL and HIF-1α levels under normoxic conditions, studies were conducted to assess whether WSB1 also regulates pVHL and HIF-1α levels under hypoxia condition. HIFs are unstable proteins that are degraded even under hypoxic conditions (Kong et al., J Biol Chem 282:15498-15505, 2007; Liu et al., Oncogene 30:21-31, 2011; and Uchida et al., J Biol Chem 279:14871-14878, 2004). The interaction between WSB1 and pVHL was increased under hypoxia and hypoxia mimic conditions (FIGS. 11A and 12A). This increase might be due to increased WSB1 expression under hypoxic conditions. In addition, when cells were cultured under hypoxic conditions, endogenous pVHL levels decreased while HIF-1α, HIF-2α, and WSB1 levels increased (FIGS. 11B and 12B). Interestingly, VHL mRNA levels did not changed in hypoxia, while for comparison HIF-1α, Glut1 (an HIF-1α target gene) and WSB1 mRNA levels increased under the same conditions (FIG. 11B), supporting the idea that WSB1 regulates pVHL at the post-transcriptional level, and acts as an E3 ubiquitin ligase for pVHL in hypoxia.

Figure 11D:
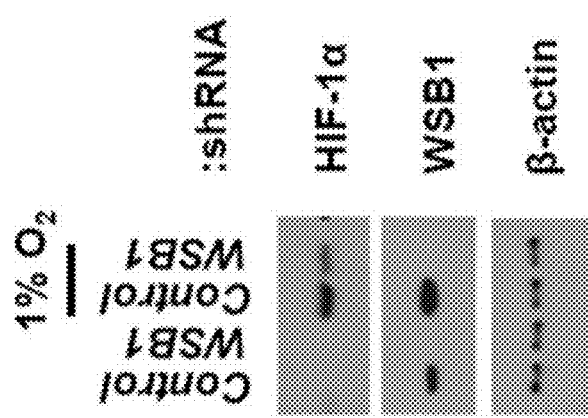
Figure 11C:
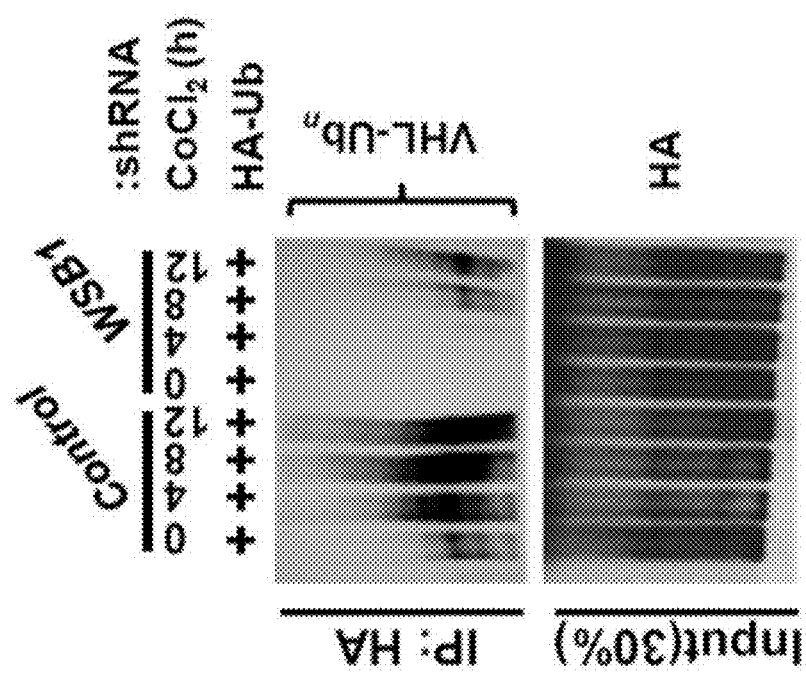

Further, ubiquitination of pVHL was increased under hypoxia-mimic conditions, and knocking down WSB1 decreased pVHL polyubiquitination (FIG. 11C). Knocking down WSB1 also decreased the up regulation of HIF-1α under hypoxia conditions (FIG. 11D). Overall, these results suggested that WSB1 regulates pVHL turnover and contributes to HIF-1α and HIF-2α up regulation under hypoxic conditions.

Figure 13A:
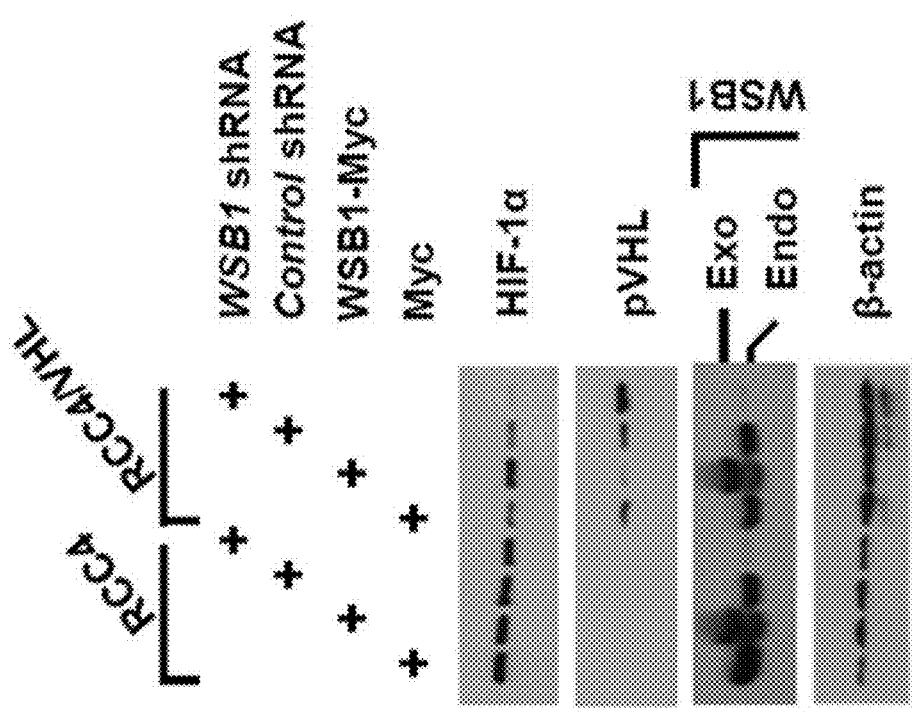
FIGS. 13A-13D demonstrate that WSB1 promotes cancer cell invasion and migration by inhibiting pVHL.
Figure 13B:
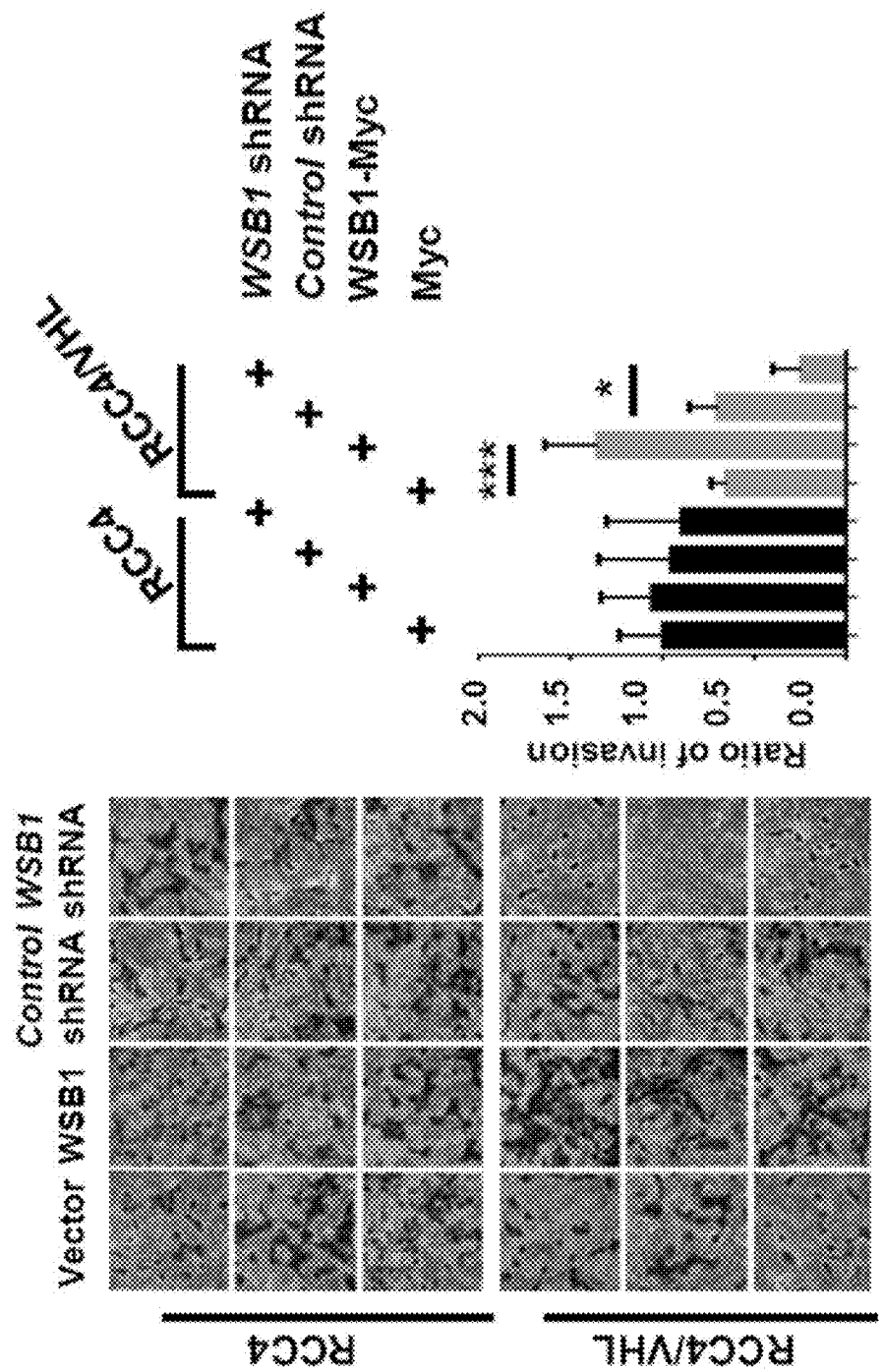
Figure 13C:
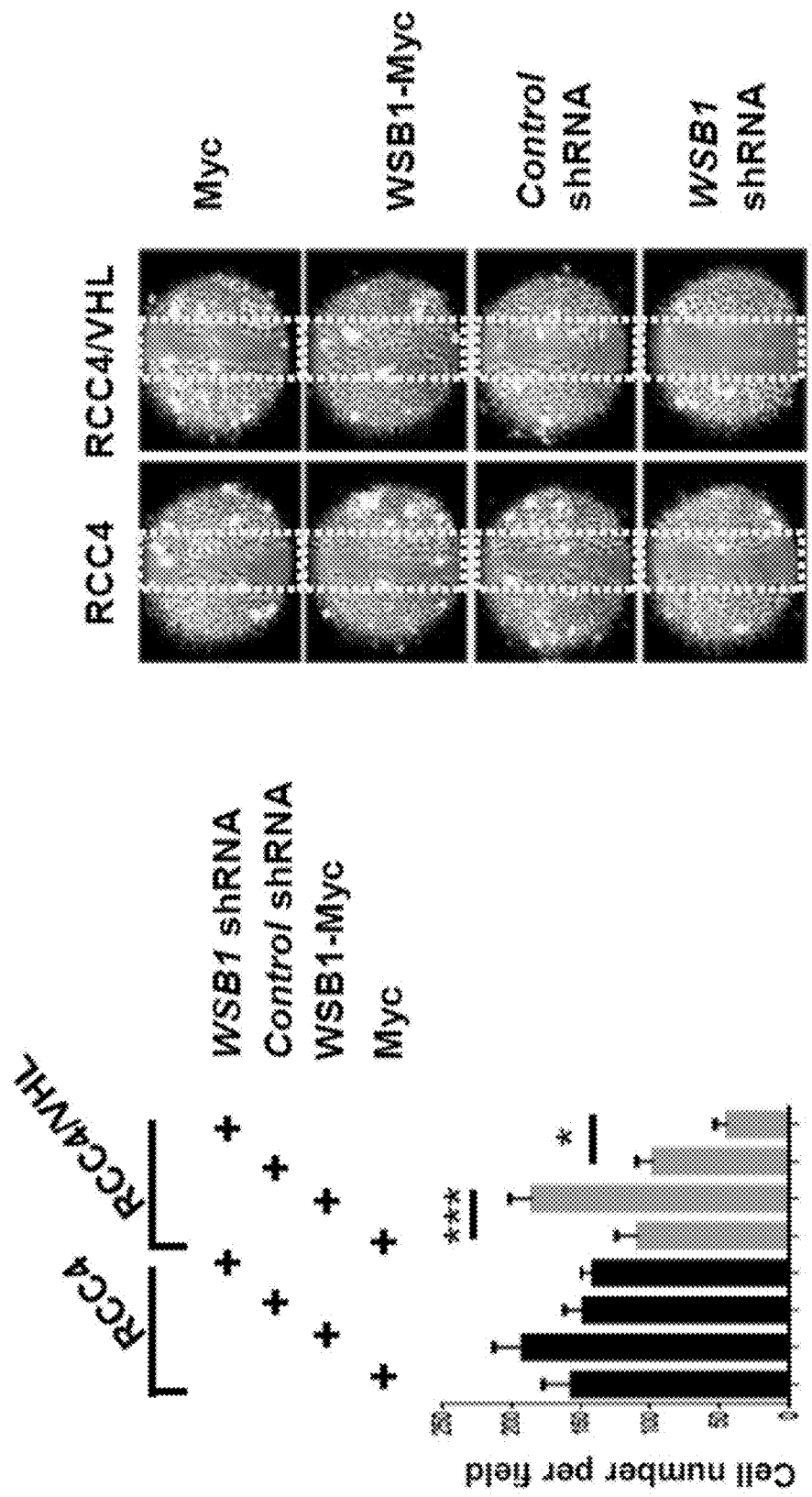
Figure 13D:
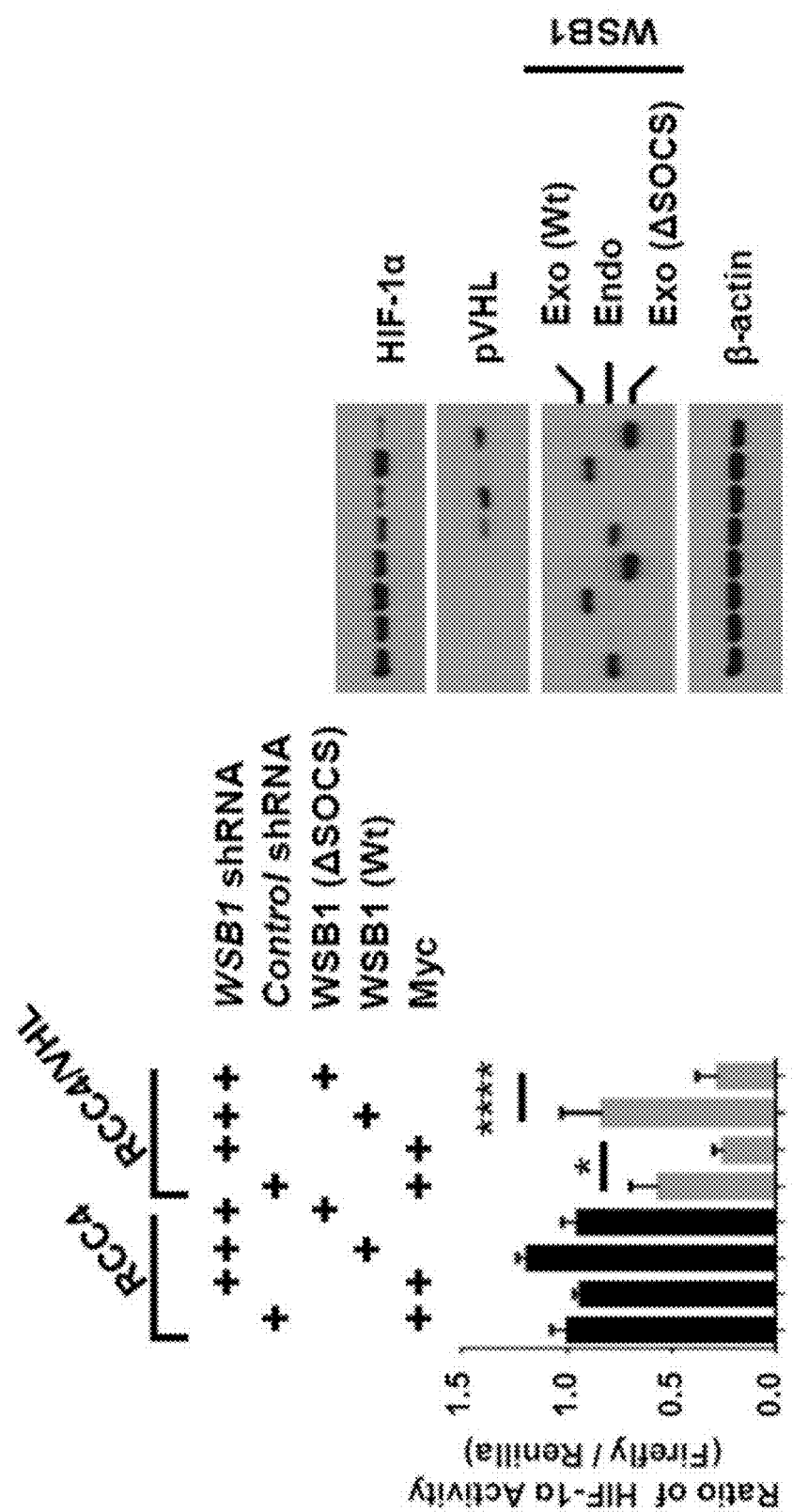
Figure 14A:
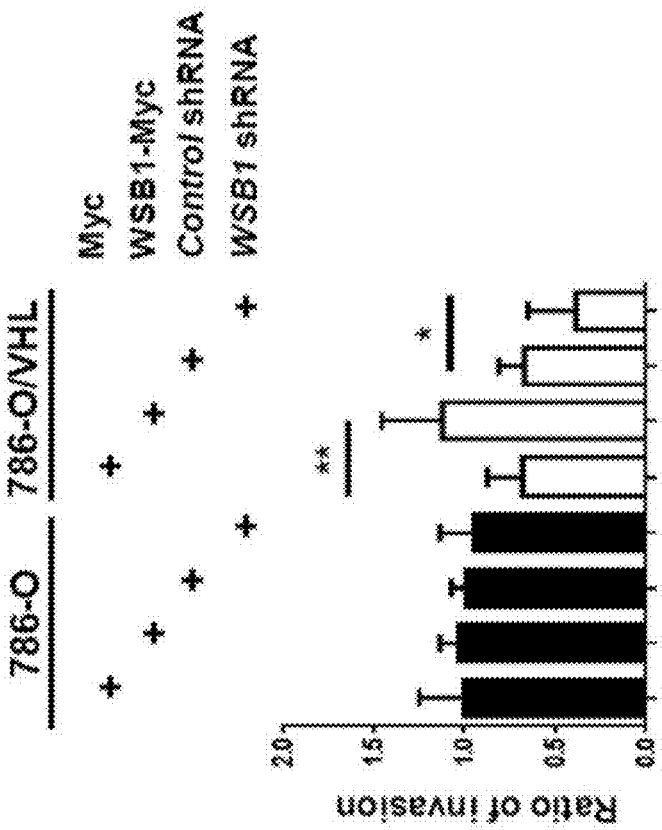
Figure 14B:
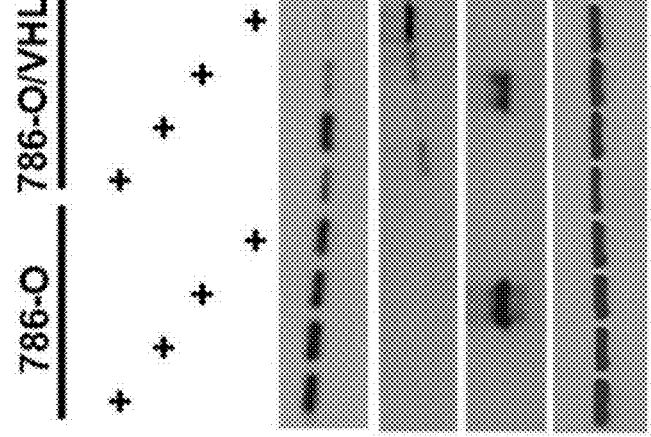
Figure 14D:
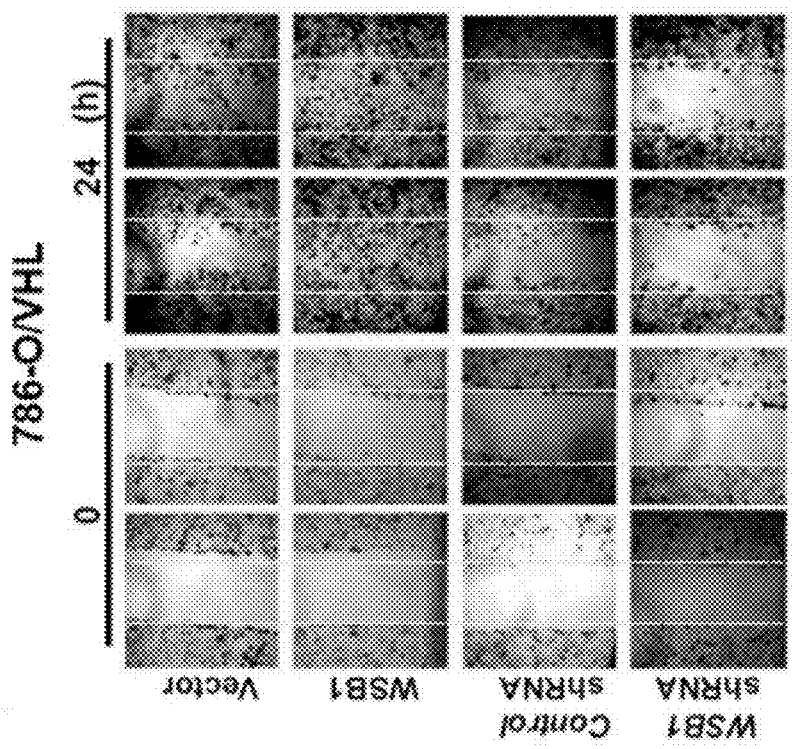
Figure 14C:
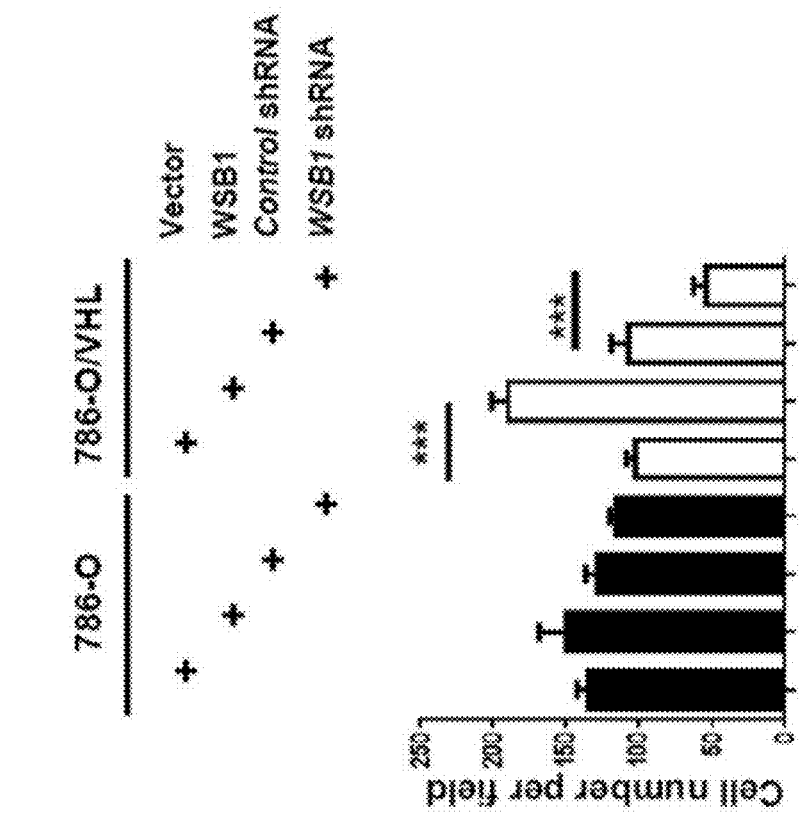

Example 6—WSB1 Promotes Cancer Cell Invasion, Migration and Metastasis by Inhibiting pVHL To determine whether WSB1 upregulates HIF-1α levels and promotes tumor metastasis by down regulating pVHL, RCC4 and 786-O renal carcinoma cell lines lacking pVHL were used, as were their derivatives reconstituted with HA-pVHL (RCC4/VHL and 786-O/VHL; Li et al., *Mol Cell Biol* 27:5381-5392, 2007). These studies showed that overexpression of WSB1 had no effect on HIF-1α and HIF-2α levels in VHL-deficient RCC4 and 786-O cells (FIGS. 13A and 14A). WSB1 was able to increase HIF-1α levels only in cells reconstituted with pVHL. Overexpression of WSB1 had no significant effect on cell invasiveness and mobility in VHL-deficient RCC4 and 786-O cells (FIGS. 13B, 13C, and 14B-14D), while substantially increasing cell motility and invasiveness of cells reconstituted with pVHL. Further, depletion of WSB1 decreased HIF-1α activity only in RCC4/VHL cells and 786-O/VHL cells, but did not affect HIF-1α activity in RCC4 and 786-O cells (FIG. 13D). Reconstitution of cells with WT but not WSB1 ΔSOCS in cells depleted of WSB1 restored HIF-1α levels and activity (FIG. 13D). Similar results were obtained using the breast cancer cell line MDA-MB 231 (FIGS. 14E-14G). These results suggested that WSB1 regulates HIF, cell motility, and cell invasion through pVHL.

Figure 15:
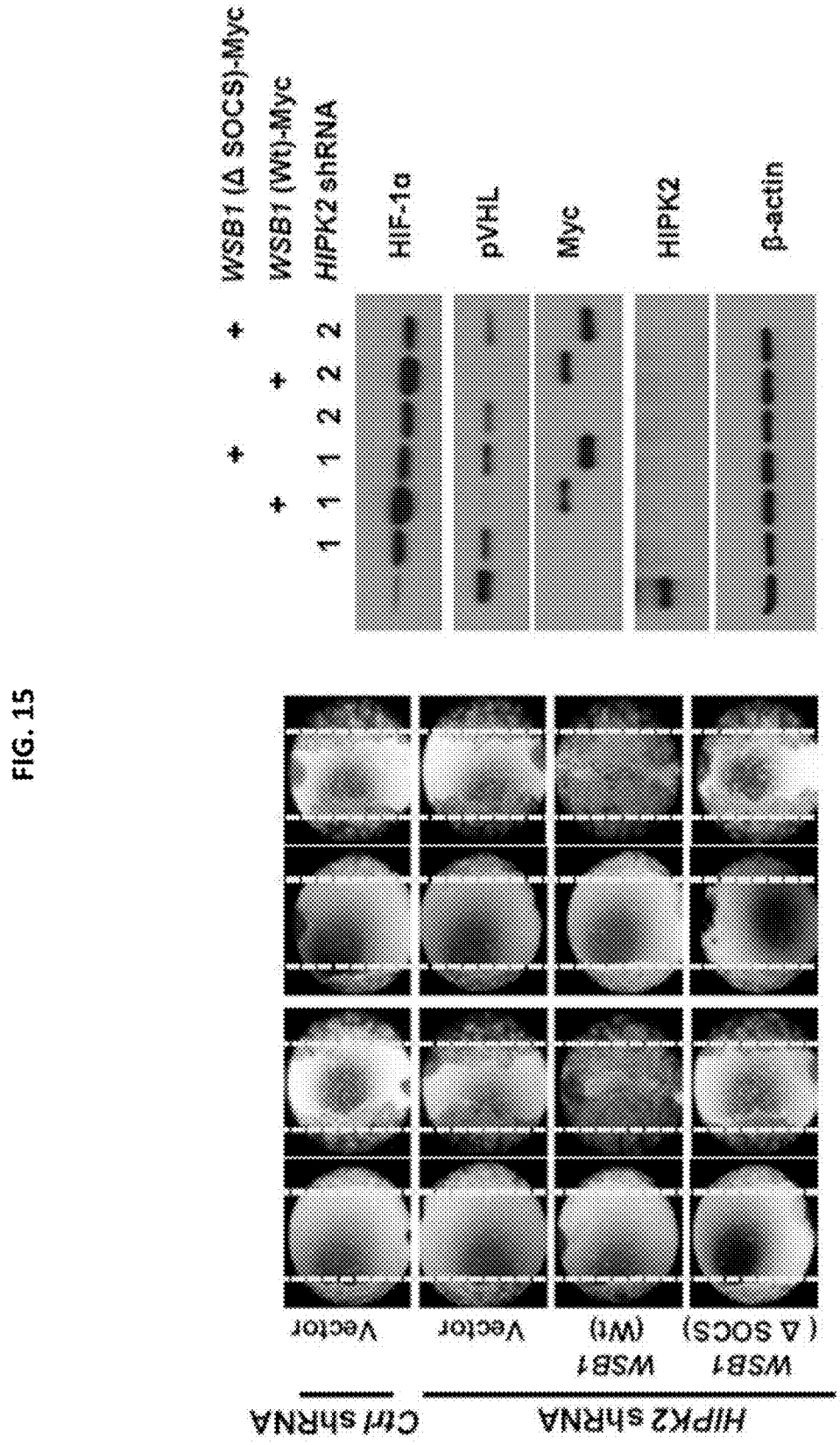
FIG. 15 demonstrates that WSB1 regulates HIF-1α in a HIPK2 independent manner. Left panel: Cells were infected with the indicated shRNA and assayed by wound healing experiments. Right panel: Expression of the indicated proteins was examined by immunoblotting.

WSB1 can down regulate HIPK2 through its E3 ligase activity (Choi et al., supra; and Tong et al., supra). Because HIPK2 regulates multiple cellular processes, including p53 activation (Jin et al., *Nature Med* 18:580-588, 2012; Puca et al., supra; and Rinaldo et al., *Molecular Cell* 47:87-98, 2012), experiments were carried out to test whether HIPK2 regulation by WSB1 plays a role in HIF-1α activity and cell mobility. As shown in FIG. 15, WSB1 overexpression was able to increase HIF-1α levels and cell mobility in cells depleted of HIPK2, suggesting that WSB1 regulates HIF-1α in a HIPK2 independent manner.

Figure 16A:
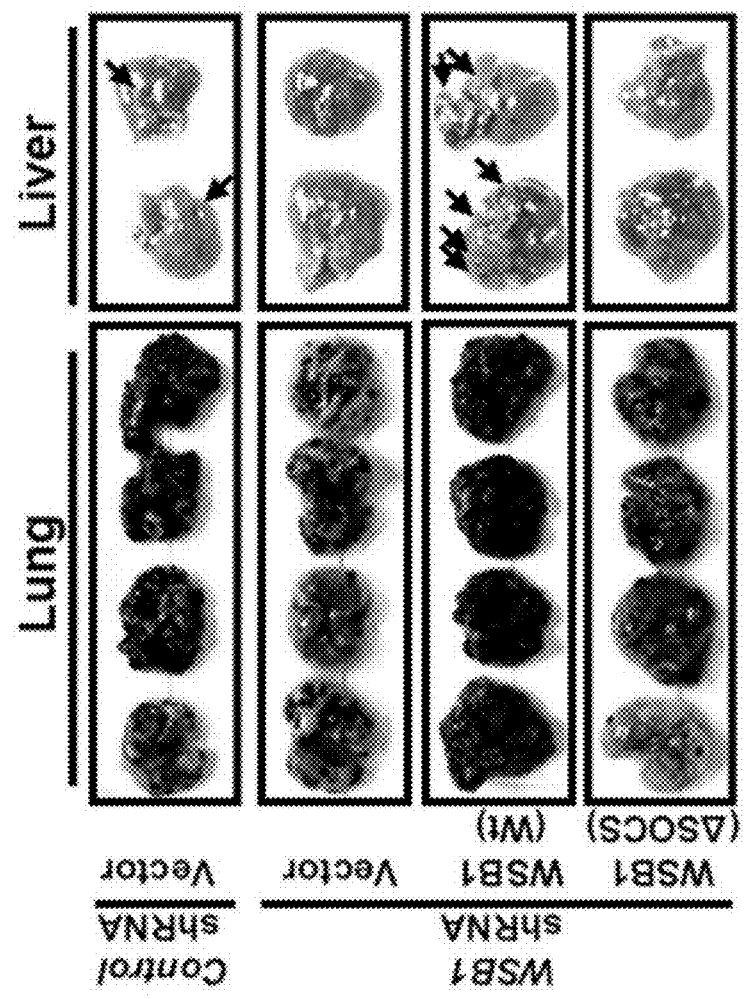
FIGS. 16A-16E demonstrate that WSB1 promotes cancer cell metastasis and is negatively correlated with pVHL in various human cancers.
Figure 16B:
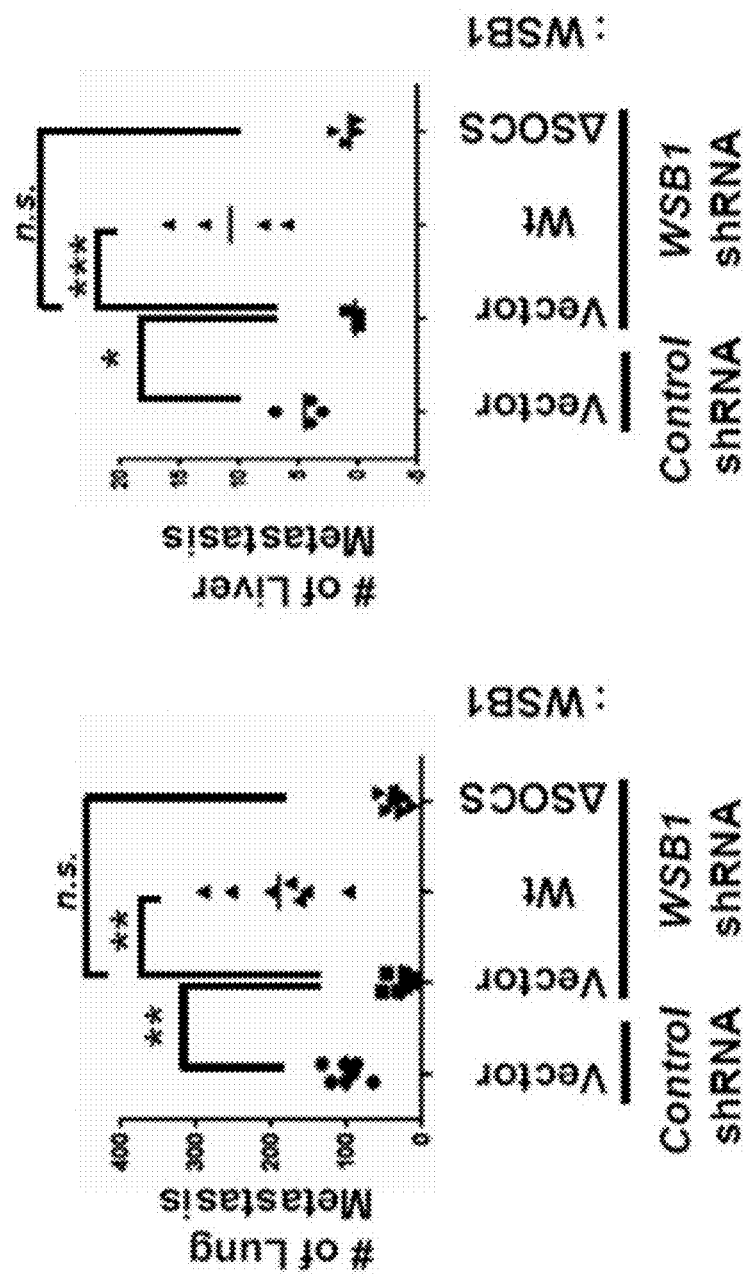
Figure 16C:
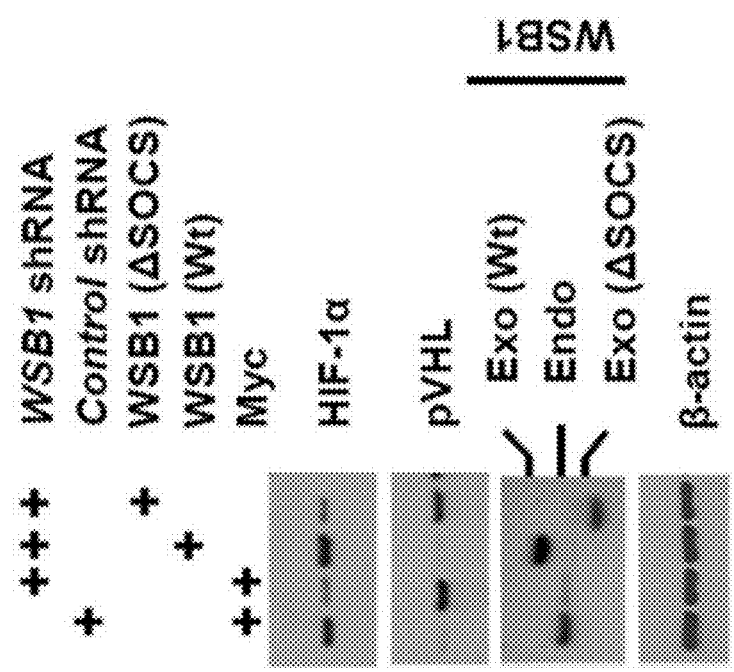

To investigate the functional relevance of the WSB1-pVHL axis in malignant behavior in vivo, cellular metastasis assays were conducted in vivo in mouse models. Depletion of WSB1 resulted in significantly decreased lung and liver colonization of B16F10 melanoma cells after tail-vein injection. These effects were reversed by reconstitution of WT WSB1 but not WSB1 ΔSOCS (FIGS. 16A-16C). Thus, WSB1 appears to be important for metastasis in malignant tumors through pVHL degradation and HIF-1α up regulation.

Figure 16D:
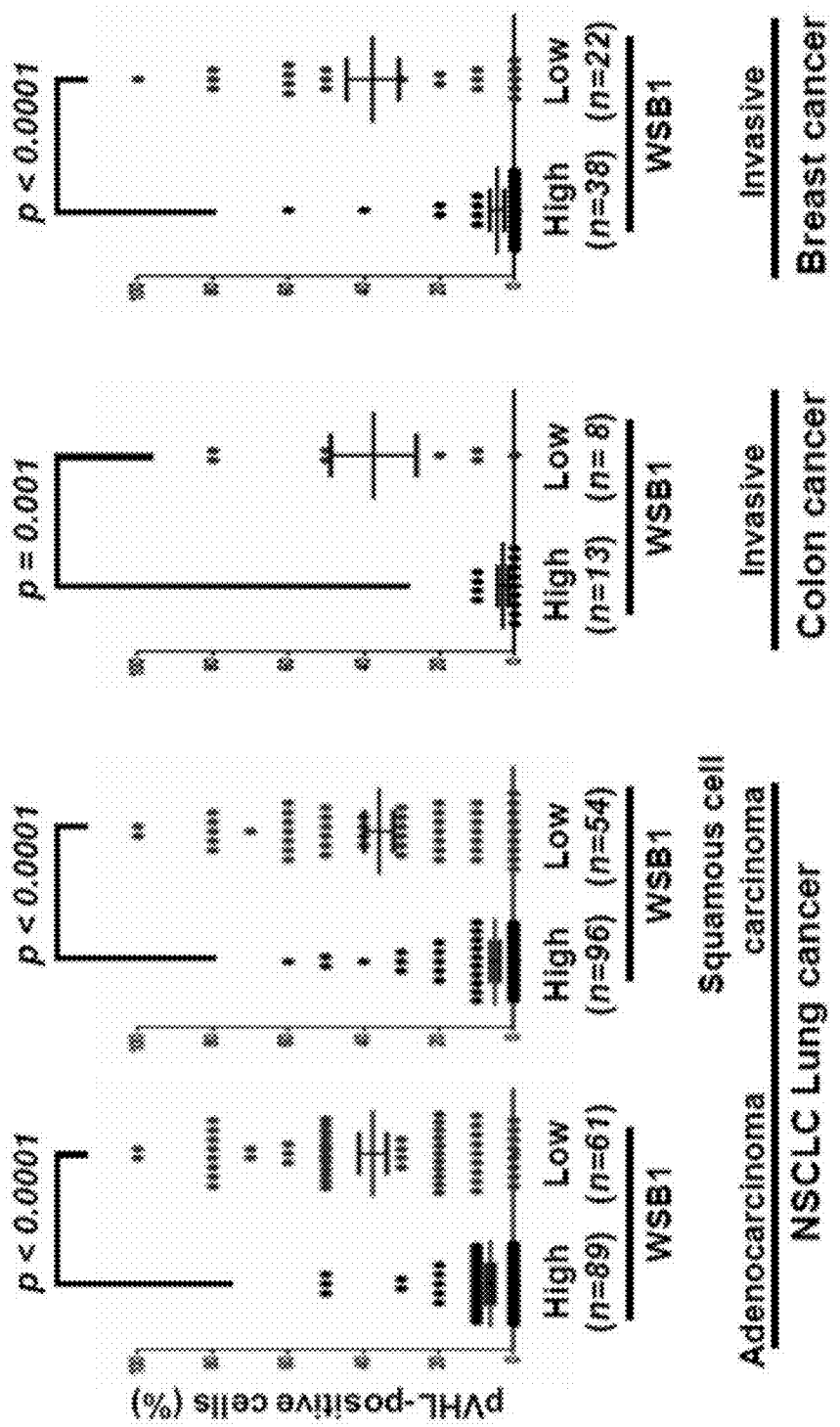
Figure 16E:
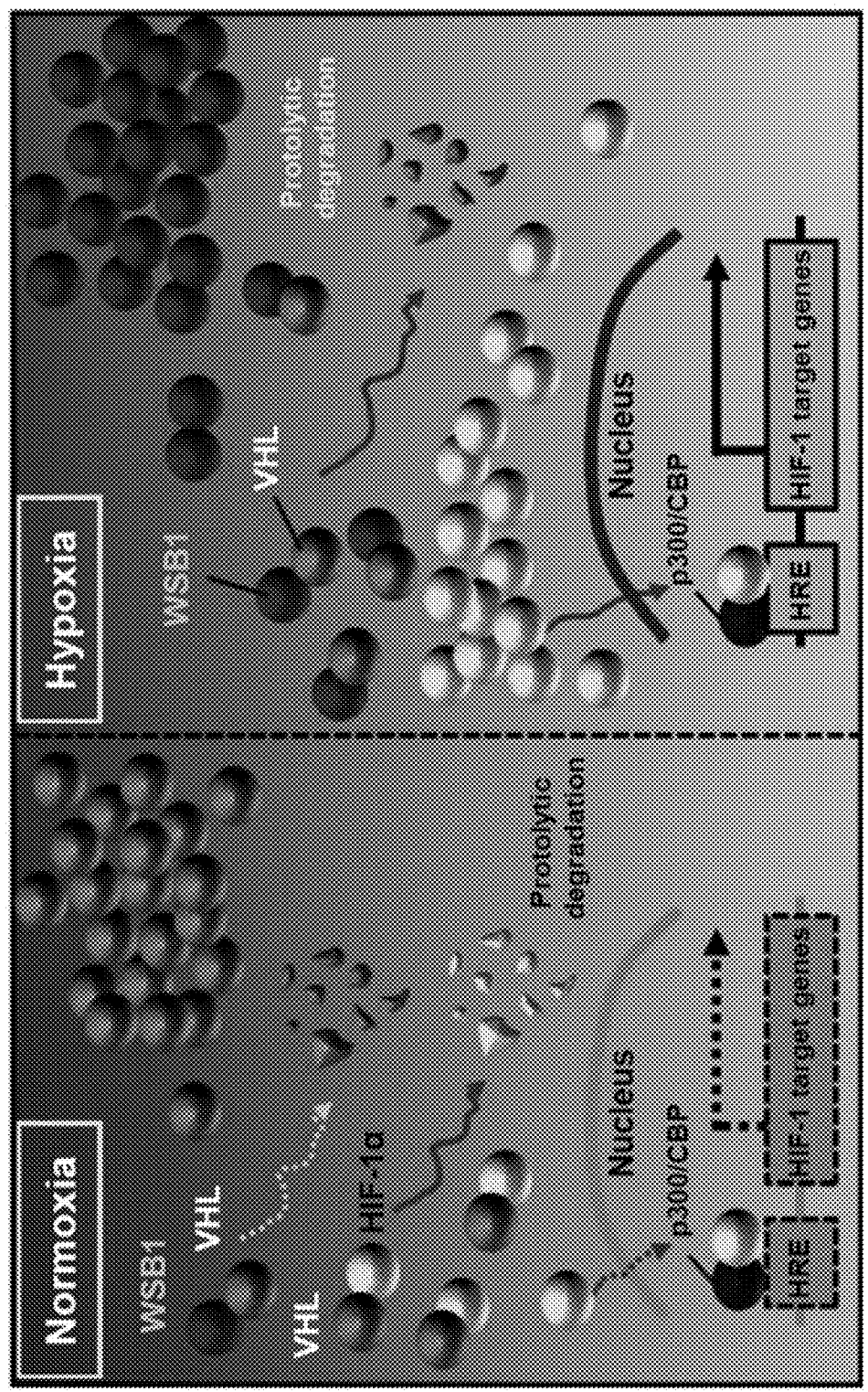
Figure 17A:
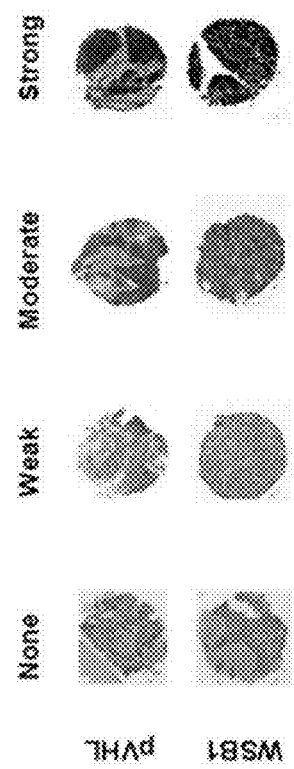
FIGS. 17A and 17B show immunohistochemical (IHC) staining of WSB1 and pVHL in human NSCLC tissue microarrays (TMA).
Figure 17B:
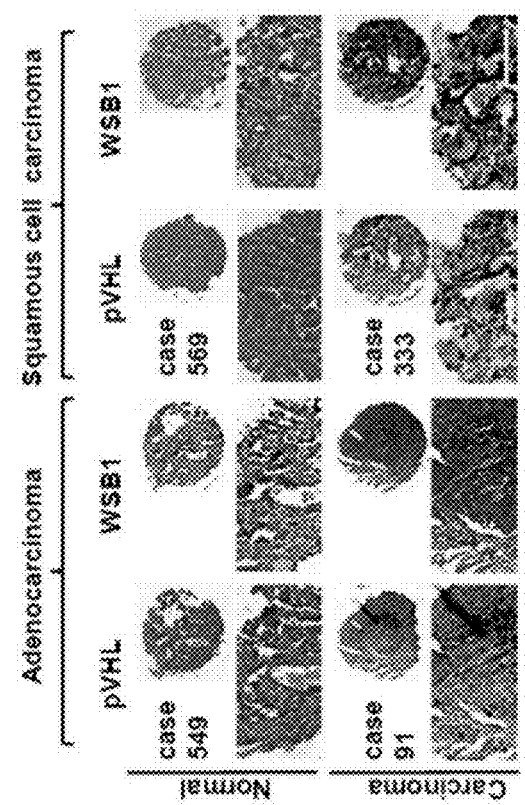

Finally, to examine the expression of WSB1 and pVHL in human tumor tissue, immuno-histochemical staining of WSB1 and pVHL was performed in 400 lung cancer specimens spotted on a tissue microarray (FIGS. 17A and 17B), and on 60 metastatic breast and 21 metastatic colorectal carcinoma patients' slides (FIG. 16D). WSB1 expression was higher in cancer lesions compared to normal adjacent tissues, while pVHL expression generally was negatively correlated with WBS1. These results are consistent with the negative regulation of pVHL by WSB1 in human cancers.

TABLE 1

| Cancer Type | Data set | Platform | Series | #samples Total | Metastasis |
|---|---|---|---|---|---|
| Melanoma | GDS3966 | GPL96 | GSE840 | 83 | 50 |
| Prostate | GDS2545 | GPL8300 | GSE6916 | 171 | 25 |
| Synchronous and metachronous liver metastases from colorectal cancer | GDS3501 | GPL570 | GSE10961 | 18 | 18 |
| Carcinoma in situ lesions of the urinary bladder | GDS1479 | GPL96 | GSE3167 | 37 | 13 |
| Breast | GDS3096 | GPL96 | GSE5847 | 47 | 34 |

TABLE 2

| ID | Genes in dataset | p-value (Wsb1 status) | Fold-Change (WSB1 High Expression vs WSB1 Low expression) |
|---|---|---|---|
| CXCR4 | CXCR4 | 9.29E−08 | 2.365 |
| AKT2 | AKT2 | 3.50594E−07 | 2.241 |
| PTCH | PTCH1 | 1.36E−07 | 2.184 |
| MMP11 | MMP11 | 0.019739 | 2.168 |
| HGF | HGF | 2.24632E−10 | 2.128 |
| FABP5 | FABP5 | 3.0097E−07 | 2.069 |
| IL8RB | CXCR2 | 4.12E−06 | 2.042 |
| EGF | EGF | 2.83822E−06 | 2.026 |
| CD274 | CD274 | 5.04073E−08 | 1.985 |
| SLC7A11 | SLC7A11 | 0.000904253 | 1.980 |
| CUTL1 | CUX1 | 1.07E−09 | 1.933 |
| ANGPT2 | ANGPT2 | 0.0012662 | 1.918 |
| PGF | PGF | 0.00637047 | 1.891 |
| PPM1D | PPM1D | 9.39074E−09 | 1.875 |
| ZAP70 | ZAP70 | 1.48671E−08 | 1.844 |
| MMP9 | MMP9 | 3.54E−05 | 1.840 |
| CA4 | CA4 | 0.011951 | 1.782 |
| ITGB3 | ITGB3 | 9.60728E−05 | 1.768 |
| VEGFA | VEGFA | 1.14E−05 | 1.749 |
| NR4A1 | NR4A1 | 0.008555 | 1.716 |
| TACSTD1 | EPCAM | 2.53482E−06 | 1.702 |
| NUAK1 | NUAK1 | 1.26095E−07 | 1.693 |
| LGALS3 | LGALS3 | 3.68585E−10 | 1.686 |
| HK2 | HK2 | 3.52E−06 | 1.683 |
| TGFB2 | TGFB2 | 0.000162424 | 1.677 |
| SLC38A6 | SLC38A6 | 2.54046E−09 | 1.667 |
| NT5E | NT5E | 4.88986E−05 | 1.651 |
| CCR4 | CCR4 | 0.0029205 | 1.645 |
| HTATIP2 | HTATIP2 | 3.39708E−05 | 1.839 |
| OLFML3 | OLFML3 | 6.39708E−07 | 1.617 |
| ANK3 | ANK3 | 1.29437E−07 | 1.609 |
| CSF1 | CSF1 | 2.05E−06 | 1.602 |
| SP4 | SP4 | 3.76181E−09 | 1.599 |
| CAPN2 | CAPN2 | 6.11261E−08 | 1.595 |
| SLC16A3 | SLC16A3 | 8.32484E−06 | 1.591 |
| DLG7 | DLGAP5 | 0.00644031 | 1.586 |
| CYP1B1 | CYP1B1 | 6.01141E−07 | 1.580 |
| ESR1 | ESR1 | 0.000711501 | 1.574 |

TABLE 2-continued

| ID | Genes in dataset | p-value (Wsb1 status) | Fold-Change (WSB1 High Expression vs WSB1 Low expression) |
|---|---|---|---|
| TUBE1 | TUBE1 | 2.74138E-07 | 1.572 |
| NDRG1 | NDRG1 | 2.12E-05 | 1.565 |
| MET | MET | 0.000294532 | 1.561 |
| MMP2 | MMP2 | 3.50E-08 | 1.556 |
| TGFA | TGFA | 0.000114944 | 1.552 |
| TUBD1 | TUBD1 | 5.81612E-08 | 1.550 |
| CAT | CAT | 2.38149E-08 | 1.545 |
| AKR1C3 | AKR1C3 | 0.000215814 | 1.530 |
| APC | APC | 1.51751E-07 | 1.520 |
| CFLAR | CFLAR | 8.531E-11 | 1.519 |
| TNIK | TNIK | 0.00117395 | 1.515 |
| SELE | SELE | 0.000373948 | 1.512 |
| TUBB2C | TUBB4B | 2.88577E-07 | 1.509 |
| ANGPTL4 | ANGPTL4 | 2.32619E-05 | 1.505 |
| GREM2 | GREM2 | 0.0113608 | -1.519 |
| ING4 | ING4 | 7.52E-09 | -1.519 |
| PPARD | PPARD | 5.90E-05 | -1.530 |
| STAB2 | STAB2 | 0.0215461 | -1.530 |
| IL1RL1 | IL1RL1 | 0.0191785 | -1.547 |
| CLDN3 | CLDN3 | 0.000603823 | -1.559 |
| LGR4 | LGR4 | 0.00774795 | -1.581 |
| REV3L | REV3L | 3.55E-05 | -1.634 |
| DFFB | DFFB | 4.21524E-07 | -1.637 |
| NLRP1 | NLRP1 | 3.05E-05 | -1.669 |
| NFKB1 | NFKB1 | 7.13E-13 | -1.700 |
| WWOX | WWOX | 6.82828E-11 | -1.714 |
| KISS1 | KISS1 | 0.00311776 | -1.732 |
| ISLR | ISLR | 0.000414443 | -1.735 |
| SDC1 | SDC1 | 3.37E-07 | -1.792 |
| CDCA7L | CDCA7L | 7.02E-05 | -1.801 |
| CXCR7 | CXCR7 | 0.000331741 | -1.808 |
| TP53 | TP53 | 1.86E-05 | -1.817 |
| ANPEP | ANPEP | 0.0115719 | -1.847 |
| LTB4R2 | LTB4R2 | 6.01E-08 | -1.868 |
| TP73L | TP63 | 0.0133901 | -1.868 |
| CNN1 | CNN1 | 0.000290524 | -1.917 |
| PSCA | PSCA | 0.0203717 | -1.934 |
| ZNF350 | ZNF350 | 2.81979E-08 | -1.946 |
| CDKN2C | CDKN2C | 4.27E-11 | -1.986 |
| DSG2 | DSG2 | 8.64E-06 | -1.997 |
| PPARA | PPARA | 6.32E-12 | -2.024 |
| LTF | LTF | 0.000635644 | -2.156 |
| CCNA1 | CCNA1 | 1.16E-05 | -2.157 |
| C1R | C1R | 3.95E-08 | -2.272 |
| MSC | MSC | 5.97E-07 | -2.358 |
| NF2 | NF2 | 8.12E-11 | -2.454 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for treating a cancer patient, comprising administering to the cancer patient an agent that reduces the activity of WSB1, wherein the cancer is melanoma.

2. The method of claim 1, wherein the agent is an inhibitory nucleic acid targeted to a WSB1 nucleic acid that is endogenous to the cancer patient.

3. The method of claim 2, wherein the inhibitory nucleic acid is a shRNA.

4. The method of claim 1, comprising administering to the cancer patient a composition comprising the agent and a pharmaceutically acceptable carrier.

5. A method for inhibiting metastasis of a tumor in a cancer patient, comprising administering to the cancer patient an agent that reduces the activity of WSB1, wherein the cancer is melanoma.

6. The method of claim 5, wherein the agent is an inhibitory nucleic acid targeted to a WSB1 nucleic acid that is endogenous to the cancer patient.

7. The method of claim 6, wherein the inhibitory nucleic acid is a shRNA.

8. The method of claim 5, comprising administering to the cancer patient a composition comprising the agent and a pharmaceutically acceptable carrier.

* * * * *

SEQUENCE LISTING

```
<160> NUMBER OF SEQ ID NOS: 24

<210> SEQ ID NO 1
<211> LENGTH: 421
<212> TYPE: PRT
<213> ORGANISM: Homo sapiens

<400> SEQUENCE: 1

Met Ala Ser Phe Pro Pro Arg Val Asn Glu Lys Glu Ile Val Arg Leu
1               5                   10                  15

Arg Thr Ile Gly Glu Leu Leu Ala Pro Ala Pro Phe Asp Lys Lys
            20                  25                  30

Cys Gly Arg Glu Asn Trp Thr Val Ala Phe Ala Pro Asp Gly Ser Tyr
        35                  40                  45

Phe Ala Trp Ser Gln Gly His Arg Thr Val Lys Leu Val Pro Trp Ser
    50                  55                  60

Gln Cys Leu Gln Asn Phe Leu Leu His Gly Thr Lys Asn Val Thr Asn
65                  70                  75                  80

Ser Ser Ser Leu Arg Leu Pro Arg Gln Asn Ser Asp Gly Gly Gln Lys
                85                  90                  95

Asn Lys Pro Arg Glu His Ile Ile Asp Cys Gly Asp Ile Val Trp Ser
                100                 105                 110

Leu Ala Phe Gly Ser Ser Val Pro Glu Lys Gln Ser Arg Cys Val Asn
            115                 120                 125

Ile Glu Trp His Arg Phe Arg Phe Gly Gln Asp Gln Leu Leu Leu Ala
        130                 135                 140

Thr Gly Leu Asn Asn Gly Arg Ile Lys Ile Trp Asp Val Tyr Thr Gly
145                 150                 155                 160

Lys Leu Leu Leu Asn Leu Val Asp His Thr Glu Val Val Arg Asp Leu
```

165                 170                 175
Thr Phe Ala Pro Asp Gly Ser Leu Ile Leu Val Ser Ala Ser Arg Asp
            180                 185                 190

Lys Thr Leu Arg Val Trp Asp Leu Lys Asp Asp Gly Asn Met Met Lys
        195                 200                 205

Val Leu Arg Gly His Gln Asn Trp Val Tyr Ser Cys Ala Phe Ser Pro
    210                 215                 220

Asp Ser Ser Met Leu Cys Ser Val Gly Ala Ser Lys Ala Val Phe Leu
225                 230                 235                 240

Trp Asn Met Asp Lys Tyr Thr Met Ile Arg Lys Leu Glu Gly His His
                245                 250                 255

His Asp Val Val Ala Cys Asp Phe Ser Pro Asp Gly Ala Leu Leu Ala
            260                 265                 270

Thr Ala Ser Tyr Asp Thr Arg Val Tyr Ile Trp Asp Pro His Asn Gly
        275                 280                 285

Asp Ile Leu Met Glu Phe Gly His Leu Phe Pro Pro Thr Pro Ile
    290                 295                 300

Phe Ala Gly Gly Ala Asn Asp Arg Trp Val Arg Ser Val Ser Phe Ser
305                 310                 315                 320

His Asp Gly Leu His Val Ala Ser Leu Ala Asp Asp Lys Met Val Arg
                325                 330                 335

Phe Trp Arg Ile Asp Glu Asp Tyr Pro Val Gln Val Ala Pro Leu Ser
            340                 345                 350

Asn Gly Leu Cys Cys Ala Phe Ser Thr Asp Gly Ser Val Leu Ala Ala
        355                 360                 365

Gly Thr His Asp Gly Ser Val Tyr Phe Trp Ala Thr Pro Arg Gln Val
    370                 375                 380

Pro Ser Leu Gln His Leu Cys Arg Met Ser Ile Arg Arg Val Met Pro
385                 390                 395                 400

Thr Gln Glu Val Gln Glu Leu Pro Ile Pro Ser Lys Leu Leu Glu Phe
                405                 410                 415

Leu Ser Tyr Arg Ile
            420

<210> SEQ ID NO 2
<211> LENGTH: 2849
<212> TYPE: DNA
<213> ORGANISM: Homo sapiens

<400> SEQUENCE: 2
agatatctcc ggcgccgccc gccatttga ctccagtgtc tcgtttgcag tcggcgcttt      60
aggggaactg tcttcctccg caggcgcgag gctgggtaca gggtctattg tctgtggttg    120
actccgtact ttggtctgag gccttcggga gctttcccga ggcagttagc agaagccgca    180
gcggccgccc ccgcccgtct cctctgtccc tgggcccggg agggaccaac ttggcgtcac    240 gccccctcagc ggtcgccact ctcttctctg ttgttgggtc cgcatcgtat tcccggaatc    300
agacggtgcc ccatagatgg ccagctttcc cccgagggtc aacgagaaag agatcgtgag    360
attacgtact ataggtgaac ttttagctcc tgcagctcct tttgacaaga aatgtggtcg    420
tgaaaattgg actgttgctt tgctccaga tggttcatac tttgcttggt cacaaggaca    480
tcgcacagta aagcttgttc cgtggtccca gtgccttcag aactttctct gcatggcac    540 caagaatgtt accaattcaa gcagtttaag attgccaaga caaatagtg atggtggtca    600 gaaaaataag cctcgtgaac atattataga ctgtggagat atagtctgga gtcttgcttt    660

```
tgggtcatca gttccagaaa aacagagtcg ctgtgtaaat atagaatggc atcgcttcag      720
atttggacaa gatcagctac ttcttgctac agggttgaac aatgggcgta tcaaaatatg      780
ggatgtatat acaggaaaac tcctccttaa cttggtagat catactgaag tggtcagaga      840
tttaactttt gctccagatg gaagcttgat cctggtgtca gcttcaagag acaaaactct      900
cagagtatgg gacctgaaag atgatggaaa catgatgaaa gtattgaggg gcatcagaa       960 ttgggtgtac agctgtgcat tctctcctga ctcttctatg ctgtgttcag tcggagccag     1020
taaagcagtt ttcctttgga atatggataa atacaccatg atacggaaac tagaaggaca     1080
tcaccatgat gtggtagctt gtgactttc tcctgatgga gcattactgg ctactgcatc      1140
ttatgatact cgagtatata tctgggatcc acataatgga gacattctga tggaatttgg     1200
gcacctgttt cccccaccta ctccaatatt tgctggagga gcaaatgacc ggtgggtacg     1260
atctgtatct tttagccatg atggactgca tgttgcaagc cttgctgatg ataaaatggt     1320
gaggttctgg agaattgatg aggattatcc agtgcaagtt gcacctttga caatggtct      1380 ttgctgtgcc ttctctactg atggcagtgt tttagctgct gggacacatg acggaagtgt     1440
gtattttggg ccactccac ggcaggtccc tagcctgcaa catttatgtc gcatgtcaat      1500
ccgaagagtg atgcccaccc aagaagttca ggagctgccg attccttcca gcttttgga     1560 gtttctctcg tatcgtattt agaagattct gccttcccta gtagtaggga ctgacagaat    1620
acacttaaca caaacctcaa gctttactga cttcaattat ctgtttttaa agacgtagaa     1680
gatttattta atttgatatg ttcttgtact gcattttgat cagttgagct ttaaaaatat     1740
tatttataga caatagaagt atttctgaac atatcaaata taaatttttt taaagatcta     1800
actgtgaaaa catacatacc tgtacatatt tagatataag ctgctatatg ttgaatggac     1860
ccttttgctt ttctgatttt tagttctgac atgtatatat tgcttcagta gagccacaat     1920
atgtatcttt gctgtaaagt gcaaggaaat tttaaattct gggacactga gttagatggt     1980
aaatactgac ttacgaaagt tgaattgggt gaggcgggca aatcacctga ggtcagcagt     2040
ttgagactag cctggcaaac atgatgaaac cctgtctcta ctaaaaatac aaaaaaaaaa     2100
aaaattagcc aggcgtggtg gtgcacacct gtagtcctag ctacttggga ggctgaggca     2160
ggagaattgc ttgaacccag gaggtggagg ttgcagtaag ccaagatcac accactgcac     2220
tccaacctgg acaacagagc gagactccat ctcaaaaaaa aaaaaaaatt gtgttgcctc     2280
atacgaaatg tatttggttt tgttggagag tgtcagactg atctggaagt gaaacacagt     2340
ttatgtacag ggaaaaggat tttattatcc ttaggaatgt catccaagac gtagagcttg     2400
aatgtgacgt tatttaaaaa caacaacaaa gaaggcagag ccaggatata actagaaaaa     2460
ggatgtcttt ttttttttt ttactccccc tctaaacact gctgctgcct taattttaga     2520
aagcagctta ctagtttacc cttgtggtat aaagtattat aaattgttgt gaatttgaag     2580
aatccgtcta ctgtattatt gctaaatatt tgtttatac taagggacaa ttattttaag     2640
accatggatt taaaaaaaaa aaaaaaaact ctgtttctgc aggggatgat attggtgagt     2700
tgccaaagaa gcaatacagc atatctgctt ttgccttctg ttgtttatct tacctgcaga     2760
tattaagaat gtatgcatta tgtaaaatgc tcaattatat attttgttg agttttttaa      2820 ttaaagactt gttaaaaaaa aaaaaaaa                                        2849
```

<210> SEQ ID NO 3
<211> LENGTH: 213
<212> TYPE: PRT

<213> ORGANISM: Homo sapiens

<400> SEQUENCE: 3

```
Met Pro Arg Arg Ala Glu Asn Trp Asp Glu Ala Glu Val Gly Ala Glu
1               5                   10                  15

Glu Ala Gly Val Glu Glu Tyr Gly Pro Glu Glu Asp Gly Gly Glu Glu
            20                  25                  30

Ser Gly Ala Glu Glu Ser Gly Pro Glu Glu Ser Gly Pro Glu Glu Leu
        35                  40                  45

Gly Ala Glu Glu Glu Met Glu Ala Gly Arg Pro Arg Pro Val Leu Arg
    50                  55                  60

Ser Val Asn Ser Arg Glu Pro Ser Gln Val Ile Phe Cys Asn Arg Ser
65                  70                  75                  80

Pro Arg Val Val Leu Pro Val Trp Leu Asn Phe Asp Gly Glu Pro Gln
                85                  90                  95

Pro Tyr Pro Thr Leu Pro Pro Gly Thr Gly Arg Arg Ile His Ser Tyr
            100                 105                 110

Arg Gly His Leu Trp Leu Phe Arg Asp Ala Gly Thr His Asp Gly Leu
        115                 120                 125

Leu Val Asn Gln Thr Glu Leu Phe Val Pro Ser Leu Asn Val Asp Gly
    130                 135                 140

Gln Pro Ile Phe Ala Asn Ile Thr Leu Pro Val Tyr Thr Leu Lys Glu
145                 150                 155                 160

Arg Cys Leu Gln Val Val Arg Ser Leu Val Lys Pro Glu Asn Tyr Arg
                165                 170                 175

Arg Leu Asp Ile Val Arg Ser Leu Tyr Glu Asp Leu Glu Asp His Pro
            180                 185                 190

Asn Val Gln Lys Asp Leu Glu Arg Leu Thr Gln Glu Arg Ile Ala His
        195                 200                 205

Gln Arg Met Gly Asp
    210
```

<210> SEQ ID NO 4
<211> LENGTH: 4560
<212> TYPE: DNA
<213> ORGANISM: Homo sapiens

<400> SEQUENCE: 4

```
cctcgcctcc gttacaacgg cctacggtgc tggaggatcc ttctgcgcac gcgcacagcc      60
tccggccggc tatttccgcg agcgcgttcc atcctctacc gagcgcgcgc gaagactacg     120
gaggtcgact cgggagcgcg cacgcagctc cgccccgcgt ccgacccgcg gatcccgcgg     180
cgtccggccc gggtggtctg gatcgcgagg ggaatgcccc ggagggcgga gaactgggac     240
gaggccgagg taggcgcgga ggaggcaggc gtcgaagagt acggccctga agaagacggc     300
ggggaggagt cgggcgccga ggagtccggc ccggaagagt ccggcccgga ggaactgggc     360
gccgaggagg agatggaggc cgggcggccg cggcccgtgc tgcgctcggt gaactcgcgc     420
gagccctccc aggtcatctt ctgcaatcgc agtccgcgcg tcgtgctgcc cgtatggctc     480
aacttcgacg gcgagccgca gccctaccca acgctgccgc ctggcacggg ccgccgcatc     540
cacagctacc gaggtcacct ttggctcttc agagatgcag gcacacgat gggcttctg     600 gttaaccaaa ctgaattatt gtgccatct ctcaatgttg acggacagcc tattttgcc     660 aatatcacac tgccagtgta tactctgaaa gagcgatgcc tccaggttgt ccggagccta     720
gtcaagcctg agaattacag gagactggac atcgtcaggt cgctctacga agatctggaa     780
```

```
gaccacccaa atgtgcagaa agacctggag cggctgacac aggagcgcat tgcacatcaa    840
cggatgggag attgaagatt tctgttgaaa cttacactgt ttcatctcag cttttgatgg    900
tactgatgag tcttgatcta gatacaggac tggttccttc cttagtttca aagtgtctca    960
ttctcagagt aaaataggca ccattgctta aagaaagtt aactgacttc actaggcatt    1020
gtgatgttta gggcaaaca tcacaaaatg taatttaatg cctgcccatt agagaagtat    1080
ttatcaggag aaggtggtgg cattttttgct tcctagtaag tcaggacagc ttgtatgtaa    1140
ggaggtttgt ataagtaatt cagtgggaat tgcagcatat cgtttaattt taagaaggca    1200
ttggcatctg cttttaatgg atgtataata catccattct acatccgtag cggttggtga    1260
cttgtctgcc tcctgctttg gaagactga ggcatccgtg aggcagggac aagtctttct    1320
cctctttgag accccagtgc ctgcacatca tgagccttca gtcagggttt gtcagaggaa    1380
caaaccaggg gacactttgt tagaaagtgc ttagaggttc tgcctctatt tttgttgggg    1440
ggtgggagag gggaccttaa aatgtgtaca gtgaacaaat gtcttaaagg gaatcatttt    1500
tgtaggaagc attttttata attttctaag tcgtgcactt tctcggtcca ctcttgttga    1560
agtgctgttt tattactgtt tctaaactag gattgacatt ctacagttgt gataatagca    1620
ttttttgtaac ttgccatccg cacagaaaat acgagaaaat ctgcatgttt gattatagta    1680
ttaatggaca aataagtttt tgctaaatgt gagtatttct gttcctttt gtaaatatgt    1740
gacattcctg attgatttgg gtttttttgt tgttgttgtt ttgttttgtt ttgttttttt    1800
gagatggagt ctcactcttg tcacccaggc tggagtgcag tggcgccatc tcggctcact    1860
gcaacctctg cctcctgggt tcacgtaatc ctcctgagta gctgggatta caggcgcctg    1920
ccaccacgct ggccaatttt tgtacttta gtagagacag tgtttcgcca tgttggccag    1980
gctggtttca aactcctgac ctcaggtgat ccgcccacct cagcctccca aaatggtggg    2040
attacaggtg tgtgggccac cgtgcctggc tgattcagca ttttttatca ggcaggacca    2100
ggtggcactt ccacctccag cctctggtcc taccaatgga ttcatggagt agcctggact    2160
gtttcatagt tttctaaatg tacaaattct tataggctag acttagattc attaactcaa    2220
attcaatgct tctatcagac tcagttttttt gtaactaata gattttttt tccacttttg    2280
ttctactcct tccctaatag cttttttaaaa aaatctcccc agtagagaaa catttggaaa    2340
agacagaaaa ctaaaaagga agaaaaaaga tccctattag atacacttct taaatacaat    2400
cacattaaca ttttgagcta tttccttcca gccttttag ggcagatttt ggttggtttt    2460
tacatagttg agattgtact gttcatacag ttttataccc ttttcattt aactttataa    2520
cttaaatatt gctctatgtt agtataagct tttcacaaac attagtatag tctcccttt    2580
ataattaatg tttgtgggta tttcttggca tgcatcttta attccttatc ctagcctttg    2640
ggcacaattc ctgtgctcaa aaatgagagt gacggctggc atggtggctc cgcctgtaa    2700
tcccagtact ttggaaagcc aaggtaagag gattgcttga gcccagaact tcaagatgag    2760
cctgggctca tagtgagaac ccatctatac aaaaaatttt taaaaattag catggcggca    2820
cacatctgta atcctagcta cttggcaggc tgaggtgaga agatcattgg agtttaggaa    2880
ttggaggctg cagtgagcca tgagtatgcc actgcactcc agcctgggg acagagcaag    2940
accctgcctc aaaaaaaaaa aaaaaaaaa aatcaggccg gcatggtgg ctcacgcctg    3000
taatcccagc actttgggag gtcgaggtgg gcagatcacc tgaggtcagg agttcgagac    3060
cagcctggcc aacatggtaa aaccccattt ctactaaaaa atacaagaat tagctgggtg    3120
```

```
tggtggcgca tgcctgtaat cctagctact caggaggctg aggcaggaga atcacttgaa    3180
cccaggaggc gaagattgca gtgagctgat atcgcaccat tgtactccag cctgtgtgac    3240
agagcaatac tcttgtctca aaaaaaaaaa aaaattcaaa tcagagtgaa gtgaatgaga    3300
cactccagtt ttccttctac tccgaatttc aactgatttt agctcctcct ttcaacattc    3360
aacaaatagt cttttttttt ttttttttt  ttttttttt  gagatggagt ctcactctgt    3420
tgcccaggct ggagtgcagt ggtgcgatct ctgctcacta caagctctgc ctcccgagtt    3480
caagtgattc tcctggctca ccctcctgag tagctgggat tacaggcgcc tgccaccatg    3540
cctggctaat tttgtgtttt tagtggagac ggggtttcac catgttgtcc aggatggtct    3600
tgatctcctg accttgtgat ccacccacct cagcctccca aagtgctggg attacaggtg    3660
tgagccaccg cgtccagcca gctttattat tttttttaag ctgtctttgt gtcaaaatga    3720
tagttcatgc tcctcttgtt aaaacctgca ggccgagcac agtggctcat gcctgtaatc    3780
ccagcatttt gggagaccaa ggcggatgga tcacctgagg tcaggagctg aagaccagcc    3840
tggctaacat ggtgaaacct catctccact aaaatacaa  aaattgccgg ccgcggcggc    3900
tcatgcctgt aatcccagca ctttgggagg cctaggcggg tggatcacga ggtcaggaaa    3960
tcgagaccat cctggctaac acgggtgaaa ccccgtctct attaaaaaat agaaaaaatt    4020
aggcgggcgt ggtggtgagc gcctgtagtc ccagctactc gagagcctga ggcaggagaa    4080
tggcatgaac ctgaaggcg  gagcttgcag tgagctgaga tggtgccact gcactctaac    4140
ctgggcgaca gagtgagaca ccgtctcaaa aaaaaaaca  aaaacaaaa  attatccagg    4200 tgtggcggtg ggcgcctgtg aggcaggcga atctcttgaa cccgggaggc ggaggttgca    4260
gtgagccaag atcacaccat tgcactccag cctgggcaac aagagtgaaa ttccatctca    4320 aaagaaacc  aaaaaaacaa aaaaaaaaca tgccgtttga gtactgtgtt tttggtgttg    4380
tccaaggaaa attaaaaacc tgtagcatga ataatgtttg ttttcatttt cgaatcttgt    4440
gaatgtatta aatatatcgc tcttaagaga cggtgaagtt cctatttcaa gttttttttt    4500
tttttttttt ttttaaagct gttttttaat acattaaatg gtgctgagta aaggaaatag    4560
```

```
<210> SEQ ID NO 5
<211> LENGTH: 97
<212> TYPE: DNA
<213> ORGANISM: Artificial Sequence
<220> FEATURE:
<223> OTHER INFORMATION: synthetic oligonucleotide

<400> SEQUENCE: 5
tgctgttgac agtgagcgcg gagtttctct cgtatcgtat tagtgaagcc acagatgtaa    60
tacgatacga gagaaactcc atgcctactg cctcgga                            97

<210> SEQ ID NO 6
<211> LENGTH: 97
<212> TYPE: DNA
<213> ORGANISM: Artificial Sequence
<220> FEATURE:
<223> OTHER INFORMATION: synthetic oligonucleotide

<400> SEQUENCE: 6
tgctgttgac agtgagcgcg ctgtaaagtg caaggaaatt tagtgaagcc acagatgtaa    60
atttccttgc actttacagc atgcctactg cctcgga                            97

<210> SEQ ID NO 7
<211> LENGTH: 21
```

```
<212> TYPE: DNA
<213> ORGANISM: Artificial Sequence
<220> FEATURE:
<223> OTHER INFORMATION: synthetic oligonucleotide

<400> SEQUENCE: 7
acatgagctg ctgctatata t                                               21

<210> SEQ ID NO 8
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 8
gcttactcct tgtatcagct t                                               21

<210> SEQ ID NO 9
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 9
gtgatgaaag aattaccgaa t                                               21

<210> SEQ ID NO 10
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 10
tgctctttgt ggttggatct a                                               21

<210> SEQ ID NO 11
<211> LENGTH: 96
<212> TYPE: DNA
<213> ORGANISM: Artificial Sequence
<220> FEATURE:
<223> OTHER INFORMATION: synthetic oligonucleotide

<400> SEQUENCE: 11
gctgttgaca gtgagcgacg agtcagtatc cagcccaatt agtgaagcca cagatgtaat     60
tgggctggat actgactcgg tgcctactgc ctcgga                               96

<210> SEQ ID NO 12
<211> LENGTH: 96
<212> TYPE: DNA
<213> ORGANISM: Artificial Sequence
<220> FEATURE:
<223> OTHER INFORMATION: synthetic oligonucleotide

<400> SEQUENCE: 12
gctgttgaca gtgagcgagg agagtgccga tgactataat agtgaagcca cagatgtatt     60
atagtcatcg gcactctccg tgcctactgc ctcgga                               96

<210> SEQ ID NO 13
<211> LENGTH: 20
<212> TYPE: DNA
<213> ORGANISM: Artificial Sequence
<220> FEATURE:
```

<223> OTHER INFORMATION: synthetic oligonucleotide

<400> SEQUENCE: 13
catggaaggt attgcactgc                                               20

<210> SEQ ID NO 14
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 14
cacacataca atgcactgtg g                                             21

<210> SEQ ID NO 15
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 15
ccttgccttg ctgctctacc tc                                            22

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
ttctgccctc ctccttctgc                                               20

<210> SEQ ID NO 17
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 17
caatatgagg ggtctctgac tacac                                         25

<210> SEQ ID NO 18
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 18
ggaattcagc tggactggct cagc                                          24

<210> SEQ ID NO 19
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 19
gcgctgtgtg ctgaaaatca g                                             21

-continued

```
<210> SEQ ID NO 20
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 20
ccacaatagg cacaatgcca tt                                                  22

<210> SEQ ID NO 21
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 21
agttggttgc cactttaggt c                                                   21

<210> SEQ ID NO 22
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 22
ccacgtctcc tagtgaacac c                                                   21

<210> SEQ ID NO 23
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 23
tcatcgtggc tgaactcttc ag                                                  22

<210> SEQ ID NO 24
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 24
tcacacttgg gaatcagccc c                                                   21
```